United States Patent
Wiedermann

(10) Patent No.: US 10,532,090 B2
(45) Date of Patent: Jan. 14, 2020

(54) VACCINE COMPOSITION AND USES THEREOF

(71) Applicant: Biolife Science QLD Limited, Brisbane (AU)

(72) Inventor: Ursula Wiedermann, Vienna (AT)

(73) Assignee: Biolife Science QLD Limited, Brisbane (AU)

( * ) Notice: Subject to any disclaimer, the term of this patent is extended or adjusted under 35 U.S.C. 154(b) by 0 days.

(21) Appl. No.: 15/316,868

(22) PCT Filed: Apr. 15, 2016

(86) PCT No.: PCT/AU2016/050275
§ 371 (c)(1),
(2) Date: Dec. 7, 2016

(87) PCT Pub. No.: WO2016/164980
PCT Pub. Date: Oct. 20, 2016

(65) Prior Publication Data
US 2017/0119867 A1    May 4, 2017

(30) Foreign Application Priority Data
Apr. 17, 2015   (AU) ................ 2015901375

(51) Int. Cl.
| | | |
|---|---|---|
| A61K 38/00 | (2006.01) | |
| A61K 39/00 | (2006.01) | |
| A61K 39/385 | (2006.01) | |
| A61K 45/06 | (2006.01) | |
| A61P 35/00 | (2006.01) | |

(52) U.S. Cl.
CPC .. *A61K 39/0011* (2013.01); *A61K 39/001106* (2018.08); *A61K 39/385* (2013.01); *A61K 45/06* (2013.01); *A61P 35/00* (2018.01); *A61K 2039/55505* (2013.01); *A61K 2039/55566* (2013.01); *A61K 2039/6037* (2013.01); *A61K 2039/64* (2013.01); *A61K 2039/70* (2013.01); *A61K 2039/812* (2018.08); *A61K 2039/828* (2018.08); *C12N 2760/16142* (2013.01)

(58) Field of Classification Search
CPC ..................................................... A61K 39/11
See application file for complete search history.

(56) References Cited

U.S. PATENT DOCUMENTS

| | | | | |
|---|---|---|---|---|
| 6,855,321 B1 * | 2/2005 | Rappuoli | ............ | C07K 14/005 424/184.1 |
| 7,060,284 B1 | 6/2006 | Kaumaya et al. | | |
| 8,852,604 B2 * | 10/2014 | Kammer | ............ | A61K 39/0011 424/192.1 |
| 2005/0008649 A1 | 1/2005 | Shin et al. | | |

FOREIGN PATENT DOCUMENTS

| | | | |
|---|---|---|---|
| EP | 0739984 A1 | | 10/1996 |
| WO | WO 2011/020604 A1 | | 2/2011 |
| WO | WO 2013/164354 | * | 11/2013 |
| WO | WO 2016/007499 | * | 1/2016 |

OTHER PUBLICATIONS

Skolnick et al. (Trends in Biotech., 18(1):34-39, 2000) (Year: 2000).*
Ezzell (J. NIH Res. 1995 7:46) (Year: 1995).*
Spitler (Cancer Biotherapy, 1995, 10:1-3) (Year: 1995).*
Boon (Adv. Can. Res. 1992 58:177-210) (Year: 1992).*
International Search Report and Written Opinion dated Jun. 10, 2016 for Application No. PCT/AU2016/050275.
Landgraf et al., Cytotoxicity and specificity of directed toxins composed of diphtheria toxin and the EGF-like domain of heregulin beta1. Biochemistry. Mar. 3, 1998;37(9):3220-8.
Mccluskey et al., Receptor-directed chimeric toxins created by sortase-mediated protein fusion. Mol Cancer Ther. Oct. 2013;12(10):2273-81. doi:10.1158/1535-7163.MCT-13-0358.
Extended European Search Report dated Nov. 19, 2018 for Application No. EP16779340.5.
Danishefsky et al., Development of Globo-H cancer vaccine. Acc Chem Res. Mar. 17, 2015;48(3):643-52. doi: 10.1021/ar5004187. Epub Feb. 10, 2015.
Tobias et al., Enhanced and long term immunogenicity of a Her-2/neu multi-epitope vaccine conjugated to the carrier CRM197 in conjunction with the adjuvant Montanide. BMC Cancer. Feb. 9, 2017;17(1):118. doi: 10.1186/s12885-017-3098-7.
Jasinska et al., Inhibition of tumor cell growth by antibodies induced after vaccination with peptides derived from the extracellular domain of Her-2/neu. Int J Cancer. Dec. 20, 2003;107(6): 976-83.
Wagner et al., Delayed tumor onset and reduced tumor growth progression after immunization with a Her-2/neu multi-peptide vaccine and IL-12 in c-neu transgenic mice. Breast Cancer Res Treat. Nov. 2007;106(1):29-38. Epub Jan. 3, 2007.

(Continued)

Primary Examiner — Sheela J. Huff
(74) Attorney, Agent, or Firm — Wolf, Greenfield & Sacks, P.C.

(57) ABSTRACT

The present invention provides a vaccine composition comprising: (i) an adjuvant; and (ii) at least one fusion peptide conjugated to a carrier protein, wherein the carrier protein is the diphtheria toxin variant CRM-197 (GenBank Accession No. 1007216A) and wherein the at least one fusion peptide comprises two or more non-contiguous B cell epitopes of Her2/neu selected from the group consisting of SEQ ID Nos:1-7 and 15-60 and amino acid sequences that have at least 85% identity to any of the foregoing. The present invention also extends to pharmaceutical compositions and methods of using the vaccine and/or pharmaceutical compositions, as herein described, for the treatment or prevention of a cancer characterised by the expression or overexpression of Her2/neu in a patient in need thereof.

11 Claims, 34 Drawing Sheets

Specification includes a Sequence Listing.

(56) References Cited

OTHER PUBLICATIONS

Wiedermann et al., A virosomal formulated Her-2/neu multi-peptide vaccine induces Her-2/neu-specific immune responses in patients with metastatic breast cancer: a phase I study. Breast Cancer Res Treat. Feb. 2010;119(3):673-83.

* cited by examiner

SEQUENCE LISTING

```
<160> NUMBER OF SEQ ID NOS: 62

<210> SEQ ID NO 1
<211> LENGTH: 16
<212> TYPE: PRT
<213> ORGANISM: homo sapiens

<400> SEQUENCE: 1

Arg Val Leu Gln Gly Leu Pro Arg Glu Tyr Val Asn Ala Arg His Ser
1               5                   10                  15
```

-continued

```
<210> SEQ ID NO 2
<211> LENGTH: 14
<212> TYPE: PRT
<213> ORGANISM: homo sapiens

<400> SEQUENCE: 2

Tyr Met Pro Ile Trp Lys Phe Pro Asp Glu Glu Gly Ala Cys
1               5                   10

<210> SEQ ID NO 3
<211> LENGTH: 17
<212> TYPE: PRT
<213> ORGANISM: homo sapiens

<400> SEQUENCE: 3

Pro Glu Ser Phe Asp Gly Asp Pro Ala Ser Asn Thr Ala Pro Leu Gln
1               5                   10                  15

Pro

<210> SEQ ID NO 4
<211> LENGTH: 23
<212> TYPE: PRT
<213> ORGANISM: homo sapiens

<400> SEQUENCE: 4

Pro Glu Ser Phe Asp Gly Asp Pro Ala Ser Asn Thr Ala Pro Leu Gln
1               5                   10                  15

Pro Gly Gly Gly Gly Gly Cys
            20

<210> SEQ ID NO 5
<211> LENGTH: 16
<212> TYPE: PRT
<213> ORGANISM: homo sapiens

<400> SEQUENCE: 5

Arg Val Leu Gln Gly Leu Pro Arg Glu Tyr Val Asn Ala Arg His Cys
1               5                   10                  15

<210> SEQ ID NO 6
<211> LENGTH: 14
<212> TYPE: PRT
<213> ORGANISM: homo sapiens

<400> SEQUENCE: 6

Tyr Met Pro Ile Trp Lys Phe Pro Asp Glu Glu Gly Ala Ser
1               5                   10

<210> SEQ ID NO 7
<211> LENGTH: 18
<212> TYPE: PRT
<213> ORGANISM: homo sapiens

<400> SEQUENCE: 7

Pro Glu Ser Phe Asp Gly Asp Pro Ala Ser Asn Thr Ala Pro Leu Gln
1               5                   10                  15

Pro Cys

<210> SEQ ID NO 8
<211> LENGTH: 49
<212> TYPE: PRT
<213> ORGANISM: homo sapiens

<400> SEQUENCE: 8
```

```
Pro Glu Ser Phe Asp Gly Asp Pro Ala Ser Asn Thr Ala Pro Leu Gln
1               5                   10                  15

Pro Arg Val Leu Gln Gly Leu Pro Arg Glu Tyr Val Asn Ala Arg His
            20                  25                  30

Ser Leu Pro Tyr Met Pro Ile Trp Lys Phe Pro Asp Glu Glu Gly Ala
        35                  40                  45

Cys

<210> SEQ ID NO 9
<211> LENGTH: 47
<212> TYPE: PRT
<213> ORGANISM: homo sapiens

<400> SEQUENCE: 9

Arg Val Leu Gln Gly Leu Pro Arg Glu Tyr Val Asn Ala Arg His Ser
1               5                   10                  15

Pro Glu Ser Phe Asp Gly Asp Pro Ala Ser Asn Thr Ala Pro Leu Gln
            20                  25                  30

Pro Tyr Met Pro Ile Trp Lys Phe Pro Asp Glu Glu Gly Ala Cys
        35                  40                  45

<210> SEQ ID NO 10
<211> LENGTH: 47
<212> TYPE: PRT
<213> ORGANISM: homo sapiens

<400> SEQUENCE: 10

Pro Glu Ser Phe Asp Gly Asp Pro Ala Ser Asn Thr Ala Pro Leu Gln
1               5                   10                  15

Pro Arg Val Leu Gln Gly Leu Pro Arg Glu Tyr Val Asn Ala Arg His
            20                  25                  30

Ser Tyr Met Pro Ile Trp Lys Phe Pro Asp Glu Glu Gly Ala Cys
        35                  40                  45

<210> SEQ ID NO 11
<211> LENGTH: 47
<212> TYPE: PRT
<213> ORGANISM: homo sapiens

<400> SEQUENCE: 11

Pro Glu Ser Phe Asp Gly Asp Pro Ala Ser Asn Thr Ala Pro Leu Gln
1               5                   10                  15

Pro Tyr Met Pro Ile Trp Lys Phe Pro Asp Glu Glu Gly Ala Ser Arg
            20                  25                  30

Val Leu Gln Gly Leu Pro Arg Glu Tyr Val Asn Ala Arg His Cys
        35                  40                  45

<210> SEQ ID NO 12
<211> LENGTH: 48
<212> TYPE: PRT
<213> ORGANISM: homo sapiens

<400> SEQUENCE: 12

Arg Val Leu Gln Gly Leu Pro Arg Glu Tyr Val Asn Ala Arg His Ser
1               5                   10                  15

Tyr Met Pro Ile Trp Lys Phe Pro Asp Glu Glu Gly Ala Ser Pro Glu
            20                  25                  30

Ser Phe Asp Gly Asp Pro Ala Ser Asn Thr Ala Pro Leu Gln Pro Cys
        35                  40                  45
```

<210> SEQ ID NO 13
<211> LENGTH: 47
<212> TYPE: PRT
<213> ORGANISM: homo sapiens

<400> SEQUENCE: 13

Tyr Met Pro Ile Trp Lys Phe Pro Asp Glu Glu Gly Ala Ser Pro Glu
1               5                   10                  15

Ser Phe Asp Gly Asp Pro Ala Ser Asn Thr Ala Pro Leu Gln Pro Arg
            20                  25                  30

Val Leu Gln Gly Leu Pro Arg Glu Tyr Val Asn Ala Arg His Cys
        35                  40                  45

<210> SEQ ID NO 14
<211> LENGTH: 48
<212> TYPE: PRT
<213> ORGANISM: homo sapiens

<400> SEQUENCE: 14

Tyr Met Pro Ile Trp Lys Phe Pro Asp Glu Glu Gly Ala Ser Arg Val
1               5                   10                  15

Leu Gln Gly Leu Pro Arg Glu Tyr Val Asn Ala Arg His Ser Pro Glu
            20                  25                  30

Ser Phe Asp Gly Asp Pro Ala Ser Asn Thr Ala Pro Leu Gln Pro Cys
        35                  40                  45

<210> SEQ ID NO 15
<211> LENGTH: 17
<212> TYPE: PRT
<213> ORGANISM: homo sapiens

<400> SEQUENCE: 15

Pro Glu Ser Phe Asp Gly Asp Pro Ala Ser Asn Thr Ala Pro Leu Gln
1               5                   10                  15

Pro

<210> SEQ ID NO 16
<211> LENGTH: 16
<212> TYPE: PRT
<213> ORGANISM: homo sapiens

<400> SEQUENCE: 16

Cys Ala His Tyr Lys Asp Pro Pro Phe Cys Val Ala Arg Cys Pro Ser
1               5                   10                  15

<210> SEQ ID NO 17
<211> LENGTH: 16
<212> TYPE: PRT
<213> ORGANISM: homo sapiens

<400> SEQUENCE: 17

Tyr Gly Leu Gly Met Glu His Leu Arg Glu Val Arg Ala Val Thr Ser
1               5                   10                  15

<210> SEQ ID NO 18
<211> LENGTH: 16
<212> TYPE: PRT
<213> ORGANISM: homo sapiens

<400> SEQUENCE: 18

Leu Gly Ser Gly Leu Ala Leu Ile His His Asn Thr His Leu Cys Phe

```
1               5                   10                  15
```

<210> SEQ ID NO 19
<211> LENGTH: 16
<212> TYPE: PRT
<213> ORGANISM: homo sapiens

<400> SEQUENCE: 19

```
Glu Val Thr Ala Glu Asp Gly Thr Gln Arg Cys Glu Lys Cys Ser Lys
1               5                   10                  15
```

<210> SEQ ID NO 20
<211> LENGTH: 16
<212> TYPE: PRT
<213> ORGANISM: homo sapiens

<400> SEQUENCE: 20

```
Gly Ala Ser Cys Val Thr Ala Cys Pro Tyr Asn Tyr Leu Ser Thr Asp
1               5                   10                  15
```

<210> SEQ ID NO 21
<211> LENGTH: 16
<212> TYPE: PRT
<213> ORGANISM: homo sapiens

<400> SEQUENCE: 21

```
Ala Ala Gly Cys Thr Gly Pro Lys His Ser Asp Cys Leu Ala Cys Leu
1               5                   10                  15
```

<210> SEQ ID NO 22
<211> LENGTH: 16
<212> TYPE: PRT
<213> ORGANISM: homo sapiens

<400> SEQUENCE: 22

```
Leu Glu Glu Ile Thr Gly Tyr Leu Tyr Ile Ser Ala Trp Pro Asp Ser
1               5                   10                  15
```

<210> SEQ ID NO 23
<211> LENGTH: 16
<212> TYPE: PRT
<213> ORGANISM: homo sapiens

<400> SEQUENCE: 23

```
Thr Gln Arg Cys Glu Lys Cys Ser Lys Pro Cys Ala Arg Val Cys Tyr
1               5                   10                  15
```

<210> SEQ ID NO 24
<211> LENGTH: 16
<212> TYPE: PRT
<213> ORGANISM: homo sapiens

<400> SEQUENCE: 24

```
Gly His Cys Trp Gly Pro Gly Pro Thr Gln Cys Val Asn Cys Ser Gln
1               5                   10                  15
```

<210> SEQ ID NO 25
<211> LENGTH: 16
<212> TYPE: PRT
<213> ORGANISM: homo sapiens

<400> SEQUENCE: 25

```
Met Pro Ile Trp Lys Phe Pro Asp Glu Glu Gly Ala Cys Gln Pro Cys
1               5                   10                  15
```

```
<210> SEQ ID NO 26
<211> LENGTH: 16
<212> TYPE: PRT
<213> ORGANISM: homo sapiens

<400> SEQUENCE: 26

Pro Ala Ser Asn Thr Ala Pro Leu Gln Pro Glu Gln Leu Gln Val Phe
1               5                   10                  15

<210> SEQ ID NO 27
<211> LENGTH: 16
<212> TYPE: PRT
<213> ORGANISM: homo sapiens

<400> SEQUENCE: 27

Pro Glu Gly Arg Tyr Thr Phe Gly Ala Ser Cys Val Thr Ala Cys Pro
1               5                   10                  15

<210> SEQ ID NO 28
<211> LENGTH: 16
<212> TYPE: PRT
<213> ORGANISM: homo sapiens

<400> SEQUENCE: 28

Ala Ser Thr Gln Val Cys Thr Gly Thr Asp Met Lys Leu Arg Leu Pro
1               5                   10                  15

<210> SEQ ID NO 29
<211> LENGTH: 16
<212> TYPE: PRT
<213> ORGANISM: homo sapiens

<400> SEQUENCE: 29

Ala Cys His Pro Cys Ser Pro Met Cys Lys Gly Ser Arg Cys Trp Gly
1               5                   10                  15

<210> SEQ ID NO 30
<211> LENGTH: 16
<212> TYPE: PRT
<213> ORGANISM: homo sapiens

<400> SEQUENCE: 30

Gln Asp Thr Ile Leu Trp Lys Asp Ile Phe His Lys Asn Asn Gln Leu
1               5                   10                  15

<210> SEQ ID NO 31
<211> LENGTH: 16
<212> TYPE: PRT
<213> ORGANISM: homo sapiens

<400> SEQUENCE: 31

Gly Pro Glu Ala Asp Gln Cys Val Ala Cys Ala His Tyr Lys Asp Pro
1               5                   10                  15

<210> SEQ ID NO 32
<211> LENGTH: 16
<212> TYPE: PRT
<213> ORGANISM: homo sapiens

<400> SEQUENCE: 32

Ser Arg Cys Trp Gly Glu Ser Ser Glu Asp Cys Gln Ser Leu Thr Arg
1               5                   10                  15

<210> SEQ ID NO 33
```

```
<211> LENGTH: 16
<212> TYPE: PRT
<213> ORGANISM: homo sapiens

<400> SEQUENCE: 33

Pro Ala Ser Pro Glu Thr His Leu Asp Met Leu Arg His Leu Tyr Gln
1               5                   10                  15

<210> SEQ ID NO 34
<211> LENGTH: 16
<212> TYPE: PRT
<213> ORGANISM: homo sapiens

<400> SEQUENCE: 34

Tyr Val Asn Ala Arg His Cys Leu Pro Cys His Pro Glu Cys Gln Pro
1               5                   10                  15

<210> SEQ ID NO 35
<211> LENGTH: 16
<212> TYPE: PRT
<213> ORGANISM: homo sapiens

<400> SEQUENCE: 35

His Ser Asp Cys Leu Ala Cys Leu His Phe Asn His Ser Gly Ile Cys
1               5                   10                  15

<210> SEQ ID NO 36
<211> LENGTH: 16
<212> TYPE: PRT
<213> ORGANISM: homo sapiens

<400> SEQUENCE: 36

Ala Leu Thr Leu Ile Asp Thr Asn Arg Ser Arg Ala Cys His Pro Cys
1               5                   10                  15

<210> SEQ ID NO 37
<211> LENGTH: 16
<212> TYPE: PRT
<213> ORGANISM: homo sapiens

<400> SEQUENCE: 37

Ala Leu Ala Val Leu Asp Asn Gly Asp Pro Leu Asn Asn Thr Thr Pro
1               5                   10                  15

<210> SEQ ID NO 38
<211> LENGTH: 16
<212> TYPE: PRT
<213> ORGANISM: homo sapiens

<400> SEQUENCE: 38

Ala Leu Val Thr Tyr Asn Thr Asp Thr Phe Glu Ser Met Pro Asn Pro
1               5                   10                  15

<210> SEQ ID NO 39
<211> LENGTH: 16
<212> TYPE: PRT
<213> ORGANISM: homo sapiens

<400> SEQUENCE: 39

Arg Cys Lys Gly Pro Leu Pro Thr Asp Cys Cys His Glu Gln Cys Ala
1               5                   10                  15

<210> SEQ ID NO 40
<211> LENGTH: 16
<212> TYPE: PRT
```

<213> ORGANISM: homo sapiens

<400> SEQUENCE: 40

Gln Pro Cys Pro Ile Asn Cys Thr His Ser Cys Val Asp Leu Asp Asp
1               5                   10                  15

<210> SEQ ID NO 41
<211> LENGTH: 16
<212> TYPE: PRT
<213> ORGANISM: homo sapiens

<400> SEQUENCE: 41

Val Ala Arg Cys Pro Ser Gly Val Lys Pro Asp Leu Ser Tyr Met Pro
1               5                   10                  15

<210> SEQ ID NO 42
<211> LENGTH: 16
<212> TYPE: PRT
<213> ORGANISM: homo sapiens

<400> SEQUENCE: 42

Val His Thr Val Pro Trp Asp Gln Leu Phe Arg Asn Pro His Gln Ala
1               5                   10                  15

<210> SEQ ID NO 43
<211> LENGTH: 16
<212> TYPE: PRT
<213> ORGANISM: homo sapiens

<400> SEQUENCE: 43

Tyr Ile Ser Ala Trp Pro Asp Ser Leu Pro Asp Leu Ser Val Phe Gln
1               5                   10                  15

<210> SEQ ID NO 44
<211> LENGTH: 16
<212> TYPE: PRT
<213> ORGANISM: homo sapiens

<400> SEQUENCE: 44

Cys Lys Lys Ile Phe Gly Ser Leu Ala Phe Leu Pro Glu Ser Phe Asp
1               5                   10                  15

<210> SEQ ID NO 45
<211> LENGTH: 16
<212> TYPE: PRT
<213> ORGANISM: homo sapiens

<400> SEQUENCE: 45

Asn Gly Asp Pro Leu Asn Asn Thr Thr Pro Val Thr Gly Ala Ser Pro
1               5                   10                  15

<210> SEQ ID NO 46
<211> LENGTH: 16
<212> TYPE: PRT
<213> ORGANISM: homo sapiens

<400> SEQUENCE: 46

Leu Gln Asp Ile Gln Glu Val Gln Gly Tyr Val Leu Ile Ala His Asn
1               5                   10                  15

<210> SEQ ID NO 47
<211> LENGTH: 16
<212> TYPE: PRT
<213> ORGANISM: homo sapiens

```
<400> SEQUENCE: 47

Val Cys Ala Gly Gly Cys Ala Arg Cys Lys Gly Pro Leu Pro Thr Asp
1               5                   10                  15

<210> SEQ ID NO 48
<211> LENGTH: 16
<212> TYPE: PRT
<213> ORGANISM: homo sapiens

<400> SEQUENCE: 48

His Pro Glu Cys Gln Pro Gln Asn Gly Ser Val Thr Cys Phe Gly Pro
1               5                   10                  15

<210> SEQ ID NO 49
<211> LENGTH: 16
<212> TYPE: PRT
<213> ORGANISM: homo sapiens

<400> SEQUENCE: 49

Gly Val Leu Ile Gln Arg Asn Pro Gln Leu Cys Tyr Gln Asp Thr Ile
1               5                   10                  15

<210> SEQ ID NO 50
<211> LENGTH: 16
<212> TYPE: PRT
<213> ORGANISM: homo sapiens

<400> SEQUENCE: 50

Leu Gln Val Ile Arg Gly Arg Ile Leu His Asn Gly Ala Tyr Ser Leu
1               5                   10                  15

<210> SEQ ID NO 51
<211> LENGTH: 16
<212> TYPE: PRT
<213> ORGANISM: homo sapiens

<400> SEQUENCE: 51

Glu Ser Phe Asp Gly Asp Pro Ala Ser Asn Thr Ala Pro Leu Gln Pro
1               5                   10                  15

<210> SEQ ID NO 52
<211> LENGTH: 16
<212> TYPE: PRT
<213> ORGANISM: homo sapiens

<400> SEQUENCE: 52

Ala Cys Pro Tyr Asn Tyr Leu Ser Thr Asp Val Gly Ser Cys Thr Leu
1               5                   10                  15

<210> SEQ ID NO 53
<211> LENGTH: 16
<212> TYPE: PRT
<213> ORGANISM: homo sapiens

<400> SEQUENCE: 53

Pro Val Thr Gly Ala Ser Pro Gly Gly Leu Arg Glu Leu Gln Leu Arg
1               5                   10                  15

<210> SEQ ID NO 54
<211> LENGTH: 16
<212> TYPE: PRT
<213> ORGANISM: homo sapiens

<400> SEQUENCE: 54
```

Cys Val Asp Leu Asp Asp Lys Gly Cys Pro Ala Glu Gln Arg Ala Ser
1               5                   10                  15

<210> SEQ ID NO 55
<211> LENGTH: 16
<212> TYPE: PRT
<213> ORGANISM: homo sapiens

<400> SEQUENCE: 55

Asn His Ser Gly Ile Cys Glu Leu His Cys Pro Ala Leu Val Thr Tyr
1               5                   10                  15

<210> SEQ ID NO 56
<211> LENGTH: 16
<212> TYPE: PRT
<213> ORGANISM: homo sapiens

<400> SEQUENCE: 56

Gly Ser Val Thr Cys Phe Gly Pro Glu Ala Asp Gln Cys Val Ala Cys
1               5                   10                  15

<210> SEQ ID NO 57
<211> LENGTH: 16
<212> TYPE: PRT
<213> ORGANISM: homo sapiens

<400> SEQUENCE: 57

Trp Gly Leu Leu Leu Ala Leu Leu Pro Pro Gly Ala Ala Ser Thr Gln
1               5                   10                  15

<210> SEQ ID NO 58
<211> LENGTH: 16
<212> TYPE: PRT
<213> ORGANISM: homo sapiens

<400> SEQUENCE: 58

Phe Leu Arg Gly Gln Glu Cys Val Glu Glu Cys Arg Val Leu Gln Gly
1               5                   10                  15

<210> SEQ ID NO 59
<211> LENGTH: 16
<212> TYPE: PRT
<213> ORGANISM: homo sapiens

<400> SEQUENCE: 59

Gly Thr Gln Leu Phe Glu Asp Asn Tyr Ala Leu Ala Val Leu Asp Asn
1               5                   10                  15

<210> SEQ ID NO 60
<211> LENGTH: 16
<212> TYPE: PRT
<213> ORGANISM: homo sapiens

<400> SEQUENCE: 60

Gly Val Lys Pro Asp Leu Ser Tyr Met Pro Ile Trp Lys Phe Pro Asp
1               5                   10                  15

<210> SEQ ID NO 61
<211> LENGTH: 535
<212> TYPE: PRT
<213> ORGANISM: Corynebacterium diphtheriae

<400> SEQUENCE: 61

Gly Ala Asp Asp Val Val Asp Ser Ser Lys Ser Phe Val Met Glu Asn
1               5                   10                  15

```
Phe Ser Ser Tyr His Gly Thr Lys Pro Gly Tyr Val Asp Ser Ile Gln
             20                  25                  30

Lys Gly Ile Gln Lys Pro Lys Ser Gly Thr Gln Gly Asn Tyr Asp Asp
             35                  40                  45

Asp Trp Lys Glu Phe Tyr Ser Thr Asp Asn Lys Tyr Asp Ala Ala Gly
 50                  55                  60

Tyr Ser Val Asp Asn Glu Asn Pro Leu Ser Gly Lys Ala Gly Gly Val
 65                  70                  75                  80

Val Lys Val Thr Tyr Pro Gly Leu Thr Lys Val Leu Ala Leu Lys Val
             85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Lys Arg Phe Gly
            115                 120                 125

Asp Gly Ala Ser Arg Val Val Leu Ser Leu Pro Phe Ala Glu Gly Ser
130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
            165                 170                 175

Ala Met Tyr Glu Tyr Met Ala Gln Ala Cys Ala Gly Asn Arg Val Arg
            180                 185                 190

Arg Ser Val Gly Ser Ser Leu Ser Cys Ile Asn Leu Asp Trp Asp Val
            195                 200                 205

Ile Arg Asp Lys Thr Lys Thr Lys Ile Glu Ser Leu Lys Glu His Gly
            210                 215                 220

Pro Ile Lys Asn Lys Met Ser Glu Ser Pro Asn Lys Thr Val Ser Glu
225                 230                 235                 240

Glu Lys Ala Lys Gln Tyr Leu Glu Glu Phe His Gln Thr Ala Leu Glu
            245                 250                 255

His Pro Glu Leu Ser Glu Leu Lys Thr Val Thr Gly Thr Asn Pro Val
            260                 265                 270

Phe Ala Gly Ala Asn Tyr Ala Ala Trp Ala Val Asn Val Ala Gln Val
            275                 280                 285

Ile Asp Ser Glu Thr Ala Asp Asn Leu Glu Lys Thr Thr Ala Ala Leu
290                 295                 300

Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
            325                 330                 335

Ser Leu Met Val Ala Gln Ala Ile Pro Leu Val Gly Glu Leu Val Asp
            340                 345                 350

Ile Gly Phe Ala Ala Tyr Asn Phe Val Glu Ser Ile Ile Asn Leu Phe
            355                 360                 365

Gln Val Val His Asn Ser Tyr Asn Arg Pro Ala Tyr Ser Pro Gly His
            370                 375                 380

Lys Thr Gln Pro Phe Leu His Asp Gly Tyr Ala Val Ser Trp Asn Thr
385                 390                 395                 400

Val Glu Asp Ser Ile Ile Arg Thr Gly Phe Gln Gly Glu Ser Gly His
            405                 410                 415

Asp Ile Lys Ile Thr Ala Glu Asn Thr Pro Leu Pro Ile Ala Gly Val
            420                 425                 430
```

```
Leu Leu Pro Thr Ile Pro Gly Lys Leu Asp Val Asn Lys Ser Lys Thr
        435                 440                 445

His Ile Ser Val Asn Gly Arg Lys Ile Arg Met Arg Cys Arg Ala Ile
    450                 455                 460

Asp Gly Asp Val Thr Phe Cys Arg Pro Lys Ser Pro Val Tyr Val Gly
465                 470                 475                 480

Asn Gly Val His Ala Asn Leu His Val Ala Phe His Arg Ser Ser Ser
                485                 490                 495

Glu Lys Ile His Ser Asn Glu Ile Ser Ser Asp Ser Ile Gly Val Leu
            500                 505                 510

Gly Tyr Gln Lys Thr Val Asp His Thr Lys Val Asn Ser Lys Leu Ser
        515                 520                 525

Leu Phe Phe Glu Ile Lys Ser
        530             535

<210> SEQ ID NO 62
<211> LENGTH: 6
<212> TYPE: PRT
<213> ORGANISM: homo sapiens

<400> SEQUENCE: 62

Gly Gly Gly Gly Gly Cys
1               5
```

VACCINE COMPOSITION AND USES THEREOF

CROSS-REFERENCE TO RELATED APPLICATIONS

This application is the U.S. National Stage, pursuant to 35 U.S.C. § 371, of International Application No. PCT/AU2016/050275, filed Apr. 15, 2016, designating the United States and published on Oct. 20, 2016 as Publication WO 2016/164980, which claims the benefit of Australian Application No. 2015901375, filed Apr. 17, 2015, the entire contents of which are incorporated herein by reference.

TECHNICAL FIELD

The present invention relates generally to a vaccine composition comprising fragments of the cancer-related protein Her2/neu, methods of preparing such composition, and uses thereof for the prevention or treatment of a cancer characterized by the expression or over-expression of the Her2/neu protein.

BACKGROUND

The Her2/neu tumor antigen, encoded by the erbB2/neu protooncogene, is a 185 kDa protein that belongs to the human epidermal growth factor receptor family. It consists of a cysteine-rich extracellular domain (ECD, from amino acids 23 to 652) with several glycosylation sites, a hydrophobic transmembrane domain (from amino acids 653 to 675) and an intracellular tyrosine kinase domain (from amino acids 676 to 1255). The Her2/neu receptor is expressed on the cell membrane of a variety of epithelial cell types and regulates aspects of cell growth and division through binding of specific growth factors.

Her2/neu is expressed at low levels in many normal cells, but is over-expressed in a variety of cancers, including breast, ovarian, endometrial, gastric, pancreatic, prostate and salivary gland cancers. For example, approximately 30% of metastatic breast cancers have been shown to over-express Her2/neu. This over-expression is associated with a poor prognosis for the breast cancer patient, as it corresponds to decreased relapse-free periods and shortened survival time. Currently, the most common forms of treating breast cancer involve surgery, chemical intervention and/or radiotherapy. Unless the cancer is restricted to a defined area, surgery alone cannot eliminate the cancer. Moreover, radiation treatment as well as chemotherapy may entail severe negative side effects.

In view of the disadvantages associated with the current therapies, attempts have been made to find additional approaches for treating proliferative disorders such as breast cancer, including immunotherapy.

The clinical implications of Her2/neu over-expression in tumors have made Her2/neu an attractive target for antibody-mediated immunotherapy, alone or as an adjunct to conventional chemotherapy. For example, the monoclonal antibody (mAb) 4D5 has been shown to reduce the growth of Her2/neu expressing tumours in mice by direct and indirect mechanisms such as apoptosis, antibody-dependent cell-mediated cytotoxicity (ADCC) or complement-dependent cytotoxicity (CDC). Based on these results, a humanized form of this antibody, Trastuzumab (Herceptin®), was tested in clinical trials. Increased overall survival of patients with breast tumors overexpressing Her2/neu was observed following cytotoxic treatment plus Herceptin®, as compared to chemotherapy or Trastuzumab alone. Herceptin® is now used as monotherapy but shows even higher efficacy in combination with cytotoxic chemotherapy. It is to be noted, however, that Trastuzumab is generally only effective in breast cancer where the Her2/neu receptor is over-expressed. Furthermore, multiple infusions are typically required, resulting in high treatment costs.

An alternative approach to the treatment or prevention of Her2/neu-associated cancers using passive immunotherapy with monoclonal antibodies such as Trastuzumab is based on the induction of tumour-specific humoral and/or cellular immune responses and the identification of antigens recognized by human B- and T-lymphocytes. For example, numerous antibodies directed against the extracellular domain (ECD) of Her2/neu have been generated by immunizing mice with cells expressing Her2/neu. The biological effect of these antibodies appears to be epitope-specific; that is, it is based on specific recognition of a short subsequence within the Her2/neu ECD. However, some antibodies have no effect or even actively stimulate tumour growth.

Such vaccine immunotherapy for cancer has been based on antigens against which humoral and/or cellular responses are elicited. These antigens should ideally be expressed or over-expressed exclusively by tumour cells, often referred to as tumour-associated antigens (TAAs). One of the first TAAs described for breast cancer was Her2/neu. Meanwhile, various TAAs representing different epitopes have been tested, but so far none have successfully made their way into clinical practice.

Depending on the type of immune response intended (i.e., B cell or T cell response), different strategies are typically applied. For instance, to induce a B cell (i.e. antibody) response, the antigens should comprise a B cell epitope. As generally understood in the art, a B cell epitope is a part of an antigen that is recognized and bound by a B cell receptor. Lipids, polysaccharides and proteins/peptides may contain B cell epitopes which, upon introduction into an organism of choice, cause B cells to produce antibodies which specifically bind to the introduced epitope.

Individual fragments of the ECD of Her2/neu, including B cell epitopes, are known in the art. For example, WO 2002/068474 describes a vaccine that comprises a peptide of 9-25 amino acids which sequence occurs in the extracellular part of the Her2/neu protein. Further, WO 2007/118660 describes a multi-peptide vaccine comprising a specific combination of peptides presenting different amino acid sequences as occur in the extracellular part of the Her2/neu protein. These peptides may be administered individually or in combination, in the form of multiple discrete peptides, each preferably conjugated separately to a delivery system. In yet another example, WO 2011/020604 describes fusion peptides comprising multiple Her2/neu B cell epitopes coupled to a virosome delivery system. These virosomes were shown to a induce a higher antibody titre against a single B cell epitope as compared to the same fusion peptides formulated with Montanide™ or an ISCOM-based delivery system.

Despite several attempts to develop a suitable vaccine for inducing immunity against Her2/neu, there is still no effective vaccine in clinical use. It is an aim of the present invention to provide an improve composition suitable for use as a vaccine for treating or preventing a condition such as cancer that is characterized by the expression or over-expression of Her2/neu.

SUMMARY OF THE INVENTION

The present specification described a vaccine composition comprising:
(i) an adjuvant; and
(ii) at least one fusion peptide conjugated to a carrier protein,
wherein the carrier protein is the diphtheria toxin variant CRM-197 (GenBank Accession No. 1007216A; SEQ ID NO:61) and wherein the at least one fusion peptide comprises two or more non-contiguous B cell epitopes of Her2/neu selected from the group consisting of SEQ ID Nos:1-7 and 15-60 and amino acid sequences that have at least 85% identity to any of the foregoing.

The present specification also describes a pharmaceutical composition comprising the vaccine composition as herein described and a pharmaceutically acceptable carrier.

The present specification also describes a method of treating or preventing a cancer characterized by expression or over-expression of Her2/neu in a patient in need thereof, the method comprising the step of administering to said patient an effective amount of the vaccine composition as herein described or the pharmaceutical composition as herein described.

The present specification also describes use of the vaccine composition as herein described in the manufacture of a medicament for treating or preventing a cancer characterized by expression or over-expression of Her2/neu in a patient in need thereof.

The present specification also discloses the vaccine composition or pharmaceutical composition as herein described for use in treating or preventing a cancer characterized by expression or over-expression of Her2/neu in a patient in need thereof.

DETAILED DESCRIPTION

Figure 1:
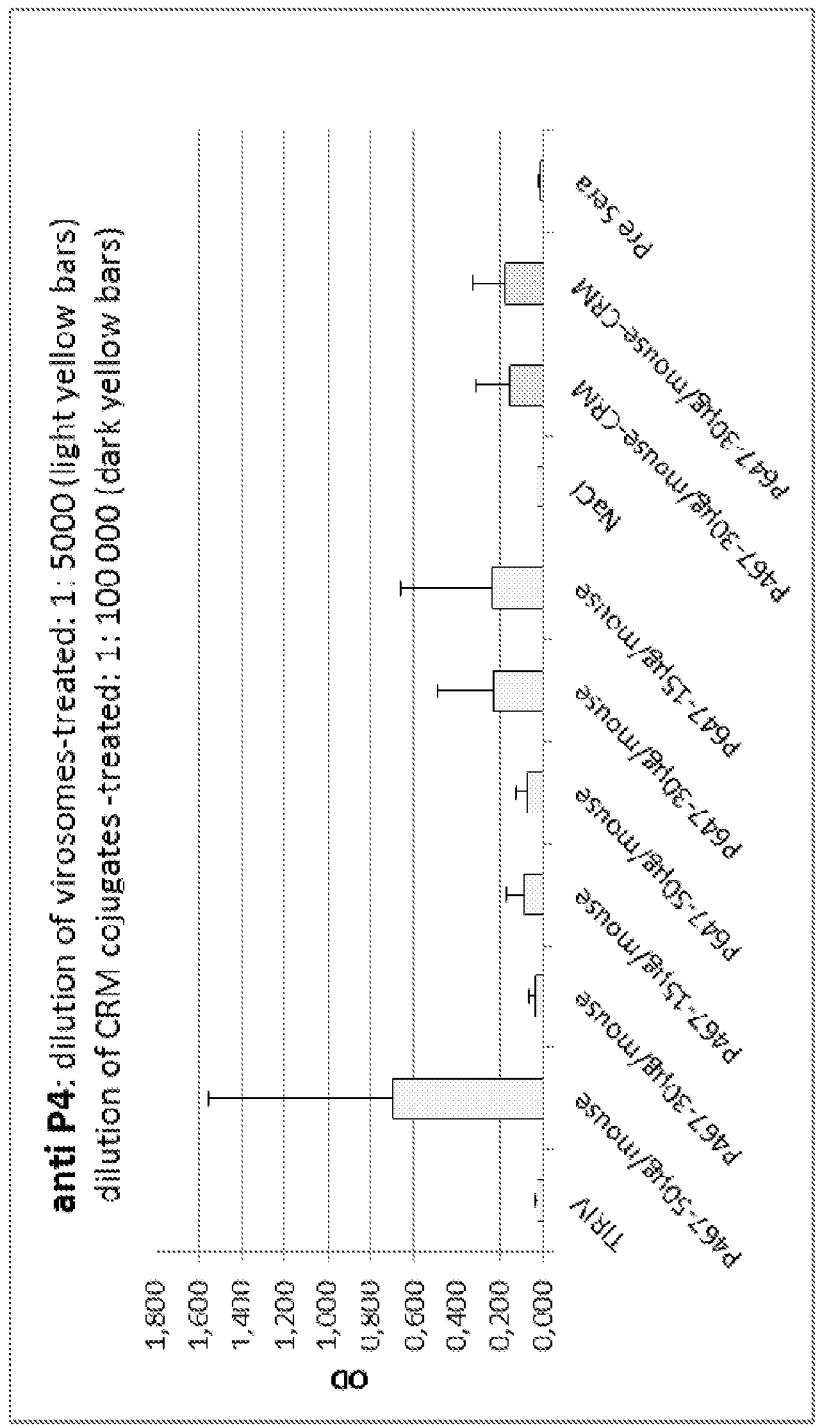
FIG. 1 shows anti-P4 antibody titres in serum samples obtained after the fourth immunisation with either virosomes incorporating the P467 or P647 fusion peptides or CRM197-fusion protein conjugates (CRM). Data are presented as OD values.

The terminology used herein is for the purpose of describing particular embodiments only and is not intended to be limiting. Unless defined otherwise, all technical and scientific terms used herein have the same meanings as commonly understood by one of ordinary skill in the art to which the present disclosure belongs. Any materials and methods similar or equivalent to those described herein can be used to practice the present invention. Practitioners may refer to Sambrook et al., (1989) Molecular Cloning: A Laboratory Manual, 2nd ed., Cold Spring Harbor Press, Plainsview, N.Y., and Ausubel et al. (1999) Current Protocols in Molecular Biology (Supplement 47), John Wiley & Sons, New York, Murphy et al. (1995) Virus Taxonomy Springer Verlag:79-87, for definitions and terms of the art and other methods known to the person skilled in the art.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

By "consisting of" is meant including, and limited to, whatever follows the phrase "consisting of". Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

As used herein the singular forms "a", "an" and "the" include plural aspects unless the context clearly dictates otherwise. Thus, for example, reference to "a cell" includes a single cell, as well as two or more cells; reference to "an organism" includes one organism, as well as two or more organism; and so forth.

Nucleotide and amino acid sequences are referred to by sequence identifier numbers (SEQ ID NO:). The SEQ ID NOs: correspond numerically to the sequence identifiers <400>1, <400>2, etc. A summary of sequence identifiers is provided herein.

The present disclosure is predicated, at least in part, on the inventors' surprising finding that a vaccine composition comprising (i) an adjuvant and (ii) a fusion peptide of multiple B cell epitopes derived from the extracellular domain (ECD) of Her2/neu conjugated to the non-toxic diphtheria toxin variant CRM-197 (GenBank Accession No. 1007216A), can elicit an antigen-specific antibody response that is far superior to that achievable by using a delivery system such as virosomes.

Thus, in one aspect, there is provided a vaccine composition comprising:

(i) an adjuvant; and
(ii) at least one fusion peptide conjugated to a carrier protein, wherein the carrier protein is the diphtheria toxin variant CRM-197 (GenBank Accession No. 1007216A; SEQ ID NO:61) and wherein the at least one fusion peptide comprises two or more non-contiguous B cell epitopes of Her2/neu selected from the group consisting of SEQ ID Nos:1-7 and 15-60 and amino acid sequences that have at least 85% identity to any of the foregoing.

B Cell Epitopes

As used herein, the term "B cell epitope" refers to a part of a molecule that is recognized by a B cell receptor (antibody). Thus, a "B cell epitope" is to be understood as being a small subsequence of an antigen, said epitope subsequence capable of being recognized by an antibody. An antigen may contain multiple B cell epitopes, and therefore may be bound by multiple distinct antibodies, but any given epitopic fragment of this antigen will typically be bound by only one antibody.

As used herein, the terms "peptide" and "polypeptide" are used in their broadest sense to refer to a molecule of two or more amino acid residues, or amino acid analogs. The amino acid residues may be linked by peptide bonds, or alternatively by other bonds, e.g. ester, ether etc., but in most cases will be linked by peptide bonds.

As used herein, the terms "amino acid" or "amino acid residue" encompass both natural and unnatural or synthetic amino acids, including both the D- or L-forms, and amino acid analogs. An "amino acid analog" is to be understood as a non-naturally occurring amino acid differing from its corresponding naturally occurring amino acid at one or more atoms. For example, an amino acid analog of cysteine may be homocysteine.

Persons skilled in the art will know how to determine whether or not a peptide is a B cell epitope of Her2/neu. In an illustrative example, a peptide may be identified with a high degree of accuracy as being, or comprising, a B cell epitope by using established computer programs that compare the sequence of the peptide in question with a database of known sequences and/or partial sequences known to be recognized by antibodies encoded by the human or mouse germline. Alternatively, a B cell epitope within a given peptide or polypeptide may be identified by computer-aided analysis using various combinations of correlates of antigenicity such as surface accessibility, chain flexibility, hydropathy/hydrophilicity profiles, predicted secondary structure, etc. Alternatively, a peptide in question may be identified as being, or comprising, a B cell epitope by immunizing an animal with the peptide in question at least once, allowing an immune response to mount and then testing the serum of the animal for antibodies that specifically bind to at least a part of the administered peptide using, for example, an enzyme linked immunosorbant assay (ELISA), a radioimmunoassay, a Western blot analysis or a spot-blot analysis. A more detailed description of how to determine whether or not a peptide in question is a B cell epitope is provided herein below in Examples 6 and 7.

Table 1, below, sets out the amino acid sequences of the B cell epitopes of the extracellular domain of Her2/neu, including derivatives thereof:

TABLE 1

| B cell epitope | SEQ ID NO: |
|---|---|
| RVLQGLPREYVNARHS | 1 |
| YMPIWKFPDEEGAC | 2 |
| PESFDGDPASNTAPLQP | 3 |
| PESFDGDPASNTAPLQPGGGGC | 4 |
| RVLQGLPREYVNARHC | 5 |
| PESFDGDPASNTAPLQP | 15 |
| CAHYKDPPFCVARCPS | 16 |
| YGLGMEHLREVRAVTS | 17 |
| LGSGLALIHHNTHLCF | 18 |
| EVTAEDGTQRCEKCSK | 19 |
| GASCVTACPYNYLSTD | 20 |
| AAGCTGPKHSDCLACL | 21 |
| LEEITGYLYISAWPDS | 22 |
| TQRCEKCSKPCARVCY | 23 |
| GHCWGPGPTQCVNCSQ | 24 |
| MPIWKFPDEEGACQPC | 25 |
| PASNTAPLQPEQLQVF | 26 |
| PEGRYTFGASCVTACP | 27 |
| ASTQVCTGTDMKLRLP | 28 |
| ACHPCSPMCKGSRCWG | 29 |
| QDTILWKDIFHKNNQL | 30 |
| GPEADQCVACAHYKDP | 31 |
| SRCWGESSEDCQSLTR | 32 |
| PASPETHLDMLRHLYQ | 33 |
| YVNARHCLPCHPECQP | 34 |
| HSDCLACLHFNHSGIC | 35 |
| ALTLIDTNRSRACHPC | 36 |
| ALAVLDNGDPLNNTTP | 37 |
| ALVTYNTDTFESMPNP | 38 |
| RCKGPLPTDCCHEQCA | 39 |
| QPCPINCTHSCVDLDD | 40 |
| VARCPSGVKPDLSYMP | 41 |
| VHTVPWDQLFRNPHQA | 42 |
| YISAWPDSLPDLSVFQ | 43 |
| CKKIFGSLAFLPESFD | 44 |
| NGDPLNNTTPVTGASP | 45 |
| LQDIQEVQGYVLIAHN | 46 |
| VCAGGCARCKGPLPTD | 47 |
| HPECQPQNGSVTCFGP | 48 |

TABLE 1-continued

| B cell epitope | SEQ ID NO: |
|---|---|
| GVLIQRNPQLCYQDTI | 49 |
| LQVIRGRILHNGAYSL | 50 |
| ESFDGDPASNTAPLQP | 51 |
| ACPYNYLSTDVGSCTL | 52 |
| PVTGASPGGLRELQLR | 53 |
| CVDLDDKGCPAEQRAS | 54 |
| NHSGICELHCPALVTY | 55 |
| GSVTCFGPEADQCVAC | 56 |
| WGLLLALLPPGAASTQ | 57 |
| FLRGQECVEECRVLQG | 58 |
| GTQLFEDNYALAVLDN | 59 |
| GVKPDLSYMPIWKFPD | 60 |

In an embodiment disclosed herein, the two or more B cell epitopes are selected from the group consisting of SEQ ID Nos:1-7 and 15-60, as shown in Table 1 and 2, and amino acid sequences that have at least 859 identity to any of the foregoing (i.e., that have at least 85% sequence identity to any one of SEQ ID Nos:1-7 and 15-60). In another embodiment disclosed herein, the two or more B cell epitopes are selected from the group consisting of SEQ ID Nos:1-7 and amino acid sequences that have at least 85% identity to any of the foregoing; that is, that have at least 85% sequence identity to any one of SEQ ID Nos:1-7. It is to be noted that none of these B cell epitopes are contiguous in native Her2/neu.

Amino acid sequences that have at least 85% sequence identity to any one of SEQ ID Nos:1-7 and 15-60 include derivatives that result from substituting at least one amino acid in a native (i.e. naturally occurring) B cell epitope of the Her2/neu ECD with another amino acid not present at that position of Her2/neu such that the amino acid substitution remains conservative. Derivatives may be made in order to increase the stability of the fusion peptide in the intermediate and/or end products or to increase the solubility of the fusion peptide in the intermediate and/or end products or to increase the immunogenicity of fusion peptides. Methods for preparing suitable derivatives will be known to persons skilled in the art. Illustrative examples include the synthesis of derivatives or its recombinant production using a mutated nucleic acid molecule. Further, a derivative will typically retain its quality as a B cell epitope as described elsewhere herein. Thus, also disclosed herein are "functional" derivatives in which an amino acid substitution to the native sequence does not, or does not completely, abolish the capacity of the derivative to function as a B cell epitope.

The identification of additional or optimized immunostimulatory fusion peptides may also include the step of comparing the stimulation of B cells by the fusion peptide and the stimulation of B cells by the derivative as a determination of the effectiveness of the stimulation of immune effector cells by the derivative. By comparing the derivative with a known fusion peptide, peptides with increased immune cell stimulatory properties can be prepared.

As used herein, a "conservative substitution" refers to changing amino acid identity at a given position to replace with an amino acid of approximately equivalent size, charge and/or polarity. Examples of natural conservative substitutions of amino acids include the following 8 substitution groups (designated by the conventional one-letter code): (1) M, I, L, V; (2) F, Y. W; (3) K, R, (4) A, G; (5) S, T; (6) Q, N; (7) E, D; and (8) C, S.

A derivative may also result from amino acid substitutions which are functionally equivalent. As used herein, these are to be understood as amino acid substitutions which, when effected, result in a fusion peptide which will give an identical or comparable (e.g., within 10%) ELISA reading based on serum from an animal to which the fusion peptide comprising a derivatized epitopic fragment or derivatized epitopic fragments has/have been administered, as compared to a fusion peptide without corresponding derivatizations. The antigenicity of a fusion peptide may, for example, be determined by measuring the titre of antibodies elicited by immunisation of animals by ELISA, as is described, for example, in Examples 6 and 7. An analogous process can be used to assay for the functional equivalence of an amino acid substitution, conservative or otherwise. For example, the immune response elicited by a fusion peptide comprising a non-derivatized, "parental" fragment is compared-using the same assay—to that elicited by a fusion peptide comprising the derivatized fragment. If the immune response elicited by the fusion peptide comprising the derivatized fragment is as strong as that elicited by the fusion peptide with the non-derivatized fragment, then the amino acid substitution can be regarded as functionally equivalent. If the derivatized immune response is superior to the non-derivatized one, then the amino acid substitution can be regarded as improved.

As used herein, the terms "native" and "natural" refer to the form of a molecule as normally occurring in nature. As such, the "native" sequence of the ECD of Her2/neu refers to amino acid residues 23-652 of the previously published Her2/neu amino acid sequence (Swiss-Prot database accession number P04626; ERBB2_HUMAN). Conversely, a "non-native" sequence, including a "non-native linker" is any amino acid sequence not belonging to native sequence of the ECD of Her2/neu. Thus, in an embodiment disclosed herein, a peptidic "non-native linker" does not represent an extension of either of the Her2/neu fragments to which it connects into the adjoining native sequence of Her2/neu.

Fusion Peptides

The design of immunopreventive and/or immunotherapeutic vaccine compositions for Her2/neu-expressing or Her2/neu-over-expressing cancers based on multiple epitopes/peptides has entailed administration of such peptides as discrete (i.e., separate) peptides. This has certain implied disadvantages. For example, simultaneous administration of multiple peptides within the same composition runs the risk that these peptides will aggregate, thereby decreasing their intended availability to the host immune system. In extreme cases, the solubility of such aggregates may decrease such that the aggregates precipitate, becoming unavailable to the host immune system. At the same time, separate administration of such peptides in different solutions and at different time points decreases the likelihood that the immunogenic effects of such peptides may combine in an advantageous manner.

Further difficulties arise when multiple single epitopes are used with certain types of delivery systems, such as virosomes, liposomes or virus-like particles (VLPs). To allow reproducible vaccine production, it is advantageous to present the epitopes in defined concentrations. However, when coupling (i.e. covalently associating) multiple peptide fragments to a single delivery system, such as a virosome or liposome, it is difficult to ensure that the same number of epitopes is coupled to each delivery system. Fluctuations in coupling number per delivery system invariably exist. While one can be relatively certain that each viable delivery system will be coupled to, say, each of epitopes A and B, some delivery systems will be associated with slightly more of epitope A than intended, while epitope B will slightly exceed intended amounts in others. While the Gaussian distribution of epitopes A and B will tend to center on the intended ratio of fragments A:B, any Gaussian distribution by definition contains outliers, and it is these outliers which potentially detract from maximal immunogenic efficacy, and which become increasingly costly and laborious to exclude as the requirements for maintaining the intended epitope ratio in the delivery system become more stringent. Similar concerns apply when combining delivery systems such as virosomes associated with different epitope fragments in an attempt to realize a desired ratio of one Her2/neu ECD fragment to another.

Disclosed herein is an approach that overcomes or at least partially alleviates the above disadvantages. By linking at least two non-contiguous B cell epitopes from the ECD of Her2/neu, or derivatives thereof, in a single fusion peptide, a homogeneous formulation can be achieved in which only one kind of fusion peptide is present. The elements of the fusion peptide (i.e. the epitopes of the ECD of Her2/neu which in the native ECD are non-contiguous) are the same in every peptide, and can be chosen (or chosen and modified) such that undesired intra- and inter-polypeptide interactions are minimized.

In an embodiment described herein, the vaccine composition will comprise a single type of fusion peptide. Accordingly, the ratio of B cell epitopes present is ultimately dictated by the ratio of these fragments in the fusion peptide. This means that any desired ratio for eliciting an immunogenic response can be easily and reliably fixed at the level of fusion peptide construction and design.

Finally, when using the non-toxic diphtheria toxin variant CRM-197 as the carrier protein to deliver the fusion peptides described herein, variability relating to the relative distribution of each Her2/neu B cell epitope in the vaccine composition can be minimised or avoided because the ratio of one Her2/neu B cell epitope to any other natively non-contiguous B cell epitope thereof will remain constant regardless of how many fusion peptides are bound to the carrier protein since, as mentioned above, this ratio is determined at the level of a single fusion peptide.

In other embodiments disclosed herein, the vaccine composition will comprise more than one type of fusion peptide.

The vaccine composition disclosed herein elicits an antigen-specific antibody response in a host to which it is administered. Surprisingly, the antigen-specific response that is elicited by the vaccine composition is orders of magnitude greater that the immune response obtainable using Her2/neu B cell epitopes individually or using alternative delivery systems such as virosomes. Thus, the present invention avoids or at least minimises the drawbacks of complex manufacturing processes for incorporating peptides into virosomes, the variability that is often associated with trying to incorporate multiple individual peptides into a delivery system and the possible adverse interactions between separate B cell epitope fragments that could degrade the efficacy of the resulting vaccine composition.

As used herein, the term "fusion peptide" refers to a non-native peptide composed of two or more non-contiguous B cell epitopes of the ECD of Her2/neu (e.g, 2, 3, 4, 5, 6, 7, 8, 9, 10, 11 or more non-contiguous B cell epitopes of the ECD of Her2/neu), linked to one another, e.g. via peptide (amide) bonds. In an embodiment disclosed herein, the two or more B cell epitopes of the ECD of Her2/neu are non-contiguous in their native state; that is, in the ECD of native Her2/neu.

In an embodiment disclosed herein, the fusion peptide comprises at least three non-contiguous B cell epitopes of the ECD of Her2/neu. In an embodiment, the fusion peptide comprises an amino acid sequence selected from the group consisting of SEQ ID NOs: 8-14 and amino acid sequences that have at least 85% identity to any of the foregoing.

Table 2, below, provides a list of selected B cell epitopes, as well as fusion peptides according to some of the embodiments disclosed herein:

TABLE 2

| Peptide/ Fragment | Amino acid sequence | SEQ ID NO: |
|---|---|---|
| P6 | RVLQGLPREYVNARHS | 1 |
| P7 | YMPIWKFPDEEGAC | 2 |
| P4 | PESFDGDPASNTAPLQP | 3 |
| P3 | PESFDGDPASNTAPLQPGGGGGC | 4 |
| P5 | RVLQGLPREYVNARHC | 5 |
| P8 | YMPIWKFPDEEGAS | 6 |
| P9 | PESFDGDPASNTAPLQPC | 7 |
| P467 | PESFDGDPASNTAPLQPRVLQGLPREYVNARHSLP YMPIWKFPDEEGAC | 8 |
| P647 | RVLQGLPREYVNARHSPESFDGDPASNTAPLQPYM PIWKFPDEEGAC | 9 |
| P467B | PESFDGDPASNTAPLQPRVLQGLPREYVNARHSYM PIWKFPDEEGAC | 10 |
| P485 | PESFDGDPASNTAPLQPYMPIWKFPDEEGASRVLQ GLPREYVNARHC | 11 |
| P689 | RVLQGLPREYVNARHSYMPIWKFPDEEGASPESFD GDPASNTAPLQPC | 12 |
| P845 | YMPIWKFPDEEGASPESFDGDPASNTAPLQPRVLQ GLPREYVNARHC | 13 |
| P869 | YMPIWKFPDEEGASRVLQGLPREYVNARHSPESFD GDPASNTAPLQPC | 14 |

In an embodiment disclosed herein, the fusion peptide comprises an amino acid sequence of SEQ ID NO: 8 (designated fusion peptide P467) or SEQ ID NO:9 (designated fusion peptide P647) or an amino acid sequence that has at least 85% identity to SEQ ID NO: 8 or SEQ ID NO:9, as shown in Table 2, above.

Also contemplated herein are fusion peptides comprising two or more B cell epitopes of the ECD of Her2/neu selected from the group consisting of SEQ ID NOs: 1-7 and 15-60, or amino acid sequences that have at least 85% identity to any of the foregoing, concatenated two or more times in tandem repeat. For example, fusion peptides contemplated herein may comprise two or more tandem repeats of SEQ ID NO: 1, two or more tandem repeats of SEQ ID NO:2, two or more tandem repeats of SEQ ID NO:3, two or more tandem repeats of SEQ ID NO:4, two or more tandem repeats of SEQ ID NO:5, and so on. It will be understood, however, that incorporating two or more different B cell epitopes into the fusion peptide is more likely to generate a more beneficial immune response by eliciting antibodies that specifically recognise multiple B cell epitopes of the ECD of Her2/neu. Thus, in an embodiment disclosed herein, the fusion peptide comprises at least two different B cell epitopes of the ECD of Her2/neu selected from the group consisting of SEQ ID NOs: 1-7 and 15-60, or amino acid sequences that have at least 85% identity to any of the foregoing.

In an embodiment disclosed herein, the fusion peptide consists of an amino acid sequence selected from the group consisting of SEQ ID NOs: 8-14. In yet another embodiment, the fusion peptide consists of an amino acid sequence of SEQ ID NO: 8 (designated fusion peptide P467) or SEQ ID NO:9 (designated fusion peptide P647).

In the individual B cell epitopes of SEQ ID NOs:3 and 4, as set out above in Table 2, SEQ ID NO:4 comprises an additional C-terminal linker ending in Cys (i.e., GGGGGC; SEQ ID NO: 62 not found in, SEQ ID NO:3. This C-terminal linker in SEQ ID NO:4 itself ends in Cys, which allows this single epitope to be coupled to the carrier protein, as illustrated in some of the Examples set out hereinbelow. When used as part of the fusion peptide of the invention, the B cell epitope of SEQ ID NO:4 is present in this fusion peptide in the form of SEQ ID NO:3. In the experiments in which the B cell epitope of SEQ ID NO:4 is employed it is the portion of SEQ ID NO:4 corresponding to SEQ ID NO:3 that functions as the B cell epitope.

Suitable methods of preparing a fusion peptide as herein described would be familiar to persons skilled in the art. An illustrative example includes peptide synthesis that involves the sequential formation of peptide bonds linking each B cell epitope to its respectively neighboring B cell epitope, as described elsewhere herein, and recovering said fusion peptide. Suitable peptide synthesis methods will be known in the art. Illustrative examples include the methods described in "Amino Acid and Peptide Synthesis" (Oxford Chemistry Primers; by John Jones, Oxford University Press). Synthetic peptides can also be made by liquid-phase synthesis or solid-phase peptide synthesis (SPPS) on different solid supports (e.g. polystyrene, polyamide, or PEG). SPPS may incorporate the use of F-moc (9H-fluoren-9-ylmethoxycarbonyl) or t-Boc (tert-Butoxycarbonyl). Custom peptides are also available from a number of commercial manufacturers.

Alternatively, the fusion peptide may be prepared by recombinant methodology. For example, a nucleic acid molecule comprising a nucleic acid sequence encoding the fusion peptide can be transfecting into a suitable host cell capable of expressing said nucleic acid sequence, incubating said host cell under conditions suitable for the expression of said nucleic acid sequence, and recovering said fusion peptide. Suitable methods for preparing a nucleic acid molecule encoding the fusion peptide(s) of interest will also be known to persons skilled in the art, based on knowledge of the genetic code, possibly including optimizing codons based on the nature of the host cell (e.g. microorganism) to be used for expressing and/or secreting the recombinant fusion peptide(s). Suitable host cells will also be known to persons skilled in the art, illustrative examples of which include prokaryotic cells (e.g., *E. coli*) and eukaryotic cells (e.g., *P. pastoris*). Reference is made to "Short Protocols in Molecular Biology, 5th Edition, 2 Volume Set: A Compendium of Methods from Current Protocols in Molecular Biology" (by Frederick M. Ausubel (author, editor), Roger Brent (editor), Robert E. Kingston (editor), David D. Moore (editor), J. G. Seidman (editor), John A. Smith (editor), Kevin Struhl (editor), J Wiley & Sons, London).

As used herein, the terms "encode," "encoding" and the like refer to the capacity of a nucleic acid to provide for another nucleic acid or a polypeptide. For example, a nucleic acid sequence is said to "encode" a polypeptide if it can be transcribed and/or translated, typically in a host cell, to produce the polypeptide or if it can be processed into a form that can be transcribed and/or translated to produce the polypeptide. Such a nucleic acid sequence may include a coding sequence or both a coding sequence and a non-coding sequence. Thus, the terms "encode," "encoding" and the like include an RNA product resulting from transcription of a DNA molecule, a protein resulting from translation of an RNA molecule, a protein resulting from transcription of a DNA molecule to form an RNA product and the subsequent translation of the RNA product, or a protein resulting from transcription of a DNA molecule to provide an RNA product, processing of the RNA product to provide a processed RNA product (e.g., mRNA) and the subsequent translation of the processed RNA product. In some embodiments, the nucleic acid sequence encoding the B cell epitopes or fusion peptides herein described are codon-optimised for expression in a suitable host cell. For example, where the fusion peptide is to be used for inducing an immune response against Her2/neu in a human subject, the nucleic acid sequences can be human codon-optimised. Suitable methods for codon optimisation would be known to persons skilled in the art, such as using the "Reverse Translation" option of "Gene Design" tool located in "Software Tools" on the John Hopkins University Build a Genome website.

The two or more non-contiguous B cell epitopes of Her2/neu, as herein described, can be linked to one another within the fusion peptide by any means known to persons skilled in the art. The terms "link" and "linked" include direct linkage of two non-contiguous Her2/neu B cell epitopes via a peptide bond; that is, the C-terminus of one Her2/neu epitope is covalently bound via a peptide bond to the N-terminal of another, natively non-contiguous epitope. The terms "link" and "linked" also include within their meaning the linkage of two natively non-contiguous Her2/neu epitopes via an interposed linker element.

In an embodiment disclosed herein, at least two of said B cell epitopes or derivatives thereof are linked to one another via a non-native linker peptide sequence.

As used herein, the term "linker" refers to a short polypeptide sequence interposed between any two neighboring Her2/neu B cell epitopes or derivatives thereof within the fusion peptide. In an embodiment, the linker is a polypeptide linker of 1-10, preferably 1, 2, 3, 4 or 5 naturally or non-naturally occurring amino acids. In an embodiment, the linker is a carbohydrate linker. Suitable carbohydrate linkers will be known to persons skilled in the art. In another embodiment disclosed herein, the fusion peptide comprises one or more peptidic or polypeptidic linker(s) together with one or more other non-peptidic or non-polypeptidic linker(s). Further, different types of linkers, peptidic or non-peptidic, may be incorporated in the same fusion peptide as deemed appropriate. In the event that a peptidic or polypeptidic linker is used to join two respective B cell epitopic fragments from the ECD of Her2/neu, the linker will be advantageously incorporated such that its N-terminal end is bound via a peptide bond to the C-terminal end of the one epitopic fragment, and its C-terminal end via a peptide bond to the N-terminal end of the other fragment. The individual B cell epitopic fragments within the fusion peptide may also have one or more amino acids added to either or both ends, preferably to the C-terminal end. Thus, for example, linker or spacer amino acids may be added to the N- or C-terminus of the peptides or both, to link the non-contiguous peptides and to allow for convenient coupling of the peptides to each other and/or to a delivery system such as a virosome via a lipid molecule in the virosome serving as an anchor. An illustrative example of a suitable peptidic linker is LP (leucine-proline), as shown, for example, in SEQ ID NO:8.

It will be understood by persons skilled in the art that, where coupling of the a fusion peptide to the carrier protein is via a linker, it is preferable to effect such linker-mediated coupling from the C-terminus of the fusion peptide, since linker coupling from the N-terminus may, in some instances, have a negative influence on the desired immune response to be elicited.

Sequence Identity and Sequence Similarity

Reference to "at least 85%" includes 85%, 86%, 87%, 88%, 89%, 90%, 91%, 92%, 93%. 94%, 95%, 96%, 97%, 98%, 99% or 100% sequence identity or similarity, for example, after optimal alignment or best fit analysis. Thus, in preferred forms of the present invention, the sequence has at least 85%, preferably at least 86%, preferably at least 87%, preferably at least 88%, preferably at least 89%, preferably at least 90%, preferably at least 91%, preferably at least 92%, preferably at least 93%, preferably at least 94%, preferably at least 95%, preferably at least 96%, preferably at least 97%, preferably at least 98%, preferably at least 99% or preferably 100% sequence identity or sequence homology with the sequences identified herein, for example, after optimal alignment or best fit analysis.

The terms "identity", "similarity", "sequence identity", "sequence similarity", "homology", "sequence homology" and the like, as used herein, mean that at any particular amino acid residue position in an aligned sequence, the amino acid residue is identical between the aligned sequences. The term "similarity" or "sequence similarity" as used herein, indicates that, at any particular position in the aligned sequences, the amino acid residue is of a similar type between the sequences. For example, leucine may be substituted for an isoleucine or valine residue. This may be referred to as conservative substitution. In an embodiment, the amino acid sequences may be modified by way of conservative substitution of any of the amino acid residues contained therein, such that the modification has no effect on the binding specificity or functional activity of the modified polypeptide when compared to the unmodified polypeptide.

In some embodiments, sequence identity with respect to a polypeptide relates to the percentage of amino acid residues in the candidate sequence which are identical with the residues of the corresponding polypeptide after aligning the sequences and introducing gaps, if necessary, to achieve the maximum percentage homology, and not considering any conservative substitutions as part of the sequence identity. Neither N- or C-terminal extensions, nor insertions shall be construed as reducing sequence identity or homology. Methods and computer programs for performing an alignment of two or more amino acid sequences and determining their sequence identity or homology are well known to persons skilled in the art. For example, the percentage of identity or similarity of two amino acid sequences can be readily calculated using algorithms, for example, BLAST, FASTA, or the Smith-Waterman algorithm. The present invention extends to sequences having at least 70%, 75%, 80%, 85%, 90%, 93%, 95%, 96%, 97%, 98% or 99% sequence identity or sequence homology with the sequences identified herein, and to use of same in the methods described herein.

In some embodiments, sequence identity with respect to a polynucleotide relates to the percentage of nucleotides in the candidate sequence which are identical with the nucleotides of the corresponding polynucleotide after aligning the sequences and introducing gaps, if necessary, to achieve the maximum percentage homology, and not considering any conservative substitutions as part of the sequence identity. Methods and computer programs for performing an alignment of two or more polynucleotide or nucleic acid sequences and determining their sequence identity or homology are well known to persons skilled in the art.

Techniques for determining an amino acid sequence "similarity" are well known to persons skilled in the art. In general, "similarity" means an exact amino acid to amino acid comparison of two or more polypeptides or at the appropriate place, where amino acids are identical or possess similar chemical and/or physical properties such as charge or hydrophobicity. A so-termed "percent similarity" then can be determined between the compared polypeptide sequences. Techniques for determining nucleic acid and amino acid sequence identity also are well known in the art and include determining the nucleotide sequence of the mRNA for that gene (usually via a cDNA intermediate) and determining the amino acid sequence encoded thereby, and comparing this to a second amino acid sequence. In general, "identity" refers to an exact nucleotide to nucleotide or amino acid to amino acid correspondence of two polynucleotides or polypeptide sequences, respectively.

Two or more polynucleotide sequences can also be compared by determining their "percent identity". Two or more amino acid sequences likewise can be compared by determining their "percent identity". The percent identity of two sequences, whether nucleic acid or peptide sequences, may be described as the number of exact matches between two aligned sequences divided by the length of the shorter sequence and multiplied by 100. An approximate alignment for nucleic acid sequences is provided by the local homology algorithm of Smith and Waterman, Advances in Applied Mathematics 2:482-489 (1981). This algorithm can be extended to use with peptide sequences using the scoring matrix developed by Dayhoff, Atlas of Protein Sequences and Structure, M. O. Dayhoff ed., 5 suppl. 3:353-358, National Biomedical Research Foundation, Washington, D.C., USA, and normalized by Gribskov, Nucl. Acids Res. 14(6):6745-6763 (1986). Suitable programs for calculating the percent identity or similarity between sequences are generally known in the art.

An illustrative example for determining nucleic acid sequence identity uses a subject nucleic acid sequence to search on a nucleic acid sequence database, such as the GenBank database (accessible at http://www.ncbi.nln.nih.gov/blast/), using the program BLASTN version 2.1 (based on Altschul et al. (1997) Nucleic Acids Research 25:3389-3402). This program can be used in the ungapped mode. Default filtering is used to remove sequence homologies due to regions of low complexity. The default parameters of BLASTN can be used. An illustrative example for determining amino acid sequence identity, an amino acid sequence is used to search a protein sequence database, such as the GenBank database (accessible at web site http://www.ncbi.nln.nih.gov/blast/), using the BLASTP program. The program can be used in the ungapped mode. Default filtering is used to remove sequence homologies due to regions of low complexity. The default parameters of BLASTP are utilized. Filtering for sequences of low complexity may use the SEG program.

Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e., resulting in the highest percentage homology over the comparison window) generated by any of the various methods selected. Reference also may be made to the BLAST family of programs as for example disclosed by Altschul et al., 1997, Nucl. Acids Res.25:3389. A detailed discussion of sequence analysis can be found in Unit 19.3 of Ausubel et al., "Current Protocols in Molecular Biology", John Wiley & Sons Inc, 1994-1998, Chapter 15.

Carrier Protein

CRM-197 (GenBank Accession No. 1007216A; SEQ ID NO:61) is an enzymatically inactive and nontoxic form of diphtheria toxin that contains a single amino acid substitution (Gly-Glu) at amino acid residue 52. A single GCA mutation that leads to the Glu52 substitution distinguishes CRM-197 from its wild-type species. The absence of toxicity of CRM-197 appears to be due to the loss of enzymatic activity of its fragment A, which in the wild-type species catalyzes the chemical modification of elongation factor 2 (translocase) in infected cells that is essential for protein synthesis. This non-toxic property makes CRM-197 a suitable carrier protein for the preparation of conjugated vaccines.

(CRM-197; GenBank Accession No. 1007216A)
SEQ ID NO: 61
GADDVVDSSKSFVMENFSSYHGTKPGYVDSIQKGIQKPKSGTQGNYDDD

WKEFYSTDNKYDAAGYSVDNENPLSGKAGGVVKVTYPGLTKVLALKVDN

AETIKKELGLSLTEPLMEQVGTEEFIKRFGDGASRVVLSLPFAEGSSSV

EYINNWEQAKALSVELEINFETRGKRGQDAMYEYMAQACAGNRVRRSVG

SSLSCINLDWDVIRDKTKTKIESLKEHGPIKNKMSESPNKTVSEEKAKQ

YLEEFHQTALEHPELSELKTVTGTNPVFAGANYAAWAVNVAQVIDSETA

DNLEKTTAALSILPGIGSVMGIADGAVHHNTEEIVAQSIALSSLMVAQA

IPLVGELVDIGFAAYNFVESIINLFQVVHNSYNRPAYSPGHKTQPFLHD

GYAVSWNTVEDSIIRTGFQGESGHDIKITAENTPLPIAGVLLPTIPGKL

DVNKSKTHISVNGRKIRMRCRAIDGDVTFCRPKSPVYVGNGVHANLHVA

FHRSSSEKIHSNEISSDSIGVLGYQKTVDHTKVNSKLSLFFEIKS

Methods by which a fusion peptide can be coupled to CRM-197 are known to persons skilled in the art.

Illustrative examples include those described by Chang et al. (1998, *FEBS Letters,* 427:362-366) and Berti et al. (2004, *Biophysical Journal,* 86:3-9), as well as those set out hereinbelow in Example 1, hereinbelow.

Conjugation of a fusion peptide, as herein described, to CRM-197 is typically achieved through activation of the lysyl residues using suitable crosslinkers. Since CRM-197 contains 40 lysines residues, and many of them are available for crosslinking, the end products of CRM-197 conjugation are invariably heterogeneous. Without being bound by theory or a particular mod of action, it is generally understood that the ratio of fusion peptide: carrier protein depends on the size or molecular weight of the fusion peptide. For instance, where the fusion peptide is relatively small (e.g., about 10 amino acids in length), it may be possible to produce a carrier protein that is conjugated with 20-39 fusion peptides. Conversely, for a larger fusion peptide, the carrier protein may be conjugated with up to, or fewer than, 20 fusion peptides. In an embodiment described herein, the carrier protein comprises from 2 to 39 fusion peptides. In another embodiment, the carrier protein comprises at least 20 fusion peptides. In yet another embodiment, the carrier protein comprises from 6 to 12 fusion peptides.

The fusion peptide is typically coupled to the carrier protein by a covalent bond. However, in some embodiments, the fusion peptide may be coupled to the carrier protein by a non-covalent association. Where the fusion peptide is non-covalently associated with the carrier protein, the non-covalent association will typically involve an electromagnetic interaction between one or more atoms of the fusion peptide with one or more atoms of the carrier protein. Illustrative examples include ionic bonding (i.e., the attraction formed between two oppositely charged ions by virtue of this opposite charge), Van der Weals forces (i.e., forces between permanent and/or induced dipoles of existing covalent bonds within the fusion peptide and the carrier protein) and/or hydrophobic interactions (i.e., forces resulting from the tendency of hydrophobic/aliphatic portions within the fusion peptide(s) herein described to associate with hydrophobic portions of the carrier protein).

Adjuvants

As used herein, the term "adjuvant" typically refers to a class of substance that can increase the magnitude of the immune response elicited by the fusion peptide-carrier protein conjugate beyond that which would be expected, either from the fusion peptide alone or from the fusion peptide-carrier protein conjugate as herein described in the absence of an adjuvant.

Suitable adjuvants will be known to persons skilled in the art. Non-limiting examples of suitable adjuvants include aluminium salts (e.g. aluminium hydroxide, aluminium phosphate and potassium aluminium sulfate (also referred to as Alum)), liposomes, virosomes, water-in-oil or oil-in-water emulsions (e.g. Freund's adjuvant, Montanide®, MF59® and AS03), 3-O-desacyl-4'-monophosphoryl lipid A (MPL) and adjuvants containing MPL (e.g. AS01, AS02 and AS04) and saponin-based adjuvants. Saponin-based adjuvants include saponins or saponin derivatives from, for example, *Quillaja saponaria, Panax ginseng Panax notoginseng, Panax quinquefolium, Platycodon grandiflorum, Polygala senega, Polygala tenuifolia, Quillaja brasiliensis, Astragalus membranaceus and Achyranthes bidentata*. Exemplary saponin-based adjuvants include iscoms, iscom matrix, ISCOMATRIX™ adjuvant, Matrix M™ adjuvant, Matrix C™ adjuvant, Matrix Q™ adjuvant, AbISCO®-100 adjuvant, AbISCO®-300 adjuvant, ISCOPREP™, an ISCOPREP™ derivative, adjuvant containing ISCOPREP™ or an ISCOPREP™ derivative, QS-21, a QS-21 derivative, and an adjuvant containing QS-21 or a QS21 derivative. The vaccine composition as herein described can also be associated with immumodulatory agents, including, for example, cytokines, chemokines and growth factors. Mixtures of two or more adjuvants within the same vaccine composition are also contemplated herein.

In an embodiment, the adjuvant is aluminium hydroxide. In another embodiment, the adjuvant is Montanide.

In an embodiment disclosed herein, the vaccine composition further comprises a checkpoint inhibitor. The term "checkpoint inhibitor" will be understood by persons skilled in the art as meaning molecules that inhibit, reduce or otherwise interfere with or modulate one or more checkpoint proteins, either totally or partially. Illustrative examples of suitable checkpoint inhibitors include antibodies and antigen-binding fragments thereof (e.g., Fab fragments). Suitable checkpoint proteins will be known to persons skilled in the art, illustrative examples of which include CTLA-4 and its ligands CD80 and CD86; PD1 and its ligands PDL1 and PDL2; OX40 and its ligand OX40L; LAG-3 and its ligand MHC class I or II; TIM-3 and its ligand GAL-9; and B- and T-lymphocyte attenuator (BTLA) and its ligand herpes virus entry mediator (HVEM).

Pharmaceutical Composition

The present specification also describes a pharmaceutical composition comprising the vaccine composition as herein described and a pharmaceutically acceptable carrier. Suitable pharmaceutically acceptable carriers (e.g. excipients, diluents, etc.). will be known to persons skilled in the art. For example, a variety of aqueous (pharmaceutically acceptable) carriers may be used, such as buffered water, 0.4% saline, 0.3% glycine, hyaluronic acid and the like. These compositions may be sterilized by conventional, well known sterilization techniques or may be sterile-filtered. The resulting aqueous solutions may be packaged for use as is or lyophilized, the lyophilized preparation being combined with a sterile solution prior to administration. The compositions may further comprise pharmaceutically acceptable auxiliary substances as required to approximate physiological conditions, such as pH-adjusting and buffering agents, tonicity-adjusting agents, wetting agents and the like, for example sodium acetate, sodium lactate, sodium chloride, potassium chloride, calcium chloride, sorbitan monolaurate, triethanolamine oleate, sucrose or other carbohydrates, among many others. Suitable methods for preparing parenterally administrable compounds will be known or apparent to those skilled in the art and are described in more detail in, for example, A. Gennaro (2000) "Remington: The Science and Practice of Pharmacy", 20th edition, Lippincott, Williams, & Wilkins; Pharmaceutical Dosage Forms and Drug Delivery Systems (1999) H. C. Ansel et al., eds 7.sup.th ed., Lippincott, Williams, & Wilkins; and Handbook of Pharmaceutical Excipients (2000) A. H. Kibbe et al., eds., 3.sup.rd ed. Amer. Pharmaceutical Assoc.

The pharmaceutical composition may be in a form suitable for parenteral administration (e.g., subcutaneous, intramuscular or intravenous injection) or in an aerosol form suitable for administration by inhalation, such as by intranasal inhalation or oral inhalation.

The pharmaceutical compositions described herein may also be provided in a kit. The kit may comprise additional components to assist in performing the methods as herein described, such as administration device(s), excipients(s), and/or diluent(s). The kits may include containers for housing the various components and instructions for using the kit components in such methods.

In an embodiment disclosed herein, the pharmaceutic composition further comprises a checkpoint inhibitor, as described elsewhere herein.

Uses and Methods for Treating or Preventing Cancer

Also disclosed herein is a method of treating or preventing a cancer characterized by expression or over-expression of Her2/neu in a patient in need thereof, the method comprising the step of administering to said patient an effective amount of the vaccine composition as herein described, or the pharmaceutical composition as herein described.

The present disclosure also extends to use of the vaccine composition, as herein described, in the manufacture of a medicament for treating or preventing a cancer characterized by expression or over-expression of Her2/neu in a patient in need thereof.

The present disclosure also extends to the vaccine, as herein described, or the pharmaceutical composition, as herein described, for use in treating or preventing a cancer characterized by expression or over-expression of Her2/neu in a patient in need thereof.

Persons skilled in the art will be familiar with the type of cancers that are characterised by the expression or over-expression of Her2/neu protein. Illustrative examples include breast cancer, ovarian cancer, endometrial cancer, gastric cancer, pancreatic cancer, prostate cancer and salivary gland cancer. In an embodiment, the cancer is breast cancer. In another embodiment, the cancer is gastric cancer.

The vaccine or pharmaceutical compositions, as described herein, are typically administered in an "effective amount"; that is, an amount effective to elicit any one or more inter alia of a therapeutic or prophylactic effect. Persons skilled in the art would be able, by routine experimentation, to determine an effective, non-toxic amount to include in a pharmaceutical composition or to be administered for the desired outcome. In general, the vaccine and/or pharmaceutical compositions, as disclosed herein, can be administered in a manner compatible with the route of administration and physical characteristics of the recipient (including health status) and in such a way that it elicits the desired effect(s) (i.e. therapeutically effective, immunogenic and/or protective). For example, the appropriate dosage of a composition may depend on a variety of factors including, but not limited to, a subject's physical characteristics (e.g., age, weight, sex), whether the composition is being used as single agent or as part of adjunct therapy, the progression (i.e., pathological state) of any underlying cancer, and other factors that may be recognized by persons skilled in the art. Other illustrative examples of general considerations that may be considered when determining, for example, an appropriate dosage of the compositions are discussed by Gennaro (2000, "Remington: The Science and Practice of Pharmacy", 20th edition, Lippincott, Williams, & Wilkins; and Gilman et al., (Eds), (1990), "Goodman And Gilman's: The Pharmacological Bases of Therapeutics", Pergamon Press).

It is expected that the amount will fall in a relatively broad range that can be determined through methods known to persons skilled in the art, having regard to some of the considerations outlined above.

An effective amount of fusion peptide (conjugated to the carrier protein), as hereindescribed, will generally be in a range of from about 5 µg to about 1.0 mg of fusion peptide per subject, from about 10 µg to about 500 µg of fusion peptide per subject, or from about 15 µg to about 60 µg of fusion peptide per subject. An effective amount can be ascertained, for example, by standard methods involving measurement of antigen-specific antibody titres. The level of immunity provided by the compositions herein described can be monitored to determine the need, if any, for boosters. For instance, following an assessment of an antigen-specific antibody titre in the serum, typically days or weeks following the first administration of the composition in a subject, optional booster immunisations may be required and/or desired. The antigen-specific antibody titres are likely to be enhanced by the use of multiple doses, as illustrated in the Examples hereinbelow.

The vaccine and/or pharmaceutical compositions, as described herein, can be administered to a subject in need thereof in isolation or in combination with additional therapeutic agent(s); that is, as part of an adjunct therapy. In the context of adjunct therapy, the administration may be simultaneous or sequential; that is, the vaccine and/or pharmaceutical composition is administered first, followed by administration of the additional therapeutic and/or prophylactic agent(s), or the vaccine and/or pharmaceutical composition is administered following the administration of the additional therapeutic agent(s). Thus, where two or more entities are administered to a subject "in conjunction", they may be administered in a single composition at the same time, or in separate compositions at the same time, or in separate compositions separated in time.

The additional therapeutic agent(s) may comprise a checkpoint inhibitor, as described elsewhere herein. Thus, in an embodiment, the methods disclosed herein further comprise the step of administering to said patient an effective amount of a checkpoint inhibitor, as herein described.

It will be apparent to persons skilled in the art that the optimal quantity and spacing of individual dosages, if required to induce the desired immune response, can be determined, for example, by the form, route and site of administration, and the nature of the particular subject to be treated, as is described elsewhere herein. Optimum conditions can be determined using conventional techniques known to persons skilled in the art.

In some instances, it may be desirable to have several or multiple administrations of the vaccine and/or pharmaceutical compositions, as herein described. For example, the compositions may be administered 1, 2, 3, 4, 5, 6, 7, 8, 9, 10, or more times. The administrations may be from about one day intervals to about twelve week intervals, and in certain embodiments from about one to about four week intervals. Periodic re-administration may be required to achieve a desirable therapeutic result, such as a reduction in tumour size and/or a reduction in the occurrence of metastases. It will also be apparent to persons skilled in the art that the optimal course of administration can be ascertained using conventional course of treatment or efficacy or immune status determination tests.

It will be understood that "inducing" an immune or antigen-specific antibody response, as contemplated herein, includes eliciting or stimulating an immune response and/or enhancing a previously existing immune response to obtaining a desired physiologic effect such as a reduction in tumour size and/or a reduction in the occurrence of metastases. The effect can be prophylactic in terms of completely or partially preventing the occurrence of the cancer, completely or partially preventing the occurrence of metastases, and/or completely or partially preventing a symptom associated with said cancer.

As used herein, the terms "administration" or "administering" typically refer to the step of introducing the vaccine and/or pharmaceutical compositions, as herein described, into a patient's body so that the patient's immune system mounts a response to the multiple Her2/neu B cell epitopes within the fusion peptide(s). As used herein, a "patient in need thereof" includes an individual who has been diagnosed with cancer, wherein the cancer cells express or over-express the Her2/neu protein. It also includes individuals who have not yet been diagnosed with cancer, such as those individuals who have not presented with any symptoms, but who may have, for example, a family history of cancer and therefore a suspected genetic predisposition to develop cancer. In its broadest sense, the term "a patient in need thereof" therefore encompasses individuals with an already present need, as well as individuals who are at risk of developing an Her2/neu associated cancer.

As used herein, a medicament which "prevents" cancer will reduce an individual's risk of develop cancer, ideally down to zero. Furthermore, this term also refers to the prevention of re-development of cancer, e.g. following surgery of a primary tumour. As used herein, a medicament which "treats" cancer will ideally eliminate the disease altogether by eliminating its underlying cause so that, upon cessation of administration of the composition, the disease does not re-develop, but remains in remission. As used herein, a medicament which "ameliorates" cancer does not eliminate the underlying cause of the disease, but reduces the severity of the disease as measured by any established grading system and/or as measured by an improvement in the patient's well-being, e.g. decrease in pain and/or discomfort.

An "effective amount" is an amount of a pharmaceutical preparation that alone, or together with further doses according to an established dosing regimen, effects the desired prevention, treatment or amelioration, as discussed elsewhere herein.

The route and regimen of administration may vary depending upon the stage or severity of the condition to be treated, and is to be determined by the skilled practitioner. For example, a vaccine or pharmaceutical composition according to the present invention, as herein described, may be administered in subcutaneous, intradermal, intralymphatic or topical or mucosal (nasal), or intramuscular form. All of these forms are well known to those of ordinary skill in the pharmaceutical arts.

In certain embodiments, the compositions described herein can be administered in intramuscular, subcutaneous, intralymphatic or intranasal routes known to those of ordinary skill in the art.

As discussed elsewhere herein, the dosage regimen utilizing the compositions as herein described is selected in accordance with a variety of factors, including, for example, the age, weight, and medical condition of the patient, the stage and severity of the condition to be treated, and the particular fusion peptide(s) intended for administration. A physician of ordinary skill can readily determine and prescribe the effective amount of, for example, the carrier protein (comprising a fusion peptide(s) coupled thereto) required to prevent, treat or ameliorate the progress or severity of a malignancy. The dosage regimen will also take into account the amount of adjuvant to be administered, which is expected to varying depending on at least some of the factors that will govern the amount of carrier protein/fusion peptide(s) to be administered to the subject, such as age, weight and medical condition of the patient. Optimal precision in achieving a concentration of carrier protein/fusion peptide(s) and/or adjuvant with the range that yields efficacy (i.e., an effective amount) either without toxicity or with no more than acceptable toxicity, requires a regimen based, at least in part, on the kinetics of the availability of the carrier protein/fusion peptide(s) and/or adjuvant to the target site(s). This process will typically involve a consideration of the distribution, equilibrium, and elimination of the carrier protein/fusion peptide(s) and/or adjuvant, which will be within the ability of persons skilled in the art.

All patents, patent applications and publications mentioned herein are hereby incorporated by reference in their entireties.

Those skilled in the art will appreciate that the invention described herein is susceptible to variations and modifications other than those specifically described. It is to be understood that the invention includes all such variations and modifications which fall within the spirit and scope. The invention also includes all of the steps, features, compositions and compounds referred to or indicated in this specification, individually or collectively, and any and all combinations of any two or more of said steps or features.

Certain embodiments of the invention will now be described with reference to the following examples which are intended for the purpose of illustration only and are not intended to limit the scope of the generality hereinbefore described.

EXAMPLES

The following examples are directed to the conjugation of two fusion peptides (non-contiguous B cell epitopes derived from Her2/neu) to the recombinant detoxified Diphtheria toxin, CRM197. Initial analysis of the fusion peptide-carrier protein conjugates by SDS-PAGE and immunoblotting were performed. Finally, fusion peptide-carrier protein conjugates were shipped to Austria for the initial immunogenicity study in animals.

Example 1—Conjugation of Her2/Neu Peptide Antigens to Recombinant Detoxified Diptheria Toxin Variant, CRM-197

The virosome-based breast cancer vaccine, PEV6A/B, has been tested successfully in a clinical phase I trial (Wiedermann et al., Breast Cancer Res Treat. 2010). However, this vaccine formulation featured substantial technical limitations with regard to stability and component compatibility, best illustrated by the fact that two separate injections were unavoidable.

The PEV6C approach overcomes the technical limitations of PEV6A/B. PEV6C combines all three antigens (P6, P7, and P4; SEQ ID NOs:1-3; respectively) in a single peptide chain (see also WO 2011/020604A1; Multi-epitope vaccine for her2/neu-associated cancers) and can be formulated as a stable, lyophilizable single dose application form.

Preparation and Results

The following fusion proteins were used for conjugation to the carrier protein CRM-197:

Peptide 1: P467 (before conjugation):
(SEQ ID NO: 8)
H-Pro-Glu-Ser-Phe-Asp-Gly-Asp-Pro-Ala-Ser-Asn-Thr- Ala-Pro-Leu-Gln-Pro-Arg-Val-Leu-Gln-Gly-Leu-Pro- Arg-Glu-Tyr-Val-Asn-Ala-Arg-His-Ser-Leu-Pro-Tyr- Met-Pro-Ile-Trp-Lys-Phe-Pro-Asp-Glu-Glu-Gly-Ala- Cys cetate salt;
and Peptide 2: P647 (before conjugation):
(SEQ ID NO: 9)
H-Arg-Val-Leu-Gln-Gly-Leu-Pro-Arg-Glu-Tyr-Val-Asn- Ala-Arg-His-Ser-Pro-Glu-Ser-Phe-Asp-Gly-Asp-Pro- Ala-Ser-Asn-Thr-Ala-Pro-Leu-Gln-Pro-Tyr-Met-Pro- Ile-Trp-Lys-Phe-Pro-Asp-Glu-Glu-Gly-Ala-Cys acetate salt.

The conjugation reaction was performed in a PBS buffer at pH 7.4, using the cross-linking agent Sulfosuccinimidyl-4-(N-maleimidomethyl)cyclohexane-1-carboxylate (Sulfo-SMCC). This reagent reacts first with the primary amines (i.e. lysine residues) on the CRM-197 carrier protein before it is allowed to react with thiol groups (i.e. cysteine residues). In CRM-197, 39 lysine residues were theoretically available for a reaction with the cross-linking reagent. To reach a good distribution of the peptide antigen on the carrier protein, the fusion peptide: carrier protein ratio was adjusted to achieve an average conjugation of 20 fusion peptide molecules per molecule of CRM197. The reaction was allowed to proceed for 45 min at room temperature (RT), as follows:

TABLE 3

| | | Material | | |
|---|---|---|---|---|
| Product | Supplier | Prod. No. | Lot No | Comments |
| Peptide P647 (before lipid conjugation) | Bachem | 4086800 | 88800/1K | MW = 5498 Da; 49 ea, pI = 4.7 PESFDGDPASNTAPLQPRVLQGL PREYVNARHSLPYMPIWKFPDEE GAC |
| Peptide P647 (before lipid conjugation) | Bachem | 4088709 | 88799/1K | MW = 5287 Da; 47 ea, pI = 4.7 RVLQGLPREYVNARHS PESFDGDPASNTAPLQP YMPIWKFPDEEGAC |
| Sulfo-SMCCC | Thermo-Fisher Scientific | 022622 | PD199643 | 8x 2 mg Mr = 436.4 |
| CRM197 Diphteria Toxin nontoxic mutant | Merck (Calbiochem) | 322327 | D00149725 | 1 mg aliquots. 2 mg/mL solution in PBS pH 7.4 after reconstitution, MW - 58-63 kDa; pI = 5.85, 39 Lys redisdues |
| EDTA pH 8.0, 0.5M | Calbiochem/Merck | 324506 | D0006185106 | 0.1 L |

TABLE 3-continued

| | | Material | | |
|---|---|---|---|---|
| Product | Supplier | Prod. No. | Lot No | Comments |
| EMSO, LC-MS Grade | Thermo-Fisher Scientific | 0085190 | PG204999 | 50 mL |
| 20x Modified DuLbecco's PBS Bufftter | Thermo-Fisher Scientific | 0028344 | PG201076 | 0.5 L |
| Zebra Spin Desalting Columns, 40K, 10 mL | Thermo-Fisher Scientific | 0087772 | PG202270 | 5 pack |
| WFI | Berna Biotechs | 100005 | 1004241 | |

Procedure

1. Remove fusion peptides from −20° C. and let stand at room temperature (RT) for about 10 min, before opening the vials.
2. Weigh fusion peptides into 3 mL glass vials:
   (a) P467, 7.8 mg, resuspended with 780 μL water for injection (WFI);
   (b) P467, 7.1 mg, resuspended with 710 μL dimethylsulfoxide (DMSO);
   (c) P647, 6.9 mg, resuspended with 690 μL WFI;
   (d) P647, 9.0 mg, resuspended with 900 μL DMSO;

All solutions were readily resuspended, and no aggregates or turbidity was visible.

3. Dilute 20× phosphate buffered saline (PBS) to 1×PBS with Milli Q water, and add ethylenediaminetetraacetic acid (EDTA) to a final concentration of 1 mM.
4. Reconstitute 6 vials of CRM197 with 0.5 mL WFI to 2 mg/mL. Pool 3 vials to result in 2 batches, and store at 4° C. (1.5 mL per batch, each 3 mg).
5. Take one vial of Sulfo-SMCC (2 mg), and add 200 μL of PBS/1 mM ETDA to it and dissolve (10 mg/mL stock solution; solution remained turbid).
6. Add 75 μL of Sulfo-SMCC (10 mg/mL) to each vial of 3 mg CRM197. Total volume: 1.575 mL.
7. Incubate the vials for 45 mins at RT under slow mixing (rotating, 25 rpm). During that time, equilibrate ×2 Zeba Spin Desalting Columns with PBS/EDTA buffer.
8. After incubation step 7, the reaction is transferred to the equilibrated Zeba Spin Column (1.5 mL) and 200 μL of PBS/EDTA is added, and then centrifuged at 1000×g for 4 min.
9. 1.8 mL of each solution was recovered.
10. Add to a fresh 3 mL vial, as follows:
    (a) Vial 1: 600 μL P467 (10 mg/mL in WFI); and
    (b) Vial 2: 600 μL P647 (10 mg/mL in WFI).
11. To each vial, add 50 μL of 20×PBS to raise the pH of the solution to approx. 7.
12. To each vial, add 1.8 mL of the desalted CRM197-SMCC.
13. Incubate the vials for 45 min at RT under slow mixing (rotating), then store the vials at 4° C. until analysis. During incubation, it was noted that precipitates became visible in Vial 2. However, precipitates disappeared after warming of the solution.

Summary

Peptide P467-CRM197, ca. 2.449 mg/mL P467, ca. 1.22 mg/mL CRM197, ca. 2450 μL; in 1×PBS/1 mM EDTA, Lot 140829-1_am.

Peptide P647-CRM197, ca. 2.449 mg/mL P647, ca. 1.22 mg/mL CRM197, ca. 2450 μL; in 1×PBS/1 mM EDTA, Lot 140829-2_am.

It was observed that the P647-CRM197 peptide conjugate showed a tendency to aggregate while the reaction proceeded. With the P467-CRM197 peptide conjugate, no aggregation visible by eye.

Example 2—Coomassie Blue Stain and Immunoblot of CRM197-Antigen Conjugates Using Mouse Antiserum E The conjugate formulations were analyzed by SDS-PAGE and evaluated by Coomassie Blue-staining of the gel and by immunoblotting, using a previously generated mouse serum against the combination of peptide antigens P4, P6 and P7 conjugated to tetanus toxoid (antiserum E).

TABLE 4

| | | Materials | | |
|---|---|---|---|---|
| Product | Supplier | Prod. No. | Lot No | Comments |
| Peptide P647 (before lipid conjugation) | Bachem | 4086800 | 88800/1K | MW = 5498 Da; 49 ea, pI = 4.7 PESFDGDPASNTAPLQPRVLQGL PREYVNARHSLPYMPIWKFPDEE GAC |

TABLE 4-continued

Materials

| Product | Supplier | Prod. No. | Lot No | Comments |
|---|---|---|---|---|
| Peptide P647 (before lipid conjugation) | Bachem | 4088709 | 88799/1K | MW = 5287 Da; 47 ea, pI = 4.7 RVLQGLPREYVNARHS PESFDGDPASNTAPLQP YMPIWKFPDEEGAC |
| CRM197 Diphteria Toxin nontoxic mutant | Merck (Calbiochem) | 322327 | D00149725 | 1 mg aliquots. 2 mg/mL solution in PBS pH 7.4 after reconstitution; MW - 58-63 kDa; pI = 5.85, 39 Lys redisdues |
| Peptid P467-CRM197 | Mymetics | n.a. | 140829-1_am | ca.2.449 mg/mL P467, ca. 1.22 mg/mL CRM197, in 1x PBS/1 mM EDTA. |
| Peptid P647-CRM197 | Mymetics | n.a. | 140829-2_am | ca.2.449 mg/mL P647, ca. 1.22 mg/mL CRM197, in 1x PBS/1 mM EDTA. |
| 10x Tris/Glycine/SDS | BioRad | 161-0732 | 116812 | |
| 4x Laemmli Sample Buffer | BioRad | 161-0747 | 350002344 | |
| Precision Plus Protein ™ Dual Extra Standards | BioRad | 161-0377 | 310013154 | (2-260 kD), 9 blue-stained bands, and 3 pink reference bands (2, 25, 75 kD) |
| Bio-Safe Coomassie stain | BioRad | 161-0786 | n.a. | |
| 4-20% Mini-PROTEAN ® TGX ™ Gel | BioRad | 456-1095 | 400093571 | 12 well, 20 µl |
| Nitrocellulose membrane | Thermo Fisher/Pierce | 88025 | PE1844001 | 0.45 µm, 8 cm x 8 cm |
| Trans-Blot ® Turbo ™ Mini Nitrocellulose Transfer Packs. | BioRad | 170-4158 | 400093907 | 7 x 8.5 cm, precut blotting transfer pack |
| SuperBlock (PBS) Blocking Buffer | Thermo Fisher/Pierce | 67580 | PR201632 | |
| Anti-P4/P6/P7 mouse serum, D pool | Univ Vienna | n.a. | n.a. | Mouse serum from immunisation with peptides integrated in influenza virosomes |
| Anti-P4/P6/P7 mouse serum, E pool | Univ Vienna | n.a. | n.a. | Mouse serum from immunisation with peptides conjugated to Tetanus toxoid |
| anti-mouse IgG HRP | KPL | 074-1802 | 101080 | |
| TMB substrate solution | Seramun | S-002-4 TMB | | |
| 20x Modified Dulbecco's PBS Buffer | Thermo Fisher Scientific | 0028344 | PG201076 | 1 L if 1x PBS prepared with MilliQ water, 140902-am |
| Reducing Agent: β-ME | Sigma | 63689 | n.a. | 14.3M solution |
| WFI | Berna Biotech | 100605 | 1004241 | |

Procedure

Two SDS-PA gels were prepared as follows:
CRM197 (2 mg/mL) stock solution was diluted 1:10 in PBS pH 7.4
Anti-conjugate solutions were diluted 1:10 in PBS pH 7.4
Unconjugated fusion peptides were prepared as stock solutions of 10 mg/mL and diluted 1:20 in PBS pH 7.4

In total, 36 µL of every sample were prepared, and 15 µL were loaded per lane. Two identical gels were prepared: Gel 1 was stained with Coomassie Blue, and Gel 2 was used for the Western blot. The distribution of samples in Gel 1 and Gel 2 is summarised in Table 5, below:

TABLE 5

| Proben Beschrelbung | WFI [µL] | Probe [µL] | LDS 4x Buffer [µL] | Reducing Agent [µL] |
|---|---|---|---|---|
| 1 Precision Plus Protein ™ Dual Xtra | — | 10 | — | — |
| 2 CRM197 - 0.25 ug [1:10] | 23 | 3 | 9 | 1 |
| 3 CRM197 - 0.5 ug [1:10] | 20 | 6 | 9 | 1 |
| 4 CRM197 - 1.0 ug [1:10] | 14 | 12 | 9 | 1 |
| 5 P467-CRM197 - 0.25 ug [1:10] | 22.2 | 3.8 | 9 | 1 |
| 6 P467-CRM197 - 1.0 ug [undil.] | 24.5 | 1.5 | 9 | 1 |
| 7 P647-CRM197 - 0.25 ug [1:10] | 22.2 | 3.8 | 9 | 1 |
| 8 P647-CRM197 - 1.0 ug [undil.] | 24.5 | 1.5 | 9 | 1 |
| 9 P467 - 0.25 ug [1:20] | 24.8 | 1.2 | 9 | 1 |
| 10 P467 - 1.0 ug [1:20] | 21.2 | 4.8 | 9 | 1 |
| 11 P647 - 0.25 ug [1:20] | 24.8 | 1.2 | 9 | 1 |
| 12 P647 - 1.0 ug [1:20] | 21.2 | 4.8 | 9 | 1 |

Results

Gel 1—Coomassie Blue Stain

Gel 1 was immersed in Bio-Safe Coomassie Blue stain for 1 hr at RT under shaking, and then rinsed with MilliQ water for 1 hr at RT.

Gel 2—Western Blot

After electrophoresis, Gel 2 was removed from the cassette, and rinsed shortly in Milli Q water. The transfer sandwich was then prepared according to the manufacturer's instructions (BioRad) and installed in a Turbo Transfer Blot machine. After the transfer, the nitrocellulose membrane was controlled for the complete presence of the prestained marker proteins. Only minimal amounts of marker remained visible in the SDS PA gel. The membrane was then incubated in SuperBlock buffet for 1 hr at RT. Mice serum Pool E was diluted 1:500 in SuperBlock, and incubated on the membrane for 2 hrs at RT. The membrane was then washed thrice with 1×PBS for 5 min each. The membrane was then incubated with anti-mouse IgG (KPL, 074-1802; Ab20), diluted 1:5000 in SuperBlock, for 1 hr at RT. The membrane was then washed thrice with 1×PBS for 5 min each and developed with 3,3',5,5'-Tetramethylbenzidine (TMB) for 5 min at RT.

The results showed a clear shift in molecular weight for each CRM197 conjugate towards larger molecular weights, indicative of strong conjugation of the fusion peptides to CRM197. The broad conjugate bands observed in both cases also suggested the relatively large distribution of the fusion peptides on the carrier protein, as was expected from the conjugation reaction. The results also suggested that there is no (or minimal) amount of unconjugated CRM197 protein remaining. On the other hand, a minor fraction of fusion peptides was observed, estimated to be <10% of the total fusion peptides used.

Conclusions

A clear shift in the CRM197 conjugates was observed, indicating the successful conjugation of P467 and P647 fusion peptides to the CRM197 carrier protein.

There was no significant difference observable between the P467-CRM197 and P647-CRM197 conjugates.

A limited amount of free fusion peptides was observed in both conjugation reactions.

The immunoblot with the used antiserum demonstrated some cross-reactivity with the CRM197 diphtheria toxin, although it was raised with tetanus toxoid peptide conjugates. It confirms the shift of the CRM197 molecule after conjugation, but as this is not specific for the two fusion peptides, its conjugation to the protein could not be confirmed. The antiserum stains the free unconjugated fusion peptides, with P467 slightly better than the P647.

Example 3—Immunoblot of CRM197-Antigen Conjugates Using Mouse Antiserum D

The conjugate formulations were analyzed by SDS-PAGE and evaluated by immunoblotting using a previously generated mouse serum against the combination of peptide antigens P4, P6 and P7 conjugated to influenza virosomes (antiserum D). The presence of the fusion peptides P467 and P647 on the CRM197 carrier protein was confirmed separately by an immunoblot using antiserum D.

TABLE 6

| | | Material | | |
|---|---|---|---|---|
| Product | Supplier | Prod. No. | Lot No | Comments |
| Peptide P647 (before lipid conjugation) | Bachem | 4086800 | 88800/1K | MW = 5498 Da; 49 ea, pI = 4.7 PESFDGDPASNTAPLQPRVLQGL PREYVNARHSLPYMPIWKFPDEE GAC |
| Peptide P647 (before lipid conjugation) | Bachem | 4088709 | 88799/1K | MW = 5287 Da; 47 ea, pI = 4.7 RVLQGLPREYVNARHS PESFDGDPASNTAPLQP YMPIWKFPDEEGAC |
| CRM197 Diphteria Toxin nontoxic mutant | Merck (Calbiochem) | 322327 | D00149725 | 1 mg aliquots. 2mg/mL solution in PBS pH 7.4 after reconstitution; MW - 58-63 kDa; = pI = 5.85, 39 Lys redisdues |

TABLE 6-continued

| Product | Supplier | Prod. No. | Lot No | Comments |
|---|---|---|---|---|
| Peptid P467-CRM197 | Mymetics | n.a. | 140829-1_am | ca. 2.449 mg/mL P467, ca. 1.22 mg/mL CRM197, in 1x PBS/1 mM EDTA. |
| Peptid P647-CRM197 | Mymetics | n.a. | 140829-2_am | ca. 2.449 mg/mL P647, ca. 1.22 mg/mL CRM197, in 1x PBS/1 mM EDTA. |
| 10x Tris/Glycine/SDS | BioRad | 161-0732 | 116812 | |
| 4x Laemmli Sample Buffer | BioRad | 161-0747 | 350002344 | |
| Precision Plus Protein™ Dual Extra Standards | BioRad | 161-0377 | 310013154 | (2-250 kD), 9 blue-stained bands, and 3 pink reference bands (2, 25, 75 kD) |
| 4-20% Mini-PROTEAN® TGX™ Gel | BioRad | 456-1095 | 400093571 | 12 well, 20 μl |
| Trans-Blot® Turbo™ Mini Nitrocellulose Transfer Packs. | BioRad | 170-4158 | 400093907 | 7 × 8.5 cm, precut blotting transfer pack |
| Anti-P4/P6/P7 mouse serum, D pool | Univ Vienna | n.a. | n.a. | Mouse serum from immunisation with peptides integrated in influenza virosomes |
| anti-mouse IgG HRP | KPL | 074-1802 | 101080 | |
| TMB substrate solution | Seramun | S-002-4 TMB | | |
| 20x Modified Dulbecco's PBS Buffer | Thermo Fisher Scientific | 0028344 | PG201076 | 1 L if 1x PBS prepared with MilliQ water, 140902-am |
| Reducing Agent: β-ME | Sigma | 63689 | n.a. | 14.3M solution |
| WFI | Berna Biotech | 100605 | 1004241 | |
| Tween 20 | Sigma | P9416 | n.a. | |
| PBST | Mymetics | n.a. | 140903 | PBS + 0.05% Tween 20 |
| MPBST | Mymetics | n.a. | 140903 | 5 g milk powder in 100 mL PBST (5%) |
| MPBS | Mymetics | n.a. | 140903 | 5 g milk powder in 100 mL PBS (5%) |

Procedure

One SDS-PA gel was prepared as follows:

All solutions comprising CRM197, fusion peptide-CRM197 conjugates or unconjugated fusion peptides were diluted to 1 mg/mL in PBS at pH 7.4. In total, 36 μL of every sample were prepared, and 15 μL were loaded per lane. The distribution of samples in Gel 1 and Gel 2 is summarised in Table 7, below:

TABLE 7

| | Proben Beschrelbung | WFI [μL] | Probe [μL] | LDS 4x Buffer [μL] | Reducing Agent [μL] |
|---|---|---|---|---|---|
| 1 | Precision Plus Protein ™ Dual Xtra | — | 10 | — | — |
| 2 | CRM197 - 0.2 ug | 25.5 | 0.5 | 9 | 1 |
| 3 | CRM197 - 0.4 ug | 25.0 | 1.0 | 9 | 1 |
| 4 | CRM197 - 0.8 ug | 24.0 | 2.0 | 9 | 1 |
| 5 | P467-CRM197 - 0.2 ug | 25.5 | 0.5 | 9 | 1 |
| 6 | P467-CRM197 - 0.8 ug | 24.0 | 2.0 | 9 | 1 |
| 7 | P647-CRM197 - 0.2 ug | 25.5 | 0.5 | 9 | 1 |
| 8 | P647-CRM197 - 0.8 ug | 24.0 | 2.0 | 9 | 1 |
| 9 | P467 - 0.2 ug | 25.5 | 0.5 | 9 | 1 |
| 10 | P467 - 0.8 ug | 24.0 | 2.0 | 9 | 1 |
| 11 | P647 - 0.2 ug | 25.5 | 0.5 | 9 | 1 |
| 12 | P647 - 0.8 ug | 24.0 | 2.0 | 9 | 1 |

Results

Western Blot—

After electrophoresis, the gel was removed from the cassette, and rinsed shortly in Milli Q water. A transfer sandwich was prepared in accordance with the manufacturer's instructions (BioRad) and installed in a Turbo Transfer Blot machine. Following transfer, the nitrocellulose membrane was controlled for the complete presence of the prestained marker proteins. Only minimal amounts of marker remained visible in the SDS PA gel. The nitrocellulose membrane was then incubated in 5% milk in phosphate-buffered saline with Tween 20 (MPBST) for 1 hr at RT.

Mice serum Pool D was diluted 1:500 in MPBST, and incubated on the membrane for 1 hr at RT. The membrane was then washed thrice with 1×MPBST for 5 min each and then incubated with anti-mouse IgG (KPL, 074-1802; Ab20), diluted 1:5000 in MPBST, for 30 min at RT. The membrane was then washed thrice with 1×MPBST for 5 min each and developed with TMB solution for 10 min at RT.

Conclusions

The immunoblot with the used antiserum D showed reactivity with the CRM197-fusion peptide conjugates only. No cross-reactivity was observed with unconjugated CRM197. These results indicated that a significant amount of fusion peptide was conjugated to the carrier protein, and confirm that the observed shift in migration in the gel for the CRM197-fusion peptide conjugates is due to the conjugation of the fusion peptides to the carrier protein, and not to CRM197 intermolecular cross-linking. A signal attributed to free unconjugated fusion peptides was detected, either because the antiserum does not react with them, or because the fusion peptides migrated to the bottom of the gel and were not transferred to the nitrocellulose membrane.

Antiserum D reacted slightly stronger with the P647-CRM197 conjugate than with the P467-CRM197 conjugate. The results suggested that the antiserum reacted strongly with the conjugated fusion peptides than with the free fusion peptides.

Example 4—P467-CRM197 and P647-CRM197 Spot Blot

The presence of the fusion peptides P467 and P647 on the CRM197 carrier protein was also confirmed in a spot blot experiment using antiserum D.

Samples

CRM197, 1 mg/mL in PBS pH 7.4;
P467 antigen, 1 mg/mL in PBS pH 7.4;
P647 antigen, 1 mg/mL in PBS pH 7.4;
P467-CRM197, 1 mg/mL in PBS pH 7.4 (calculated concentration); and
P647-CRM197, 1 mg/mL in PBS pH 7.4 (calculated concentration).

TABLE 8

Material

| Product | Supplier | Prod. No. | Lot No | Comments |
|---|---|---|---|---|
| Peptide P647 (before lipid conjugation) | Bachem | 4086800 | 88800/1K | MW = 5498 Da; 49 ea, pl = 4.7 PESFDGDPASNTAPLQPRVLQGL PREYVNARHSLPYMPIWKFPDEE GAC |
| Peptide P647 (before lipid conjugation) | Bachem | 4088709 | 88799/1K | MW = 5287 Da; 47 ea, pl = 4.7 RVLQGLPREYVNARHS PESFDGDPASNTAPLQP YMPIWKFPDEEGAC |
| CRM197 Diphteria Toxin nontoxic mutant | Merck (Calbiochem) | 322327 | D00149725 | 1 mg aliquots. 2 mg/mL solution in PBS pH 7.4 after reconstitution; MW - 58-63 kDa; pl = 5.85, 39 Lys redisdues |
| Peptid P467-CRM197 | Mymetics | n.a. | 140829-1_am | ca.2.449 mg/mL P467, ca. 1.22 mg/mL CRM197, in 1x PBS/1 mM EDTA. |
| Peptid P647-CRM197 | Mymetics | n.a. | 140829-2_am | ca.2.449 mg/mL P647, ca. 1.22 mg/mL CRM197, in 1x PBS/1 mM EDTA. |

TABLE 8 -continued

| | | Material | | |
|---|---|---|---|---|
| Product | Supplier | Prod. No. | Lot No | Comments |
| Nitrocellulose membrane | Thermo Fisher/ Pierve | 88025 | PE1844001 | 0.45 μm, 8 cm × 8 cm |
| Anti-P4/P6/P7 mouse serum, D pool | Univ Vienna | n.a. | n.a. | Mouse serum from immunisation with peptides integrated in influenza virosomes |
| anti-mouse IgG HRP | KPL | 074-1802 | 101080 | |
| TMB substrate solution | Seramun | S-002-4 TMB | | |
| 20x Modified Dulbecco's PBS Buffer | Thermo Fisher Scientific | 0028344 | PG201076 | 1 L if 1x PBS prepared with MilliQ water, 140902-am |
| WFI | Berna Biotech | 100605 | 1004241 | |
| Tween 20 | Sigma | P9416 | n.a. | |
| PBST | Mymetics | n.a. | 140903 | PBS + 0.05% Tween 20 |
| MPBST | Mymetics | n.a. | 140903 | 5 g milk powder in 100 mL PBST (5%) |
| MPBS | Mymetics | n.a. | 140903 | 5 g milk powder in 100 mL PBS (5%) |
| Low-fat milk powder | Migros | n.a. | n.a. | |

Procedure

A pre-cut nitrocellulose membrane was used and lines were drawn with a pencil. Two-fold dilutions of each sample were performed in PBS at pH 7.4 in Eppendorf tubes, starting at 1 mg/mL (1 μg/μL). Theoretical concentrations per spot (1 μL) were 1 μg/500 ng/250 ng/125 ng/62.5 ng/31.25 ng. For each spot, approximately 1 μL of each sample was transferred to the membrane (in duplicates), as outlined below:

Line A CRM197;
Line B P467 antigen (free fusion peptide without lipid conjugation);
Line C P647 antigen (free fusion peptide without lipid conjugation);
Line D P467-CRM197 (starting with 1 μg of fusion peptide, and 0.5 μg of CRM197); and
Line E P647-CRM197 (starting with 1 μg of fusion peptide, and 0.5 μg of CRM197)

The membrane was allowed to dry on air for 10 min at RT and subsequently blocked with 5% milk in PBST (MPBST) for 30 min at RT. The membrane was then incubated with primary antibody (mouse antiserum Pool D, diluted 1:500 in MPBST) for 1 r at RT. The membrane was then washed thrice with MPBST for 5 min each and then incubated with secondary antibody (anti-mouse IgG; KPL, 074-1802; Ab20; diluted 1:5000 in MPBST) for 30 min at RT. Following this incubation, the membrane was washed thrice with MPBST for 5 min each and then incubated with TMB solution at RT for approx 3 min, followed by a wash with Milli Q water before drying.

Conclusions

The spot blot with the mouse antiserum D showed reactivity with the CRM197-fusion peptide conjugates only. There was minimal cross-reactivity with unconjugated CRM197 protein. As the amount of CRM197 in the conjugates was about 50% compared to the amount of fusion peptide, the minimal background in this sample was likely due to the cross-reactivity with the diphtheria toxin variant.

The free (unconjugated) fusion peptides (fusion peptides without lipid conjugate) gave a signal with the antiserum only in the case of P647, but not with P467. The reason for this is not immediately clear. However, in the first sample dilutions of P647, the signal was somewhat weaker than in the following dilutions. This may indicate the presence of an inhibitor to the antibody binding site, or reduced binding to the nitrocellulose membrane. The nature of this inhibitor is unknown, but it may be attributable to DMSO that was originally used to prepare the high concentration stock of the fusion peptide (10 mg/mL).

The mouse antiserum D reacted very strong with the P467-CRM197 and P647-CRM197 conjugates, confirming the conjugation of most of the fusion peptides to the carrier protein.

Due to the unequal antiserum reactivity of the free fusion peptides as compared to the fusion peptide-CRM197 conjugates, it was not possible to quantitate the amount of antigen. However, as no purification steps were applied following the conjugation reaction, it is acceptable to calculate with the theoretical starting concentrations for the fusion peptides.

In summary, the results suggest that the antiserum reacted strongly with the conjugated fusion peptides than with the free fusion peptides.

Example 5—Sample Preparation for Dose-Titration Studies in Mice

The following describes the preparation of fusion peptide-CRM197 conjugates for dose-titration experiments in mice.

TABLE 9

| Material | | | | |
|---|---|---|---|---|
| Product | Supplier | Prod. No. | Lot No | Comments |
| Peptide P647 (before lipid conjugation) | Bachem | 4086800 | 88800/1K | MW = 5498 Da; 49 ea, pl = 4.7 PESFDGDPASNTAPLQPRVLQGL PREYVNARHSLPYMPIWKFPDEE GAC |
| Peptide P647 (before lipid conjugation) | Bachem | 4088709 | 88799/1K | MW = 5287 Da; 47 ea, pl = 4.7 RVLQGLPREYVNARHS PESFDGDPASNTAPLQP YMPIWKFPDEEGAC |
| CRM197 Diphteria Toxin nontoxic mutant | Merck (Calbiochem) | 322327 | D00149725 | 1 mg aliquots. 2 mg/mL solution in PBS pH 7.4 after reconstitution; MW - 58-63 kDa; pl = 5.85, 39 Lys redisdues |
| Peptid P467-CRM197 | Mymetics | n.a. | 140829-1_am | ca.2.449 mg/mL P467, ca. 1.22 mg/mL CRM197, in 1x PBS/1 mM EDTA. |
| Peptid P647-CRM197 | Mymetics | n.a. | 140829-2_am | ca.2.449 mg/mL P647, ca. 1.22 mg/mL CRM197, in 1x PBS/1 mM EDTA. |
| 20x Modified Dulbecco's PBS Buffer | Thermo Fisher Scientific | 0028344 | PG201076 | 1 L if 1x PBS prepared with MilliQ water, 140902-am |
| WFI | Berna Biotech | 100605 | 1004241 | |

Procedure

For the preparation of samples for animal studies, the conjugate reaction solutions were diluted to a defined target concentration. For the following preparations, it was assumed that the conjugation efficiency of the peptide to the protein was at least 90%.

Sample Preparation for the High Dose Groups (Group 1):

These samples were expected to contain approximately 420 µg of conjugated fusion peptide per tube (1.2 mg/mL):
Tube 1:
1045 µL of P467-CRM197
880 µL of (1x) PBS pH 7.4
This solution was mixed well, and 350 µL was transferred to five glass vials (2.5 mL each) and labelled as follows: P467-CRM197; Group 1—High Dose; Estimated P467 conc: ~1.2 mg/mL; Lot 140903-1_am.
Tube 2:
1045 µL of P647-CRM197 (strongly vortexed before pipetting)
880 µL of (1x) PBS pH 7.4
This solution was mixed well, and 350 µL was transferred to five glass vials (2.5 mL each) and labelled as follows: P647-CRM197; Group 1—High Dose; Estimated P647 conc: ~1.2 mg/mL; Lot 140903-4_am.

Sample Preparation for the Medium Dose Groups (Group 2):

These samples were expected to contain approximately 210 µg of conjugated fusion peptide per tube (0.6 mg/mL):
Tube 1:
525 µL of P467-CRM197
1400 µL of (1x) PBS pH 7.4
This solution was mixed well, and 350 µL each was transferred to five 2.5 mL glass vials and labelled as follows: P467-CRM197; Group 2—Medium Dose; Estimated P467 conc: ~0.6 mg/mL; Lot 140903-2_am.
Tube 2:
525 µL of P647-CRM197 (strongly vortexed before pipetting)
1400 µL of (1x) PBS pH 7.4
This solution was vortexed well, and 350 µL was transferred to five 2.5 mL glass vials and labelled as follows: P647-CRM197; Group 2—Medium Dose; Estimated P647 conc: ~0.6 mg/mL; Lot 140903-5_am.

Sample Preparation for the Low Dose Groups (Group 3):

These samples were expected to contain approximately 105 µg of conjugated fusion peptide per tube (0.3 mg/mL):
Tube 1:
262 µL of P467-CRM197
1663 µL of (1x) PBS pH 7.4
This solution was mixed well and 350 µL each was transferred to five 2.5 mL glass vials and labelled as follows: P467-CRM197; Group 3—Low Dose; Estimated P467 conc: ~0.3 mg/mL; Lot 140903-3_am.
Tube 2:
262 µL of P647-CRM197 (strongly vortexed before pipetting)
1663 µL of (1x) PBS pH 7.4
This solution was vortexed well, and 350 µL each was transferred to five 2.5 mL glass vials and labelled as follows: P647-CRM197; Group 3—Low Dose; Estimated P467 conc: ~0.3 mg/mL; Lot 140903-6_am.

Example 6—Immunisation Studies

Peptide Antigens

Two fusion peptides, P467 (SEQ ID NO:8) and P647 (SEQ ID NO:9) were synthetized at Bachem (Switzerland). Both hybrids were coupled to virosomes (viral envelopes from inactivated influenza virus A/Brisbane/59/2007) which are suitable as an antigen delivery system and do not require additional adjuvants. Three concentrations, calculated for the amount of the fusion peptide, were tested: 15 µg, 30 µg and 50 µg per injection. For comparison, both fusion peptides were coupled to CRM197 and used in a head-to-head experiment at a concentration 30 µg per injection. All conjugation procedures (CRM and virosomes) were carried out at Mymetics (Switzerland).

The virosomal formulations were delivered frozen and formed a cloudy suspension after thawing.

After coupling, the CRM-P647 conjugate was received as a precipitated formulation, whereas CRM-P467 remained soluble in water based buffer.

The three Her-2/neu-derived B cell epitopes P4 (SEQ ID NO:3), P6 (SEQ ID NO:1) and P7 (SEQ ID NO:2) were synthetized and coupled to KLH (keyhole limpet hemocyanin) at piChem (Austria) and were used as coating antigens to evaluate antibody responses to single peptides by ELISA.

To evaluate antibody responses directed to the unconjugated fusion peptides, P467 and P647 were used as coating antigens in the ELISA assays.

Immunisation Protocol

Female Balb/C mice were immunised subcutaneously in 2-3 weeks intervals according to the following study design:

Groups receiving virosomal conjugates were primed once with inactivated influenza virus (Inactivated A/Brisbane/59/2007). Immunisations with conjugated constructs started 16 days after the priming. All virosomal formulations were delivered ready to use and were applied without any additives 100 µl per injection.

Stocks of CRM-fusion peptide conjugates were diluted with NaCl solution and mixed with aluminium hydroxide gel suspension prior to administration by injection. CRM-P647 (precipitated) was vortexed and the suspension was used in the same way as CRM-P467.

Control groups received empty virosomes (TIRIV) or NaCl solution plus aluminium hydroxide.

Animals 60 female Balb/C mice, 6-8 weeks at delivery (29 Oct. 2014), origin: Charles River, Germany.

10 groups: n=5 mice per group—Animal facility: General Hospital Vienna/Biomedical Unit.

Groups

Group A—empty virosomes (TIRIV)—100 µl/mouse;
Group B—P467-virosomes—50 µg/mouse in 100 µl;
Group C—P467-virosomes—30 µg/mouse in 100 µl;
Group D—P467—virosomes—15 µg/mouse in 100 µl;
Group E—P647-virosomes—50 µg/mouse in 100 µl;
Group F—P647-virosomes—30 µg/mouse in 100 µl;
Group G—P647-virosomes—15 µg/mouse in 100 µl;
Group H—NaCl+aluminium hydroxide (control)—100 µl/mouse;
Group I—P467-CRM+aluminium hydroxide—30 µg/mouse in 150 µl; and
Group J—P647-CRM+aluminium hydroxide—30 µg/mouse in 150 µl.

Blood was taken prior to immunisation, three weeks after the $2^{nd}$ immunisation, two weeks after the $3^{rd}$ immunisation and two weeks after the $4^{th}$ immunisation. The blood samples were then analysed for:

Peptide-specific antibody titres (IgG);
Construct specific antibody titres (IgG);
Antibody titres specific to recombinant extracellular Her-2/neu (IgG); and
Specificity to the native Her-2/neu expressed in SKBR-3 cancer cells.

ELISA Protocols

1) Peptide-Specific ELISA

Microtitre plates were coated with KLH-fusion peptide conjugates at 0.5 µg/well. For background estimation, wells were coated with KLH alone. After blocking, diluted sera were added. Bound IgG was detected with HRP-labelled antibody (Rabbit anti mouse IgG POX, Fc fragment specific, Nr: 315-035-008; Jackson Immuno Research) and subsequent TMB staining. Plates were read after adding stop solution at 450 vs 630 nm.

(2) Fusion Peptide-Specific ELISA

The non-modified fusion peptides P467 and P647 were used as coating antigens at a concentration of 0.5 µg/well in carbonate buffer. Diluted sera were then added and analysed as described in the peptide-specific protocol, above.

(3) Extracellular Her-2/neu-Specific-ELISA

A fusion protein comprising the recombinant extracellular domain of human Her-2/neu (amino acid residues 23-652 of Her2/neu) and the Fc region of human IgG1 (ErbB2/Fc Chimera, cat. No #1129-ER R&D Systems) was used as a coating antigen. Plates were coated with 0.1 µg/well of protein and 0.1% BSA for background estimation. Diluted sera were then added and analysed, as described above, after subtracting the background signal from the BSA-only wells.

(4) Her-2/Neu-Specific Cell Assay Using SKBR3-Cells

The human breast cancer cell line SKBR-3 (HTB30, ATCC, USA) overexpressing Her-2/neu was used as a source of native Her2/neu protein. Cells were harvested three days after passaging and stored at −80° C. Cell lysis was performed as previously described in Godell V and Disis M L *J. Immunol. Meth* (2005), with some minor modifications: Variant 1: plates were coated with the humanized anti-Her-2/neu antibody Herceptin (provided by General Hospital Vienna); Variant 2: plates were coated with the humanized anti-Her-2/neu antibody Perjeta (provided by General Hospital Vienna). Protein content in cell lysates was quantified with the Pierce BCA Protein Assay Kit #23227 directly before use. Lysates were diluted to a concentration 100 µg/well in 1% BSA/PBS. After blocking, the cell lysates were added to the wells. To control for individual background, BSA/PBS was added. For IgG detection, HRP-linked sheep anti-mouse IgG (Amersham/GE Healthcare) was used. TMB staining was performed as above. For each serum sample, the OD value was calculated as the difference between the OD reading of SKBR-3-coated wells minus BSA-coated wells.

Example 7—Peptide-Specific Antibodies

Sera from the final bleed (i.e., after four immunisations) were used. Different dilutions were analysed from sera of virosome and CRM197 immunized mice, as follows:

Groups treated with virosomal formulations: 1:5,000 dilution;
Groups treated with CRM-fusion peptide conjugates: 1:100,000 dilution.

Figure 2:
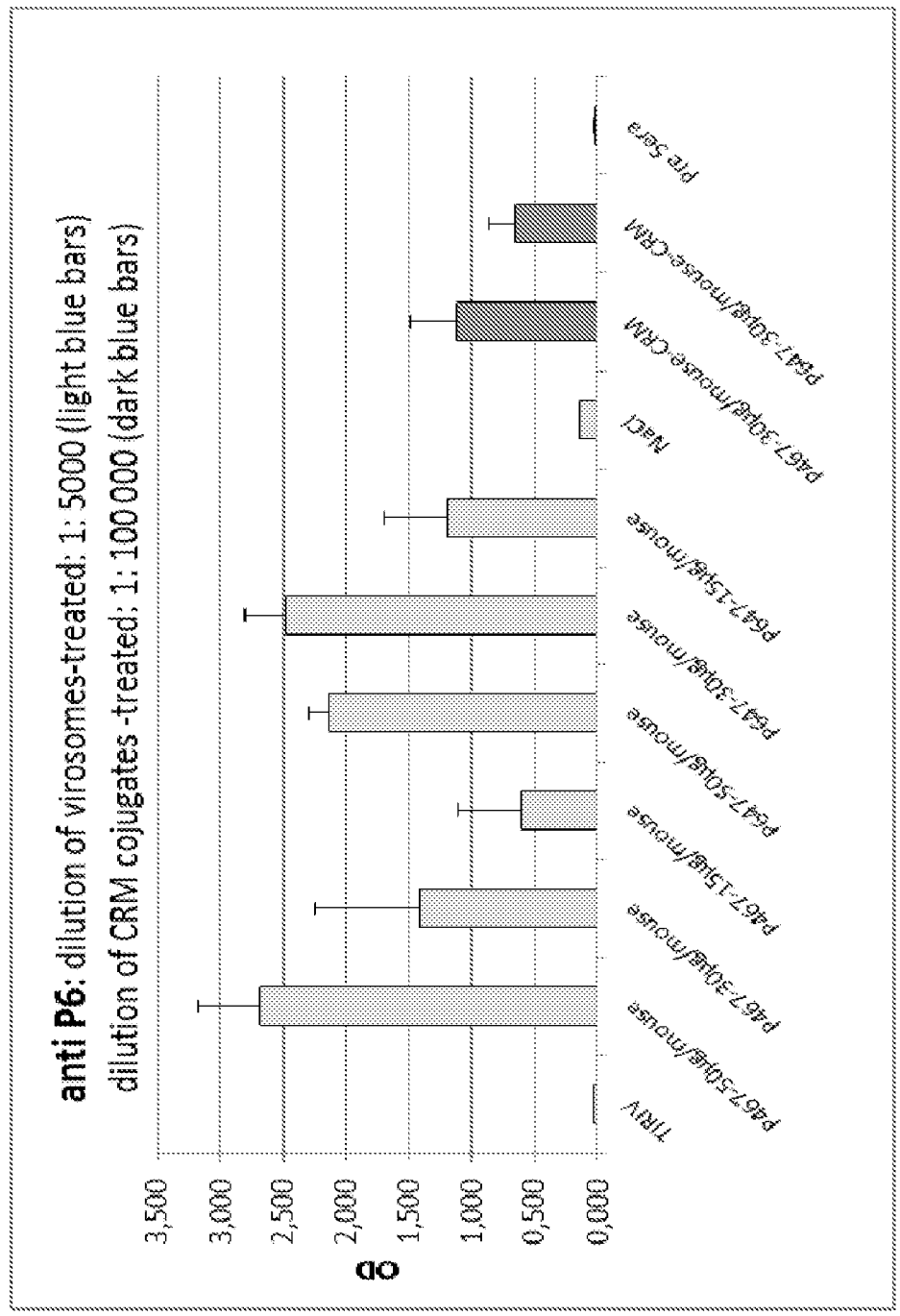
FIG. 2 shows anti-P6 antibody titres in serum samples obtained after the fourth immunisation with either virosomes incorporating the P467 or P647 fusion peptides or CRM197-fusion protein conjugates (CRM). Data are presented as OD values.
Figure 3:
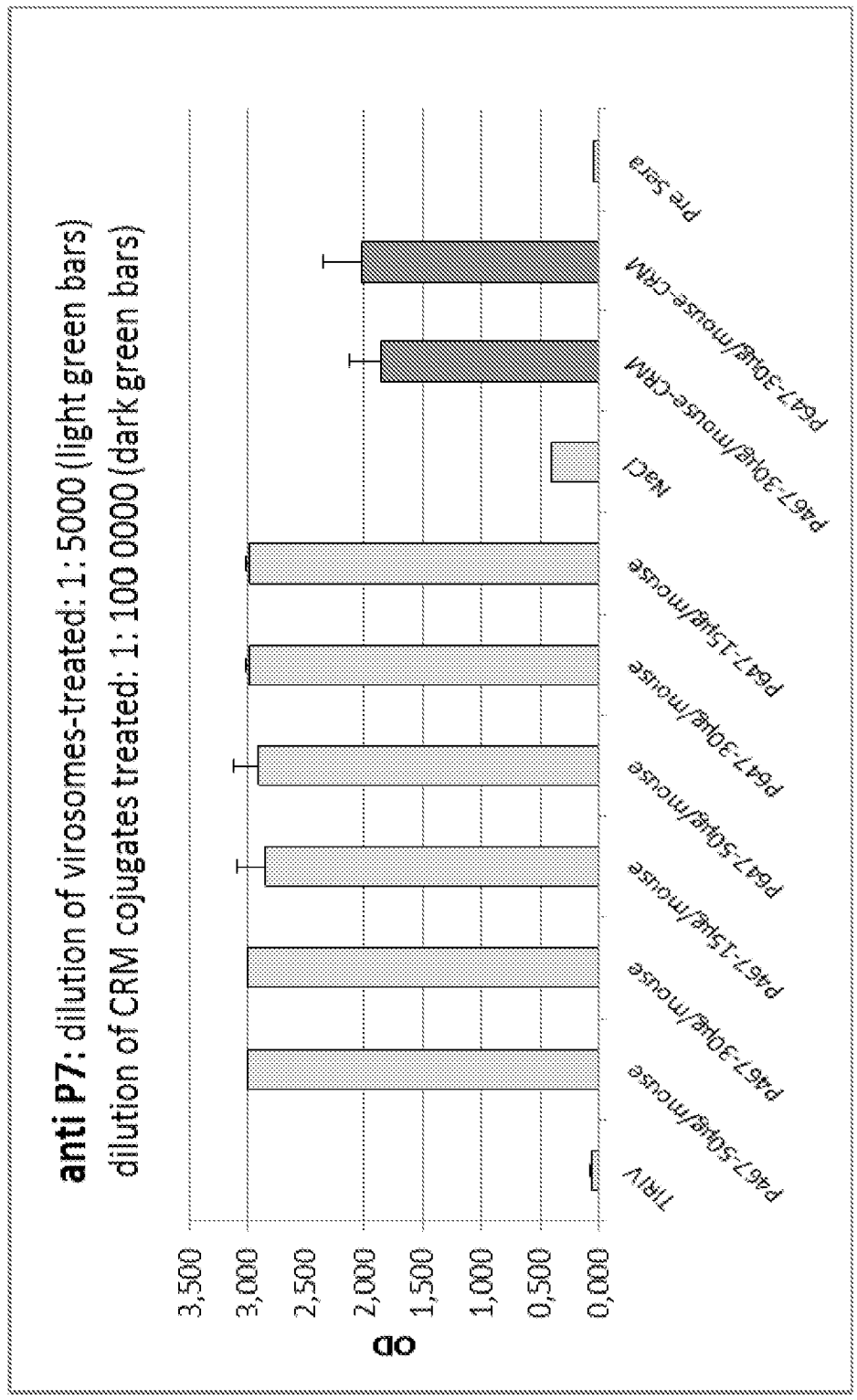
FIG. 3 shows anti-P7 antibody titres in serum samples obtained after the fourth immunisation with either virosomes incorporating the P467 or P647 fusion peptides or CRM197-fusion protein conjugates (CRM). Data are presented as OD values.

Data were depicted in OD values. The background on KLH coated wells was subtracted (see FIGS. 1-3).

Results

Antibodies against all three single peptides were elicited in all treatment groups (Groups B-G and I-J). No peptide-specific antibodies were detected in the control groups (Groups A and H). Remarkable differences in antibody titres were observed.

Four immunisations with the CRM-fusion peptide conjugates induced approximately ten-fold higher antibody titres to all three individual peptides as compared to four immunisations with the corresponding virosomal formulations.

Both constructs (P467 and P647), regardless of coupling partner, induced the highest antibody titre against the P7 B cell epitope (SEQ ID NO:2), while the lowest titres were induced against the P4 B cell epitope (SEQ ID NO:3).

Figure 4:
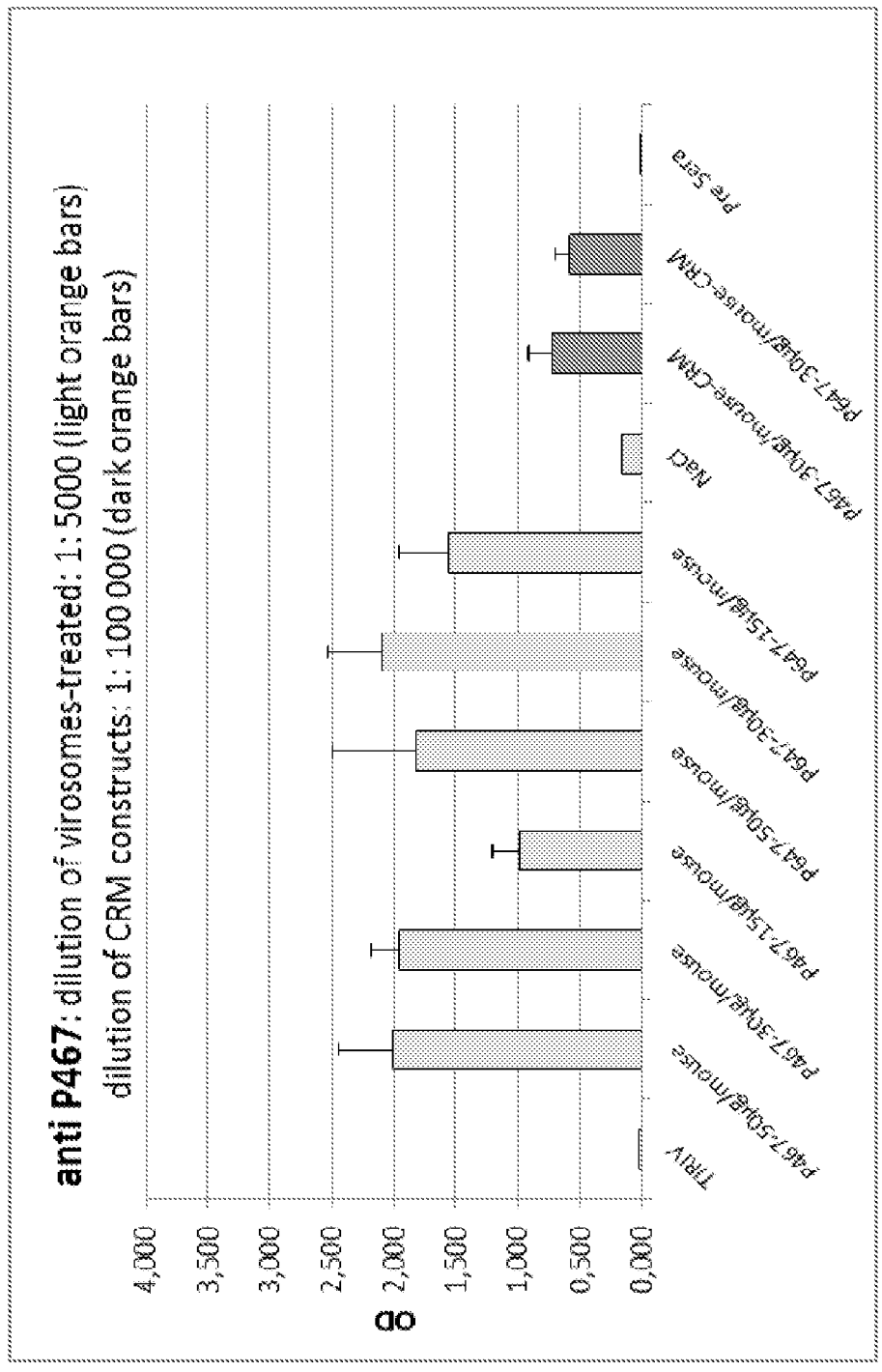
FIG. 4 shows anti-P467 antibody titres in serum samples obtained after the fourth immunisation with either virosomes incorporating the P467 or P647 fusion peptides or CRM197-fusion protein conjugates (CRM). Data are presented as OD values.
Figure 5:
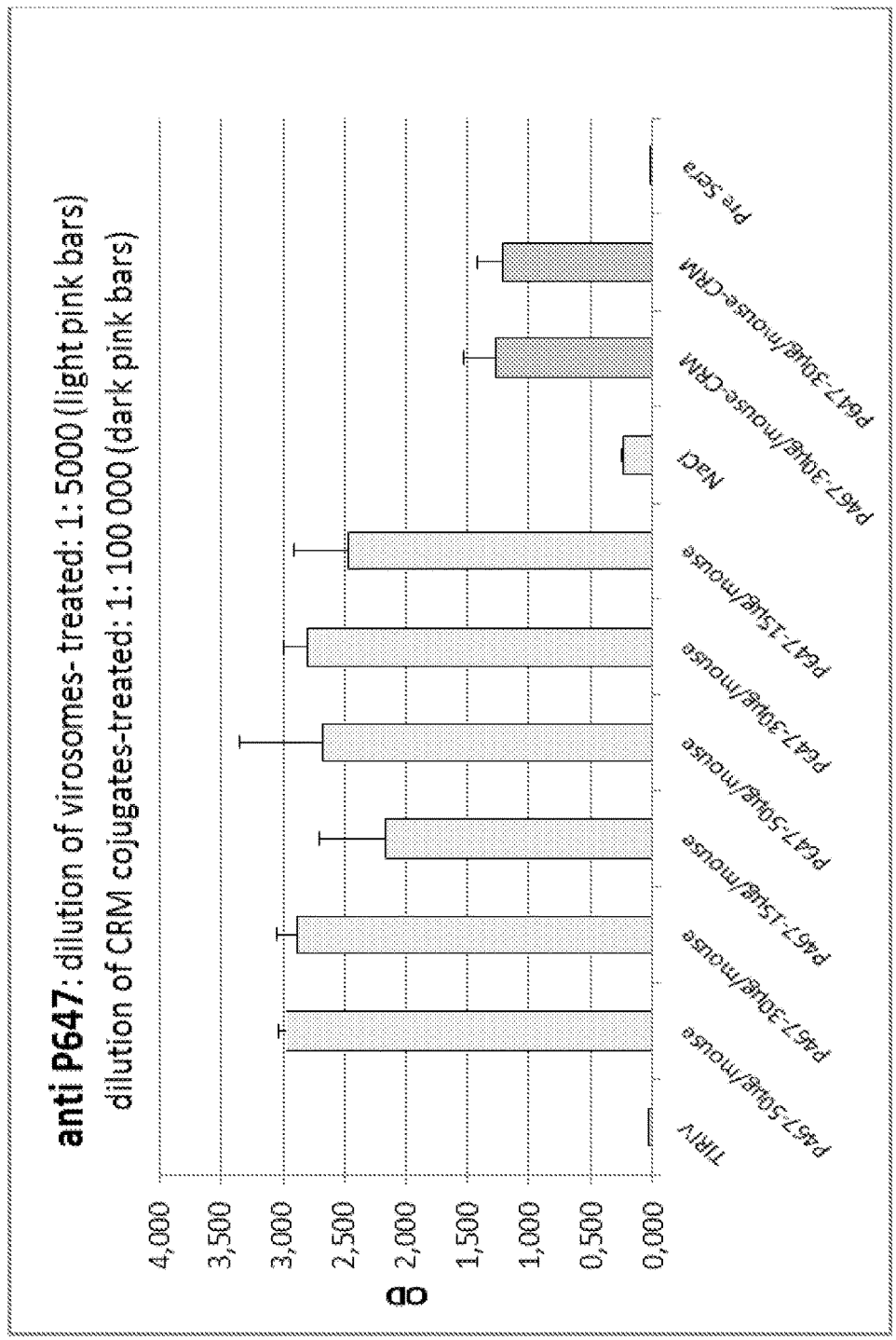
FIG. 5 shows anti-P647 antibody titres in serum samples obtained after the fourth immunisation with either virosomes incorporating the P467 or P647 fusion peptides or CRM197-fusion protein conjugates (CRM). Data are presented as OD values.

As shown in FIGS. 4 and 5, antibodies that bound to the fusion peptides were also produced. These results were derived from experiments in which sera from the final bleed after the fourth immunisation were used. For the groups immunised with virosomes, the sera were diluted 1:5,000. For the groups immunised with the CRM197-fusion peptide conjugates, the sera were diluted 1:100,000. The data depicted in FIGS. 4 and 5 are given in OD values. In line with peptide-specific results shown in FIGS. 1-3, approximately ten-fold higher antibody titres were observed in groups immunised with the CRM197-fusion peptide conjugates as compared to those immunised with the corresponding virosomal formulations. Generally, higher titres were observed for P647 than for P467.

Example 8—Antibody Kinetics in Course of Immunisation with CRM-Conjugates

Figure 6:
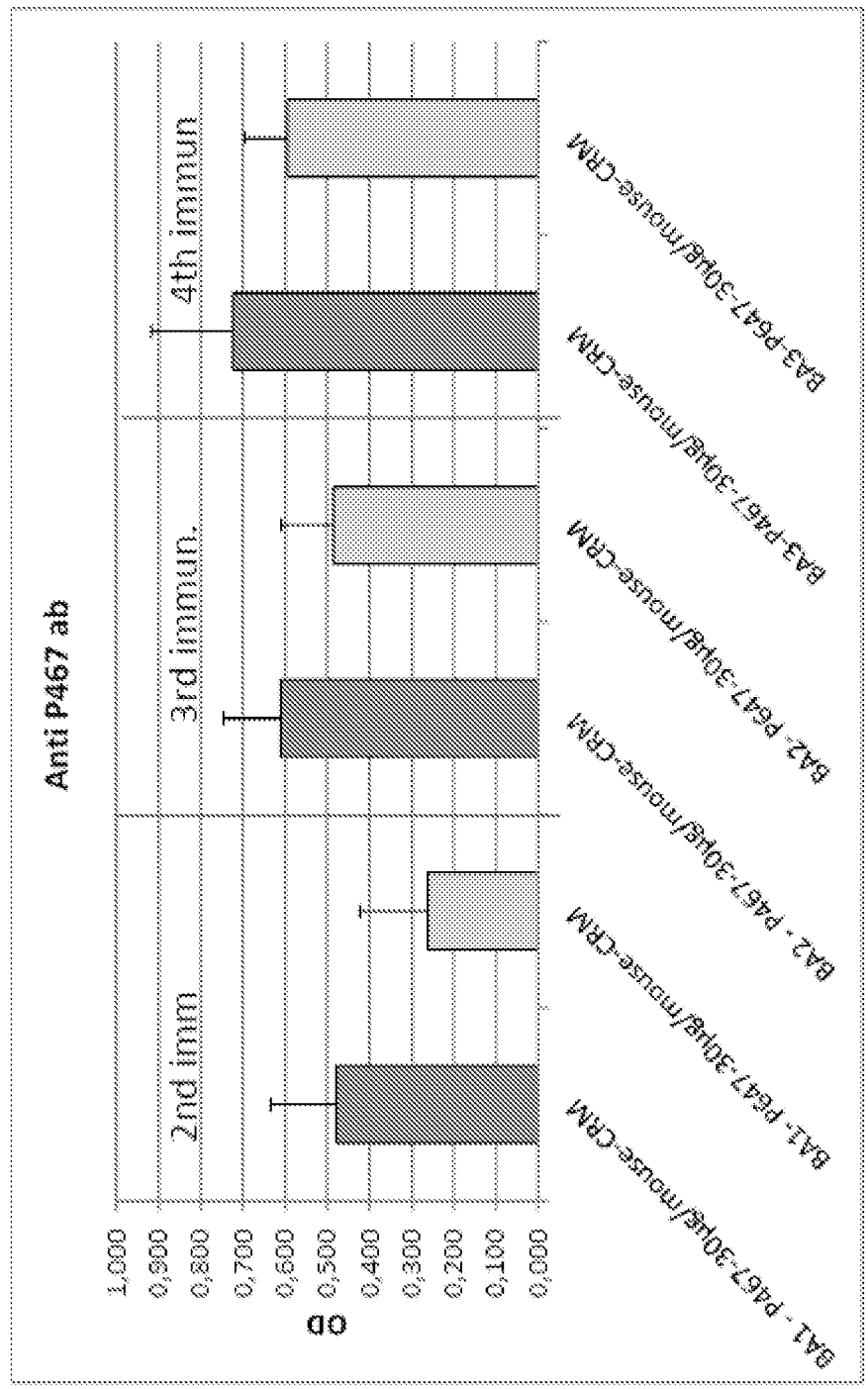
FIG. 6 shows anti-P467 antibody titres in serum samples obtained two weeks after the second (BA1; $1^{st}$ blood draw), third (BA2; $2^{nd}$ blood draw) and fourth (BA3; $3^{rd}$ blood draw) immunisation with either virosomes incorporating the P467 or P647 fusion peptides or CRM197-fusion protein conjugates (CRM). Data are presented as OD values.
Figure 7:
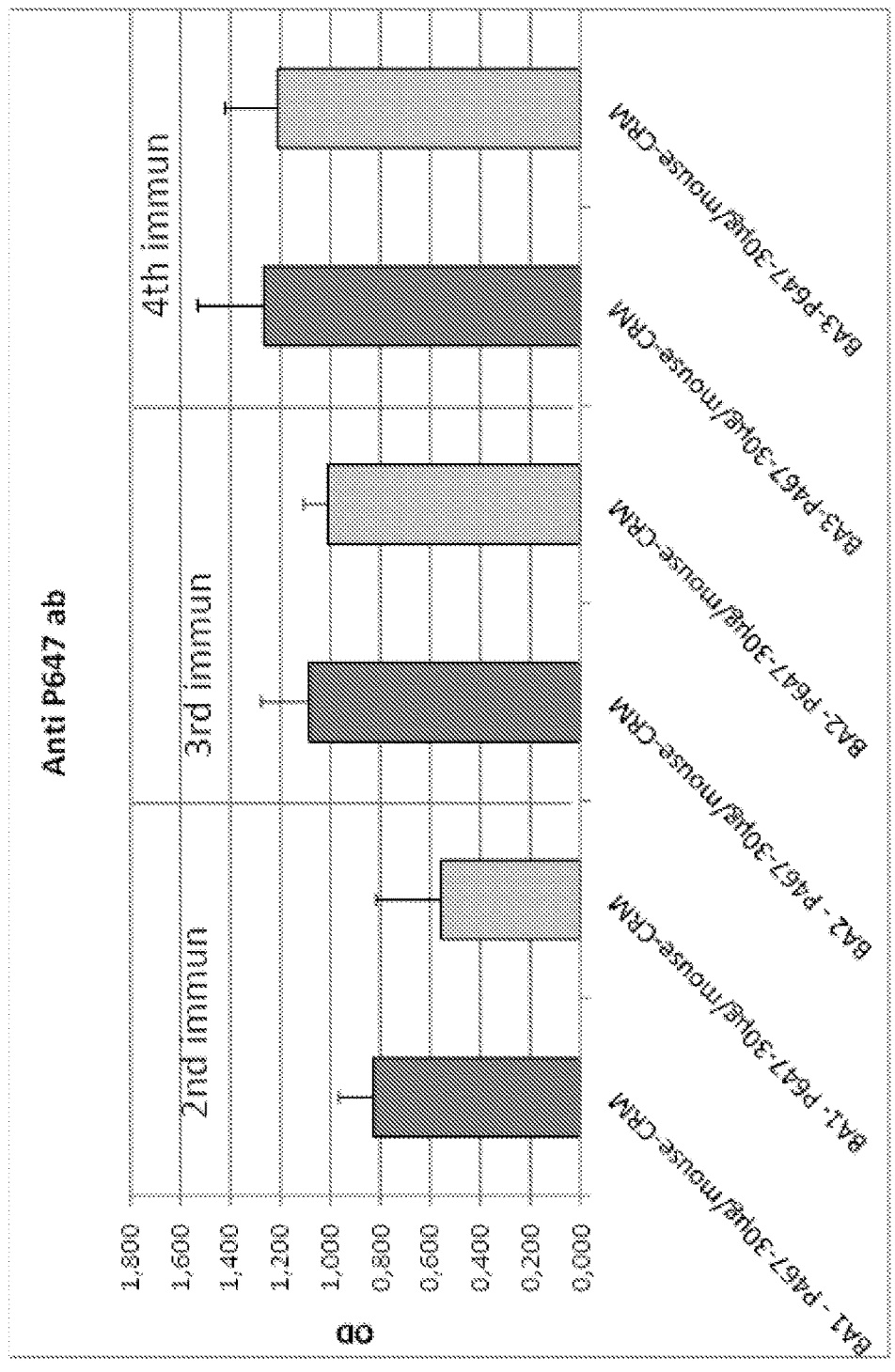
FIG. 7 shows anti-P647 antibody titres in serum samples obtained two weeks after the second (BA1; $1^{st}$ blood draw), third (BA2; $2^{nd}$ blood draw) and fourth (BA3; $3^{rd}$ blood draw) immunisation with either virosomes incorporating the P467 or P647 fusion peptides or CRM197-fusion protein conjugates (CRM). Data are presented as OD values.

Blood was taken two weeks after the $2^{nd}$, $3^{rd}$ and $4^{th}$ immunisations and antibodies specific to both fusion peptides (P467 and P647) were measured (sera were diluted 1:100,000). As shown in FIGS. 6 and 7, fusion protein-specific antibody titres were already quite high after the $2^{nd}$ immunisation and increased slightly after the $3^{rd}$ and $4^{th}$ immunisations. The small increase in fusion protein-specific antibody titres after the $3^{rd}$ and $4^{th}$ immunisations indicate that two or three immunisations (i.e., two or three consecutive doses) with a CRM197-fusion peptide conjugate may be sufficient to generate an effective immune response. (BA1—blood draw after two immunisations; BA2—blood draw after three immunisations; BA2—blood draw after four immunisations).

Example 9—Extracellular her-2/Neu-Specific Antibodies

Blood was taken at two time points; BA1 (blood drawn after two immunisations) and BA2 (blood drawn after three immunisations). Different sera dilutions were analysed—sera from groups immunised with virosomal formulations were diluted 1:400 and sera from groups immunised with CRM-fusion peptide conjugates were diluted 1:2,000. The data depicted in FIG. 8 are OD values.

Figure 8:
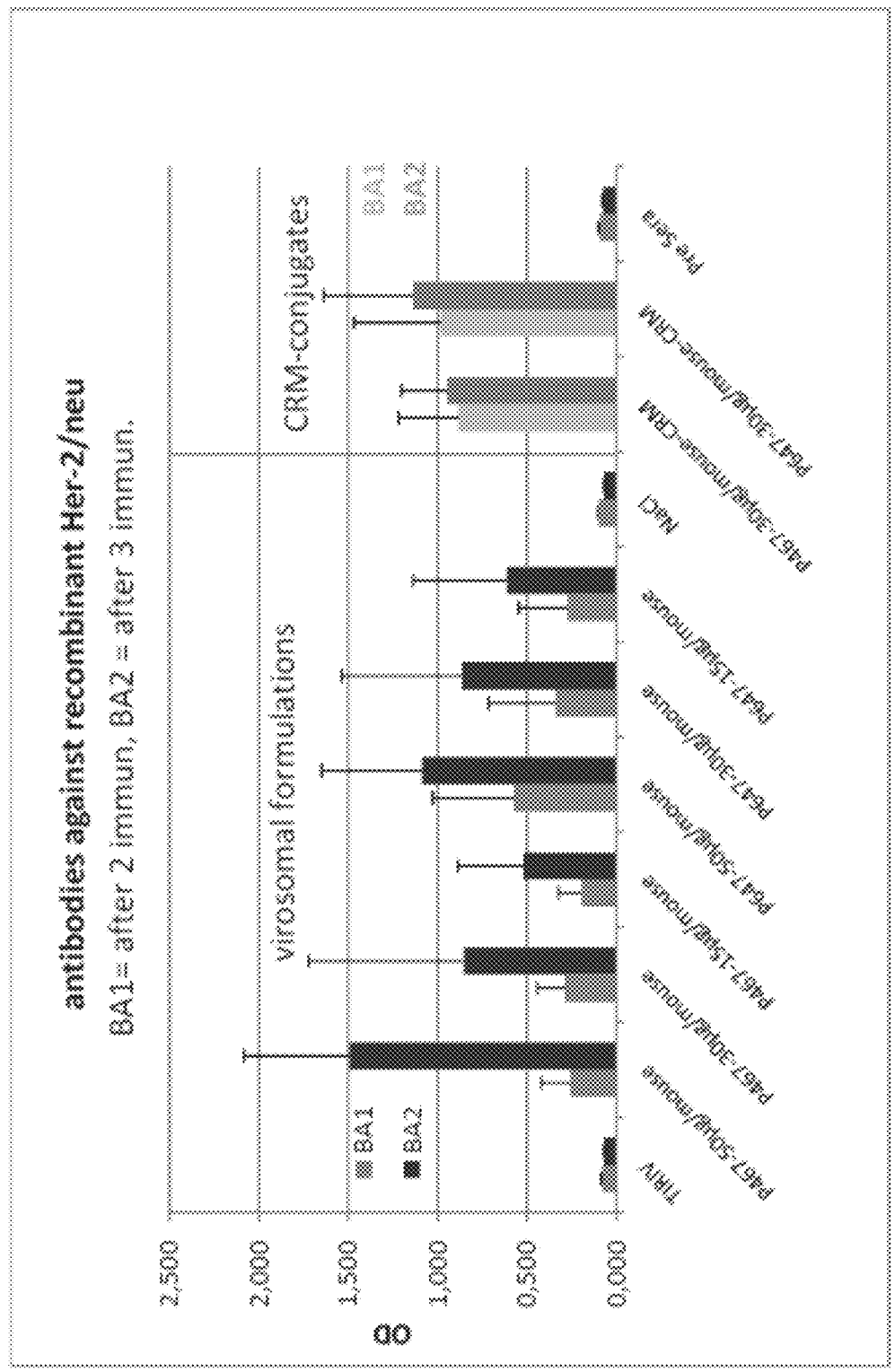
FIG. 8 shows that antibodies from serum samples obtained two weeks after the second (BA1; $1^{st}$ blood draw) and third (BA2; $2^{nd}$ blood draw) immunisation with either virosome formulations incorporating the P467 or P647 fusion peptides (15, 30, 50 µg) or CRM197-fusion protein conjugates (CRM; 30 µg) are capable of binding to a recombinant ECD of Her2/neu. Data are presented as OD values.

As shown in FIG. 8, both fusion peptide-constructs (virosome- and CRM197-conjugated) induced antibodies binding to the recombinant extracellular Her-2/neu protein. No significant Her-2/neu reactivity was observed in sham treated mice and pre-immunisation sera. According to the peptide- and fusion peptide-specific results, significantly higher Her-2/neu specific titres were observed in groups immunized with CRM-fusion peptide conjugates in comparison to virosomal formulations at a 30 µg concentration. A significant antibody titre was also observed after the third immunisation with virosomes. In mice already immunised with CRM-fusion peptide conjugates after the $2^{nd}$ immunisation, the antibody titres were high, which did not markedly increased after the $3^{rd}$ immunisation.

Figure 9:
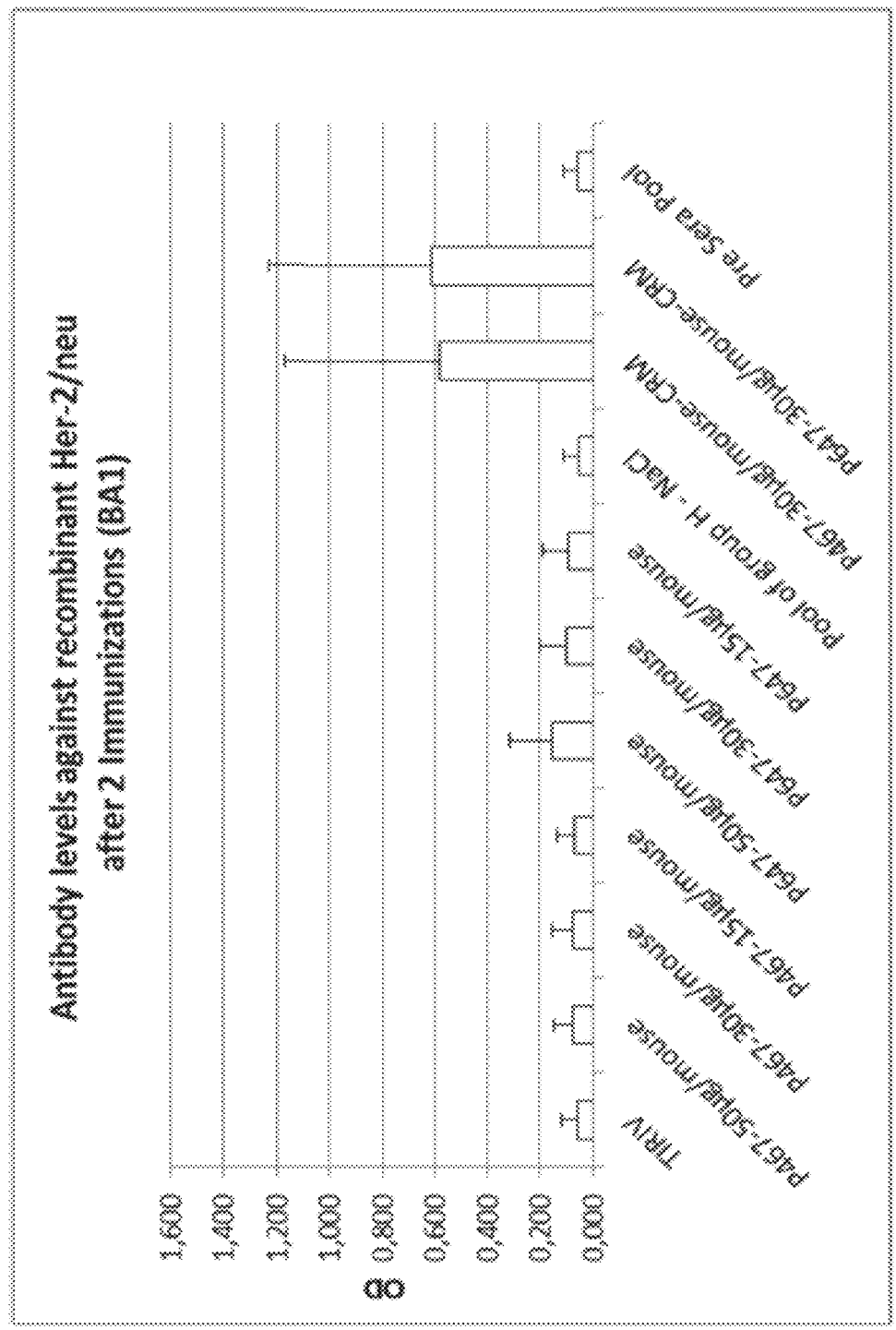
FIG. 9 shows recombinant Her2/neu specific antibodies from serum samples obtained two weeks after the second (BA1; $1^{st}$ blood draw) immunisation with either virosome formulations incorporating the P467 or P647 fusion peptides (15, 30, 50 µg) or CRM197-fusion protein conjugates (CRM; 30 µg). Data are presented as OD values.
Figure 10:
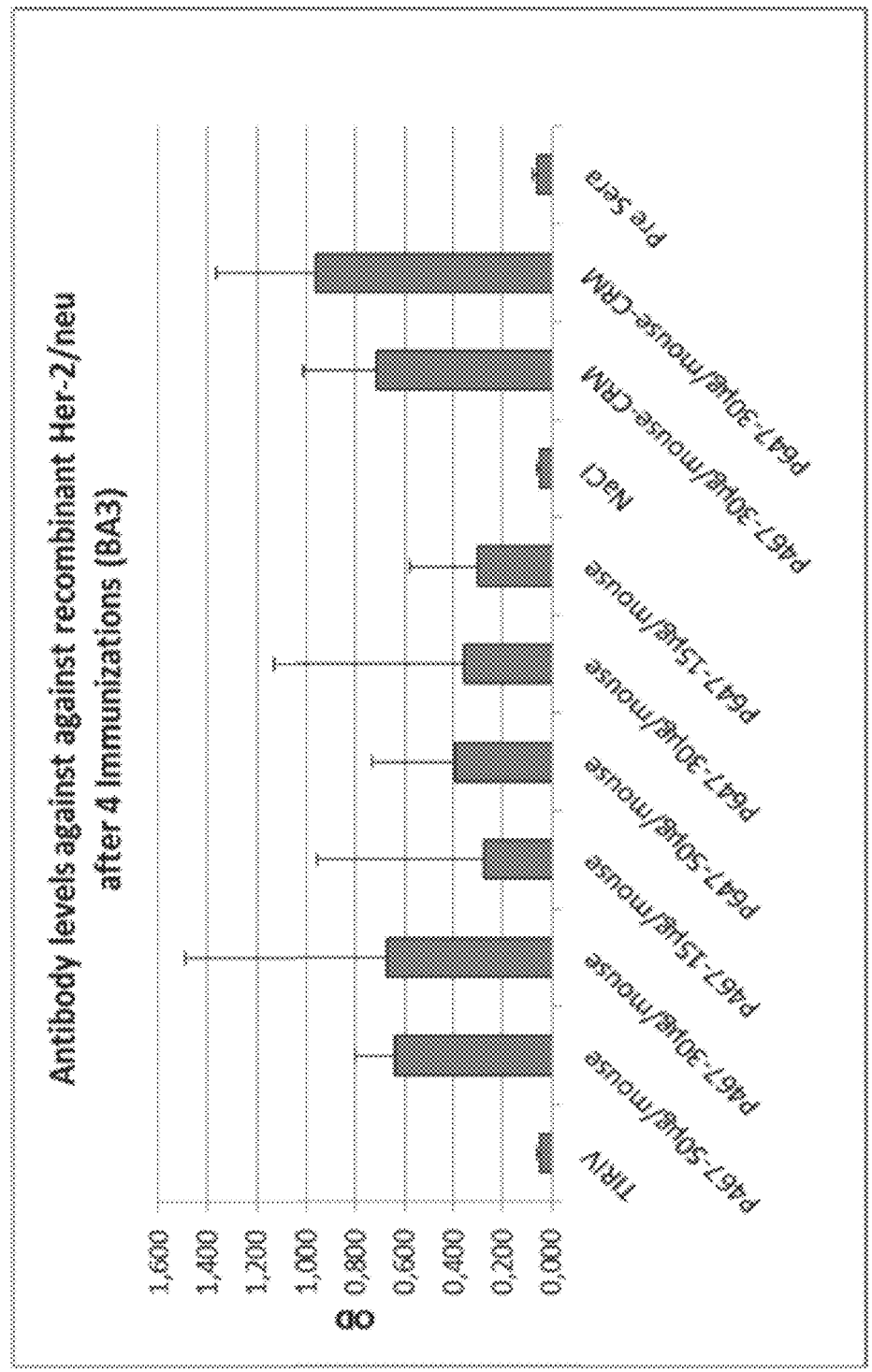
FIG. 10 shows recombinant Her2/neu specific antibodies from serum samples obtained two weeks after the fourth (BA3; $3^{rd}$ blood draw) immunisation with either virosome formulations incorporating the P467 or P647 fusion peptides (15, 30, 50 µg) or CRM197-fusion protein conjugates (CRM; 30 µg). Data are presented as OD values.
Figure 11:
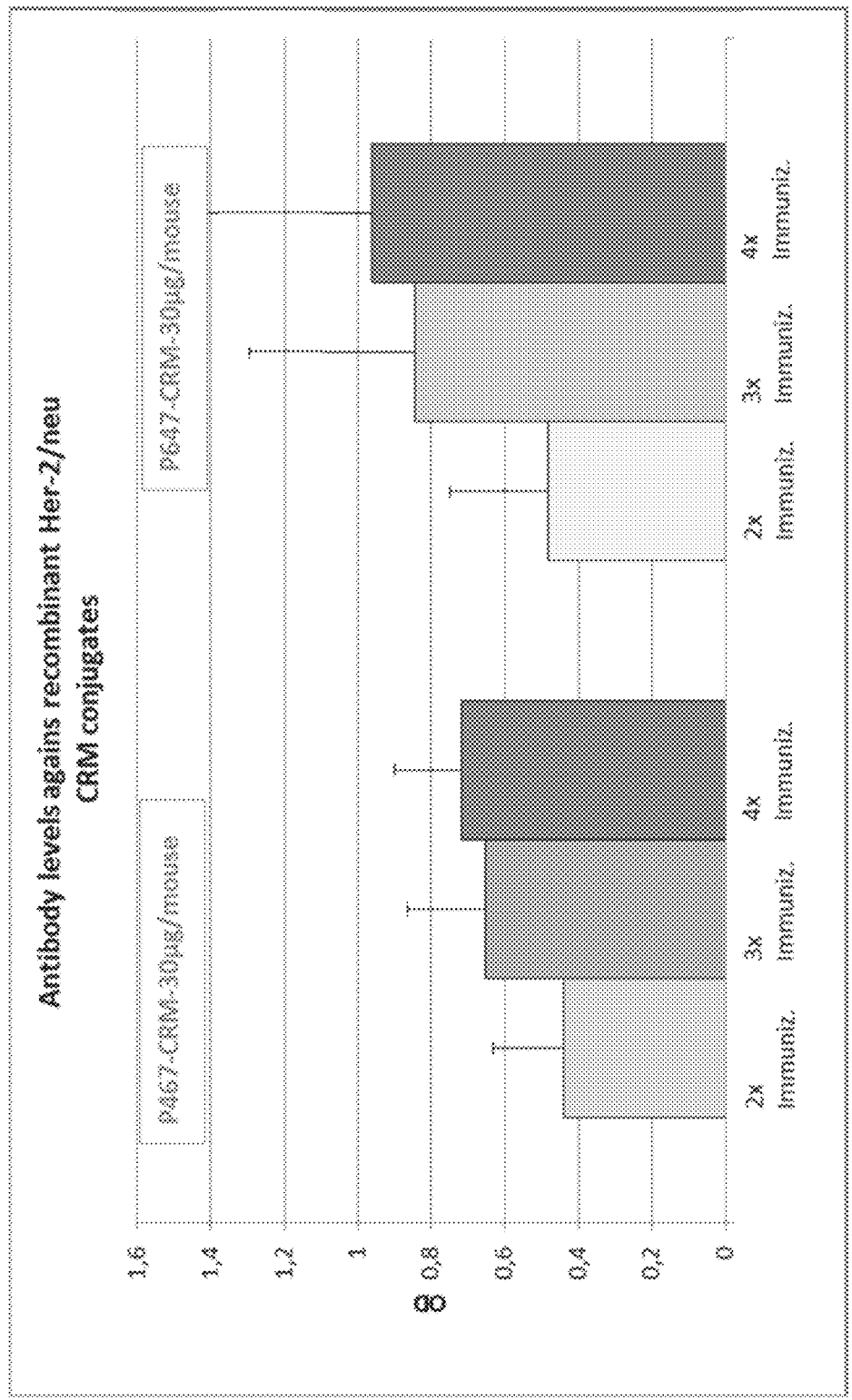
FIG. 11 shows the kinetics of recombinant Her2/neu specific antibody titres after the second, third and fourth immunisations with CRM197-fusion protein conjugates (CRM; 30 µg) comprising the P467 or P647 fusion peptides. Sera were assayed at a dilution of 1:4,000. Data are presented as OD values.

Analysis of sera antibody titres after the $2^{nd}$, $3^{rd}$ and $4^{th}$ immunisations revealed different kinetics of antibody responses with virosome—as compared to CRM-conjugates. After the $2^{nd}$ immunisation (6 weeks after commencement of immunisation) higher antibody titres were observed in animals immunised with CRM-fusion peptide conjugates as compared to virosome conjugates (see FIG. 9). After the 3rd immunisation with the virosome conjugate, a significant increase in antibody titre was observed (see FIG. 8). After the $4^{th}$ immunisation, the Her-2/neu specific antibody titres were comparable between virosome and CRM-immunised mice (see FIG. 10). In mice immunised with the CRM-fusion peptide conjugates, there was a small increase in antibody titre between the $3^{rd}$ and $4^{th}$ immunisation, indicating strong immunogenicity after the $2^{nd}$ immunisation, with even stronger immunogenicity after the $3^{rd}$ immunisation (see FIG. 11).

Figure 12:
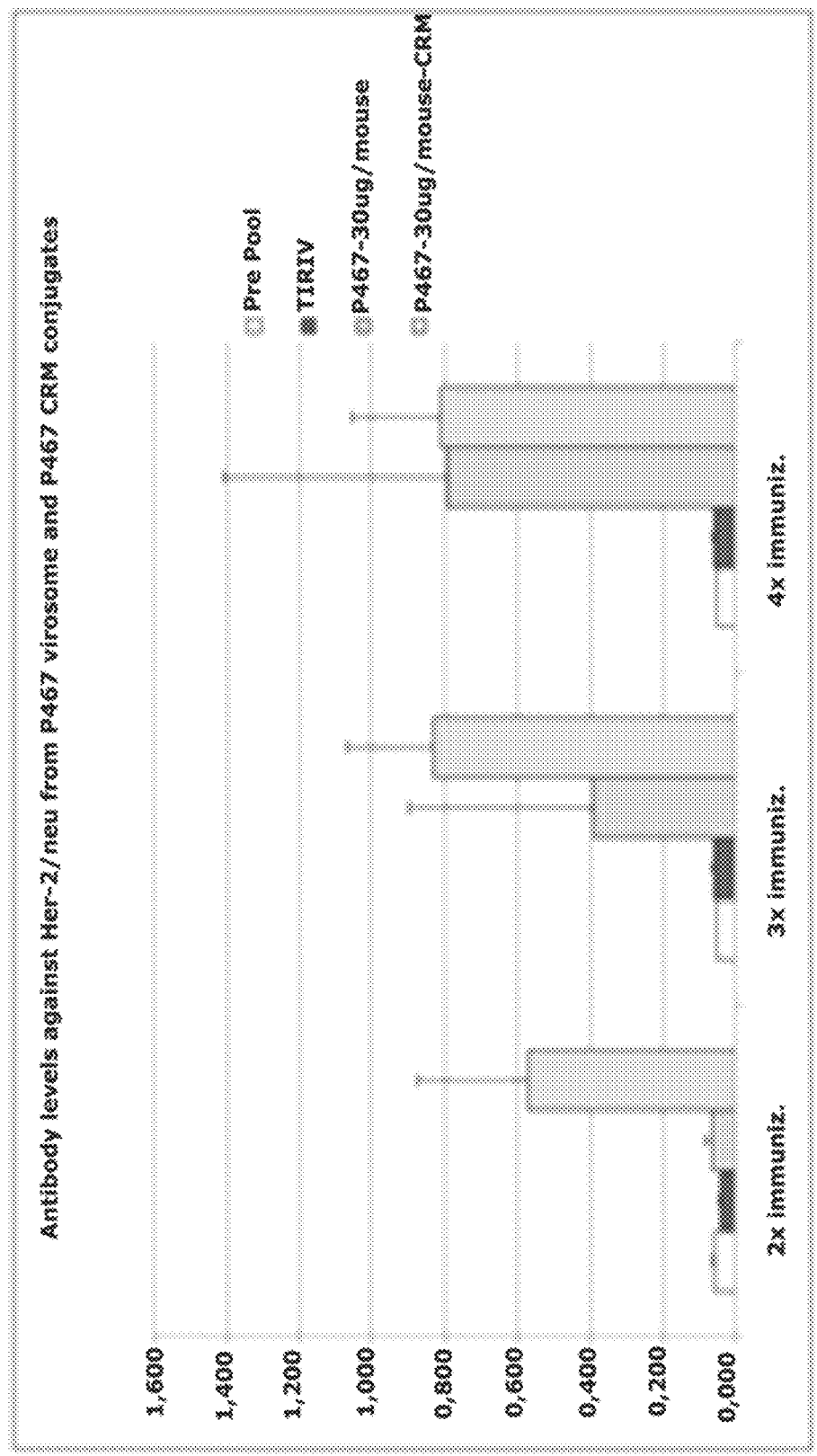
FIG. 12 shows a direct comparison of antibody titres after the $2^{nd}$ $3^{rd}$ and $4^{th}$ immunisation with the P467 fusion peptide conjugated to virosomes or to CRM197 at a concentration of 30 µg. From left to right in each group: Pre Pool (blood drawn prior to immunisation); TIRIV (empty virosome); P467-30 mg/mouse (virosome conjugated); P467-30 mg/mouse-CRM (CRM197 conjugated). All sera were assayed at the same dilution. Data are presented as OD values.

As shown in FIG. 12, a comparison of the kinetics of antibody responses against recombinant Her-2/neu after the $2^{nd}$, $3^{rd}$ and $4^{th}$ immunisation with 30 µg of the P467-virosome conjugate or 30 µg of the P467-CRM conjugate reveals that, even after the $2^{nd}$ immunisation, the anti-Her-2/neu antibody titre following immunisation with the CRM conjugate (fourth column in each cluster) was significantly higher than the antibody titre after immunisation with the corresponding virosome conjugate (third column in each cluster). After the $4^{th}$ immunisation, both conjugates lead to comparable recombinant anti-Her-2/neu antibody titres.

Figure 13:
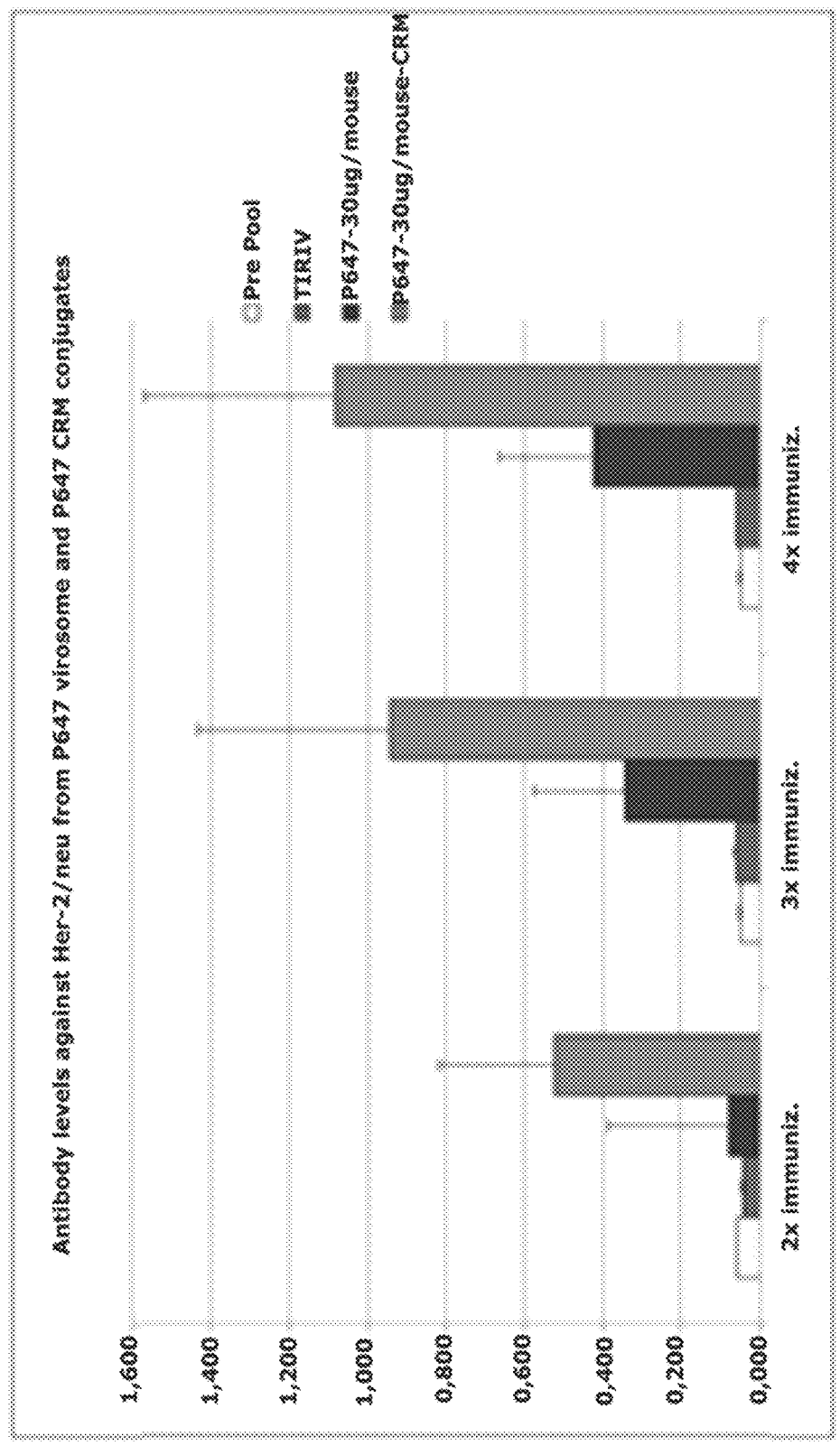
FIG. 13 shows a direct comparison of antibody titres after the $2^{nd}$, $3^{rd}$ and $4^{th}$ immunisation with the P647 fusion peptide conjugated to virosomes or to CRM197 at a concentration of 30 µg. From left to right in each group: Pre Pool (blood drawn prior to immunisation); TIRIV (empty virosome); P647-30 mg/mouse (virosome conjugated); P647-30 mg/mouse-CRM (CRM197 conjugated). All sera were assayed at the same dilution. Data are presented as OD values.

As shown in FIG. 13, a comparison of the kinetics of antibody responses against recombinant Her-2/neu after the $2^{nd}$, $3^{rd}$ and $4^{th}$ immunisation with 30 µg of the P647-virosome conjugate or 30 µg of the P647-CRM conjugate reveals that, even after the $2^{nd}$ immunisation, the anti-Her-2/neu antibody titre following immunisation with the CRM conjugate (fourth column in each cluster) was significantly higher than the antibody titre after immunisation with the corresponding virosome conjugate (third column in each cluster).

These results demonstrate the striking difference in the kinetics of Her-2/neu-specific antibody titres using either virosomes or CRM197 as the delivery system for the fusion peptides. The increase in antibody titres observed with virosome conjugates was significantly slower than with the CRM conjugates and typically needed four immunisations (in relation to fusion peptide P467) to reach similar levels as seen with corresponding CRM immunisations. In relation to fusion peptide P647, the virosome conjugates were inferior to the CRM conjugates, as they did not induce comparable antibody titres even after the $4^{th}$ immunisation (FIG. 13).

Example 10—Specificity to Native her-2/Neu Protein

Sera derived from the final blood sample drawn after four immunisations were analysed. The data are presented as OD values and all sera were diluted 1:100.

Figure 14:
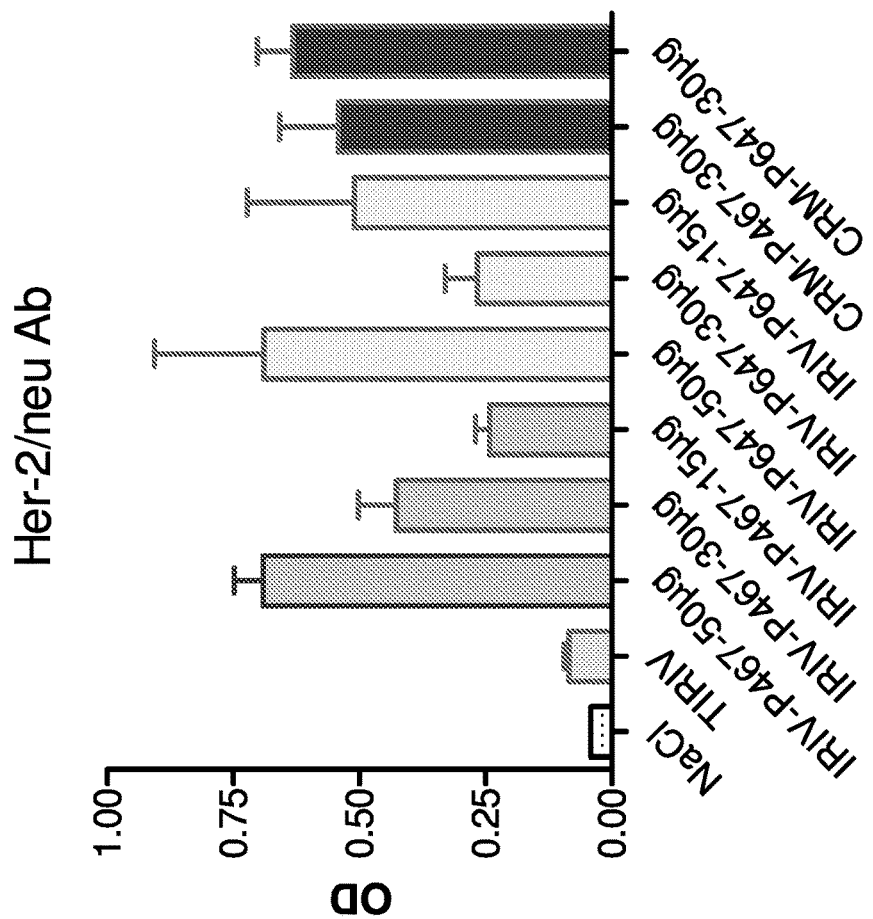
FIG. 14 shows immunisation with either virosomes incorporating the P467 or P647 fusion peptides or CRM197-fusion protein conjugates (CRM) induced antibodies that are capable of binding to native Her2/neu expressed on the surface of SKBR-3 breast cancer cells. Data are presented as OD values.

As shown in FIG. 14, the generated antibodies recognised the native form of Her-2/neu that is overexpressed in SKBR-3 breast cancer cells. The low sera dilutions were necessary to work within the range of the ELISA with non-purified cell lysate and were in line with the inventors' previous data. Despite significantly lower antibody titres against peptides and the recombinant extracellular Her-2/neu protein in groups immunized with virosome conjugates, the OD values were comparable between virosome- and CRM197-fusion peptide conjugates. These results might be explained by reactivity of antibodies raised against lipid linkage or some parts of virosomes with components in SKBR-3 cell lysates (e.g. cell membranes). This linkage is not present in the CRM197-fusion peptide conjugates.

Example 11—Evaluation of Immune Responses after Immunization with Peptide P467-CRM with Alum/Al(OH)$_3$ or Montanide Preparation of Reagents The fusion protein P467 (49 amino acids in length; synthetized at Bachem, Switzerland) was coupled to CRM197 (diphtheria toxin mutant; PiChem/Graz/Austria) and delivered at a stock concentration of 0.4 mg/ml. A P467-CRM-mediated immune response was evaluated in mice in the presence or absence of three adjuvants:
1) ALHYDROGEL®"85" (Aluminium hydroxide from Brenntag, Denmark; Aluminium content 10 mg/ml, Batch no. 85563; used at the dilution of 1/10 in accordance with manufacturer's instructions);
2) Alu-Gel-S-Suspension (Aluminium hydroxide from Serva, Germany; 1.3% purity, sterile, Aluminium content 5.9-7.1 mg/ml, catalogue no. 12261, Batch no. 111589; used at the dilution of 1/3 in accordance with manufacturer's instructions); and
3) Montanide ISA 51VG (from Seppic, France, Catalogue no. 36362ZFL2R3; Batch no. 2423395).

The immunization protocol is described in 'Immunization Protocol', below. Briefly, three concentrations of peptide construct were tested: 10 µg, 25 µg and 50 µg per injection. Aluminium hydroxide from Serva, which had been used in the animal studies outlined in the Examples above, was tested in two groups of mice (see 'Immunization Protocol') and compared with the use of Aluminium hydroxide from Brenntag. The amount of P467-CRM used with Aluminium hydroxide from Serva in these two groups were 10 µg and 25 µg.

Emulsification of Peptide Construct with Montanide

Emulsification of P467-CRM, PBS or NaCl with Montanide was undertaken in accordance with the manufacturer's instructions (Seppic, France). The P467-CRM peptide construct was mixed either with PBS (for Aluminium hydroxide, Brenntag) or NaCl (for Aluminium hydroxide, Serva). The adjuvants were then added to the solution and vortexed thoroughly at room temperature. The mixtures were then kept at room temperature for a minimum of 45 minutes prior to administration.

Immunization Protocol

Female Balb/C mice (Charles River Germany, 6-8 weeks at delivery) were immunized subcutaneously at 3 week intervals (n=8 mice per group; control groups n=4).

Groups of mice, i.e., A to O, were immunized as follows:

Group A (P467-CRM, 10 µg/Injection): 250 µl of P467-CRM together with 1250 µl NaCl (1500 µl). 150 µl/mouse (=10 µg/mouse)

Group B (P467-CRM, 25 µg/Injection): 625 µl of P467-CRM together with 875 µl NaCl (1500 µl). 150 µl/mouse (=25 µg/mouse)

Group C (P467-CRM, 50 µg/Injection): 1250 µl of P467-CRM together with 250 µl NaCl (1500 µl). 150 µl/mouse (=50 µg/mouse)

Group D (P467-CRM-Alum Brenntag, 10 µg/Injection): 250 µl of P467-CRM together with 175 µl Alum Brenntag+1325 µl PBS (17501). 175 µl/mouse (=10 µg/mouse)

Group E (P467-CRM-Alum Brenntag, 25 µg/Injection): 625 µl of P467-CRM together with 175 µl Alum Brenntag+950 µl PBS (1750 µl). 175 µl/mouse (=25 µg/mouse)

Group F (P467-CRM-Alum Brenntag, 50 µg/Injection): 1250 µl of P467-CRM together with 175 µl Alum Brenntag+325 µl PBS (17501). 175 µl/mouse (=50 µg/mouse)

Group G (P467-CRM-Alum Serva, 10 µg/Injection): 250 µl of P467-CRM together with 1000 µl Alum Serva+250 µl NaCl (1500 µl). 150 µl/mouse (=10 µg/mouse)

Group H (P467-CRM-Alum Serva, 25 µg/Injection): 625 µl of P467-CRM together with 1000 µl Alum Serva (1625 µl). 160 µl/mouse (=10 µg/mouse)

Group I (P467-CRM-Montanide, 10 µg/Injection): 300 µl of P467-CRM together with 300 µl NaCl+600 µl Montanide. 100 µl/mouse Group J (P467-CRM-Montanide, 25 µg/Injection): 700 µl of P467-CRM together with 700 µl Montanide. 126 µl/mouse Group K (P467-CRM-Montanide, 50 µg/Injection): 1300 µl of P467-CRM together with 1300 µl Montanide. 252 µl/mouse Group L (P467-Monomer, 25 µg/injection): 250 µl of of P467-CRM together with 1250 µl NaCl. 150 µl/mouse (=25 µg/mouse)

Group M (Montanide): 1000 µl NaCl+1000 µl Montanide. 252 µl/mouse

Group N (Alum Brenntag): 1575 µl PBS+175 µl Alum Brenntag. 175 µl/mouse

Group O (CRM, 50 µg/injection): Stock concentration: 2 mg/ml. Diluted 1:4 in NaCl (150+450 NaCl). 100 µl/mouse Control groups received either CRM, Aluminium hydroxide (Brenntag) or Montanide alone.

Blood was collected from the animals prior the first dose (BA0), 20 days after the $2_{nd}$ immunization (BA1) and 18 days after the $3^{rd}$ immunization (BA2). For the evaluation of antibody titre kinetics, blood was also taken at 8 weeks after the 3rd immunization (BA3).

In the remaining 4 mice from each group (except the control groups M, N, and O where all the mice were sacrificed), antibody titres were further evaluation at 8 and 16 weeks after the 3rd immunization (BA4 and BA5, respectively) to ascertain the antibody kinetics and necessary booster intervals.

Spleen Cell Preparation and Culture

The mice (n=4/group) were sacrificed and their spleens were removed under aseptic conditions, minced and filtered through sterile filters. Cell suspensions were prepared as previously described (Wiedermann et al, *Int. Immunol.* 1999; October; 11(10):1717-24). Splenocytes were plated at the concentration of $0.5 \times 10^6$ per well in 96-well round-bottomed plates and stimulated with CRM or P467 at a concentration of 20 g/ml for 72 hours. Supernatants were stored at −20° C. until analysis. Stimulation with ConA was carried out as a control.

ELISA Protocols (i) Measurement of Peptide-Specific Antibody Levels

Unconjugated fusion peptide P467 (Bachem, Switzerland), diluted in carbonate buffer, was used as coating antigen at a concentration of 0.5 µg/microtitre well. Sera (n=8/group) were diluted, added to the wells and the bound IgG antibodies were detected with horse radish peroxidase (HRP)-labelled rabbit anti-mouse IgG POX (Fc fragment specific, catalogue. no. 315-035-008; Jackson Immuno Research) followed by the addition of 3,3',5,5'-Tetramethylbenzidine (TMB). A stop solution was added and the plates were read at 450 vs 630 nm.

For detection of IgG subsets IgG1 and IgG2a, the diluted sera were applied to the antigen-coated wells of a microtitre plate, followed by either rat anti-mouse IgG1 or rat anti-mouse IgG2a antibodies. A secondary antibody HRP-labelled mouse anti-rat IgG was then used for detection followed by TMB. A stop solution was added and the plates were read at 450 vs 630 nm.

(ii) Measurement of her-2/Neu-Specific Antibody Levels

The wells of a microtitre plate were coated with a fusion protein comprising the recombinant extracellular domain of human Her-2/neu (amino acid residues 23-652) conjugated to the Fc region of human IgG1. Each well was coated with 0.1 μg of the fusion protein. Diluted mice sera were then analyzed, as described above.

For the detection of IgG subsets IgG1 and IgG2a, the diluted sera were applied to the antigen-coated well, followed by the addition of either rat anti-mouse IgG1, or rat anti-mouse IgG2a. A secondary HRP-labelled mouse anti-rat IgG (H+L) antibody was used of detection.

(iii) Measurement of In Vitro Cytokine Production—IL-2, IL-5 and IFNγ

Supernatants from CRM- or P467-stimulated splenocytes were collected and analyzed for the concentration of IL-2, IL-5 and IFNγ by ELISA in accordance with the manufacturer's instructions (Affymetrix eBioscience, USA). The supernatants were used undiluted or diluted 1:10-1:20 prior to analysis.

Fluorescence-Activated Cell Sorting (FACS) Analyses

FACS was performed on freshly isolated spleen cells ($2.5 \times 10^6$ cells/ml in 24 well flat-bottom plates). The cells were incubated for 2 hours in the presence of phorbol myristate acetate (PMA; 10 ng/ml) and lonomycin (1.25 μM) and for an additional 4 hours at 37° C. in presence of Brefeldin A (10 μg/ml). Cells were then kept at 4° C. overnight and stained the next morning with anti-mouse antibodies to the following targets:

| Antibody | Color |
| --- | --- |
| CD3 | Fitc |
| CD4 | Percp |
| CD8a$_{(Ly-2)}$ | PE |
| IFNγMaB | APC |
| Granzyme B | Pe Cy7 |
| CD335 (NKp46) | eFluor450 |
| CD19 | APCeFluor780 |

(i) Staining protocol:

Cells were harvested and split into micronic tubes ($1 \times 10^6$/ cells per tube). Single staining was performed for each mouse sample with the aforementioned antibody cocktail.

Cells were then washed, blocked with Fc block (anti-mouse CD16/32) and stained with antibodies to CD3, CD4, CD8, CD19 and CD335, followed by fixation/permeabilisation and intracellular staining for IFNγ and Granzyme B.

Analyses were performed for the characterization of splenocyte populations—T cells (CD3+CD4+ and CD3+CD8+), B cells (CD3-CD19+) and NK cells (CD3-CD335+). The analyses also included detection of intracellular IFNγ protein.

Statistical Analyses

Unpaired t-test (Two tailed, Confidence Intervals of 95%) was applied on Prism for analysis of the ELISA results. Significant differences are indicated by one or more asterisks (* P value <0.05,  0.01<P value<0.001, * P value <0.001). No significance is indicated as 'ns'. One way analysis of variance (ANOVA) was applied on Prism when more than two groups were compared. Mann Whitney test (Two tailed, Confidence Intervals of 95%) was applied on Prism for analysis of the FACS results.

Results

Humoral Responses (i) Peptide-Specific Antibody Levels

Figure 15A:
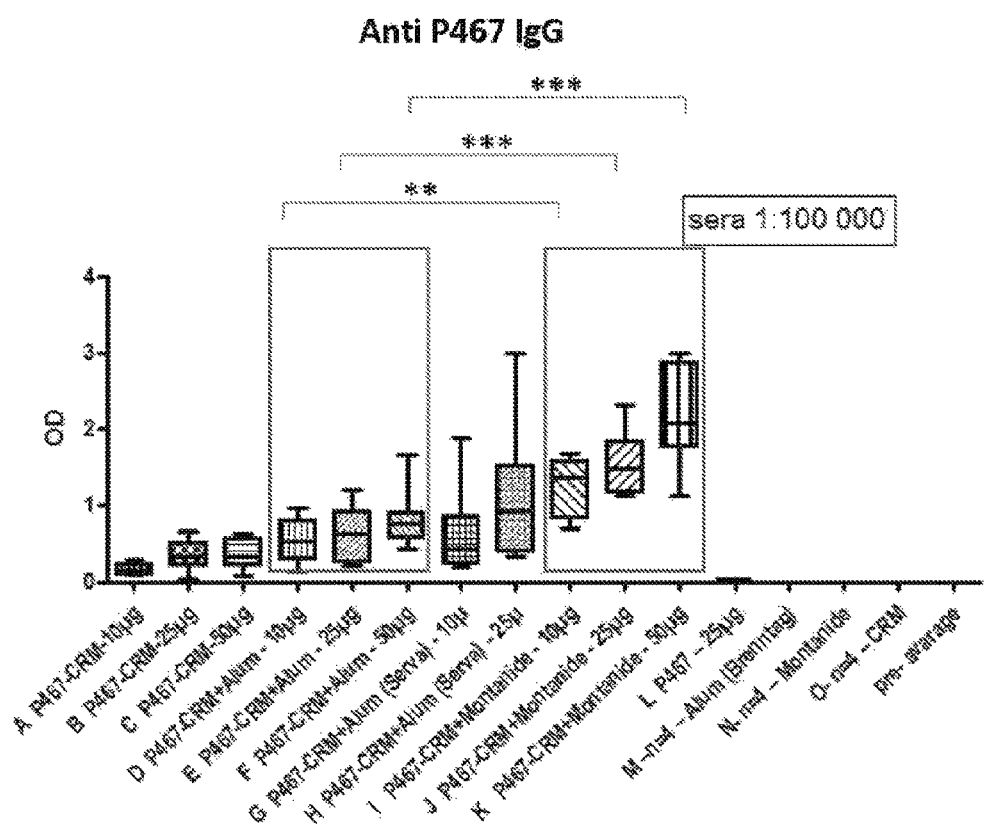
FIG. 15A shows the anti-P467 IgG antibody titre in mice following three doses of the P467-CRM197 fusion protein at 10 µg, 25 µg and 50 µg, administered alone (P467-CRM), with Alum from Brenntag (P467-CRM+Alum), with Alum from Serva (P467-CRM+Alum (Serva)) or with Montanide (P467-CRM+Montanide). Antibody titres were compared to levels seen in control animals administered with P467 peptide alone (P467; 25 µg), Alum from Brenntag (Alum (Brenntag)) or CRM197 alone (CRM). Data are presented as OD values; *p<0.05, p<0.01 and *p<0.001.
Figure 15B:
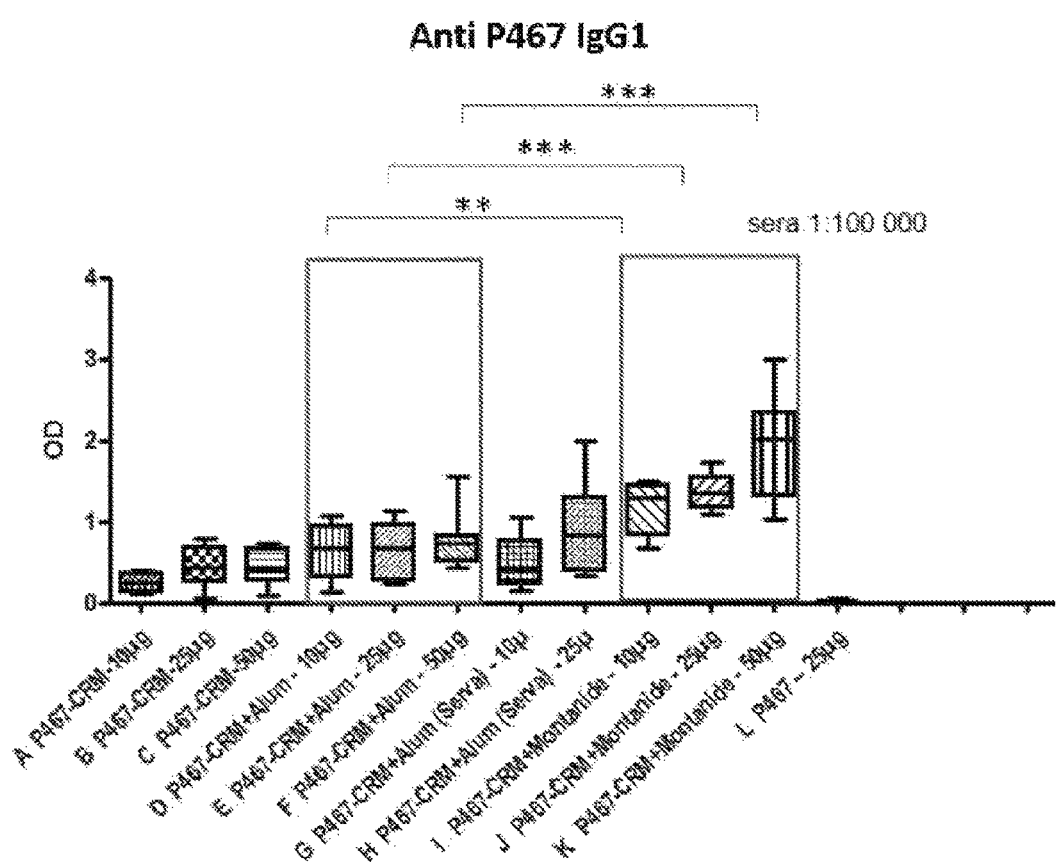
FIG. 15B shows the anti-P467 IgG1 antibody titre in mice following three doses of the P467-CRM197 fusion protein at 10 μg, 25 μg and 50 μg, administered alone (P467-CRM), with Alum from Brenntag (P467-CRM+Alum), with Alum from Serva (P467-CRM+Alum (Serva)) or with Montanide (P467-CRM+Montanide). Antibody titres were compared to levels seen in control animals administered with P467 peptide alone. Data are presented as OD values; *p<0.05, p<0.01 and *p<0.001.
Figure 15C:
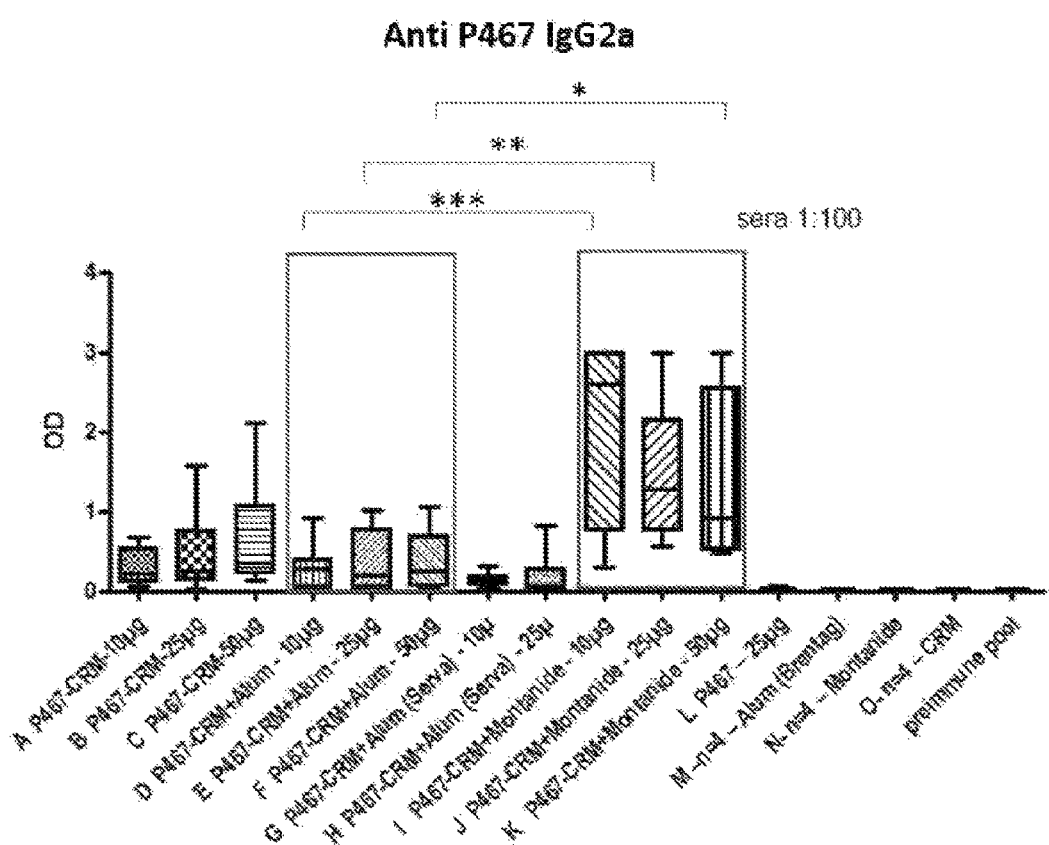
FIG. 15C shows the anti-P467 IgG2a antibody titre in mice following three doses of the P467-CRM197 fusion protein at 10 μg, 25 μg and 50 μg, administered alone (P467-CRM), with Alum from Brenntag (P467-CRM+Alum), with Alum from Serva (P467-CRM+Alum (Serva)) or with Montanide (P467-CRM+Montanide). Antibody titres were compared to levels seen in control animals administered with P467 peptide alone (P467; 25 μg), Alum from Brenntag (Alum (Brenntag)) or CRM197 alone (CRM). Data are presented as OD values; *p<0.05, p<0.01 and *p<0.001.

Sera derived from the final bleed after three immunizations, as well as pre-immunisation sera, were diluted 1:100.000 (for IgG and IgG) or 1:100 (for IgG2a). Antibody titres for total serum IgG, IgG1 and IgG2a are shown in FIGS. 15A-C, respectively.

In the figures, the following groups (framed) were compared with each other and statistically evaluated:
D, E, F: Alum: 10 μg, 25 μg, 50 μg
I, J, K: Montanide: 10 μg, 25 g, 50 μg The data show that anti-P467 antibodies were elicited in all mice immunized with P467-CRM. No antibody response was induced in the control animals or in mice immunized with P467 alone. Compared with Alum (Brenntag), antibody levels for IgG, IgG and IgG2a were significantly higher when P467-CRM was administered with Montanide. The IgG2a titres were generally lower than for IgG1, although considerably higher IgG2a titres were evident in animals immunized with P467-CRM+Montanide.

(ii) Her-2/Neu-Specific Antibody Levels

Figure 16A:
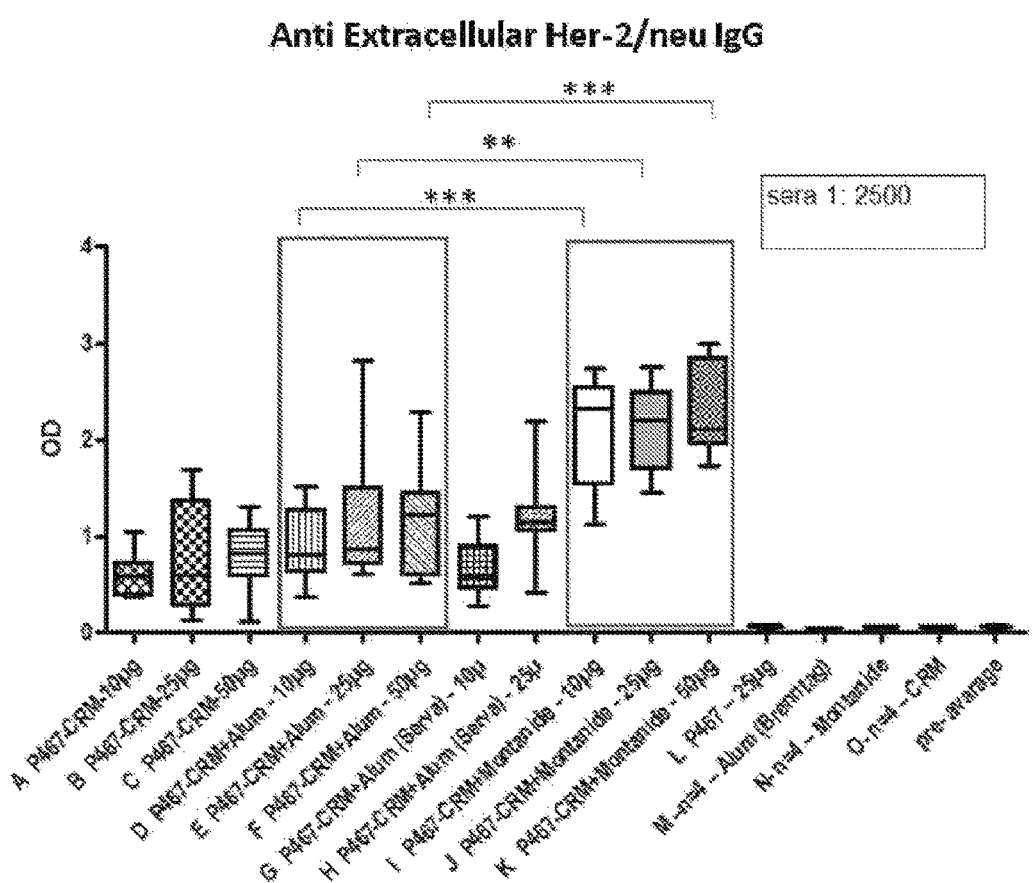
FIG. 16A shows the anti-extracellular Her2/neu IgG antibody titre in mice following three doses of the P467-CRM197 fusion protein at 10 μg, 25 μg and 50 μg, administered alone (P467-CRM), with Alum from Brenntag (P467-CRM+Alum), with Alum from Serva (P467-CRM+Alum (Serva)) or with Montanide (P467-CRM+Montanide). Antibody titres were compared to levels seen in control animals administered with P467 peptide alone (P467; 25 μg), Alum from Brenntag (Alum (Brenntag)) or CRM197 alone (CRM). Data are presented as OD values; *p<0.05, p<0.01 and *p<0.001.
Figure 16B:
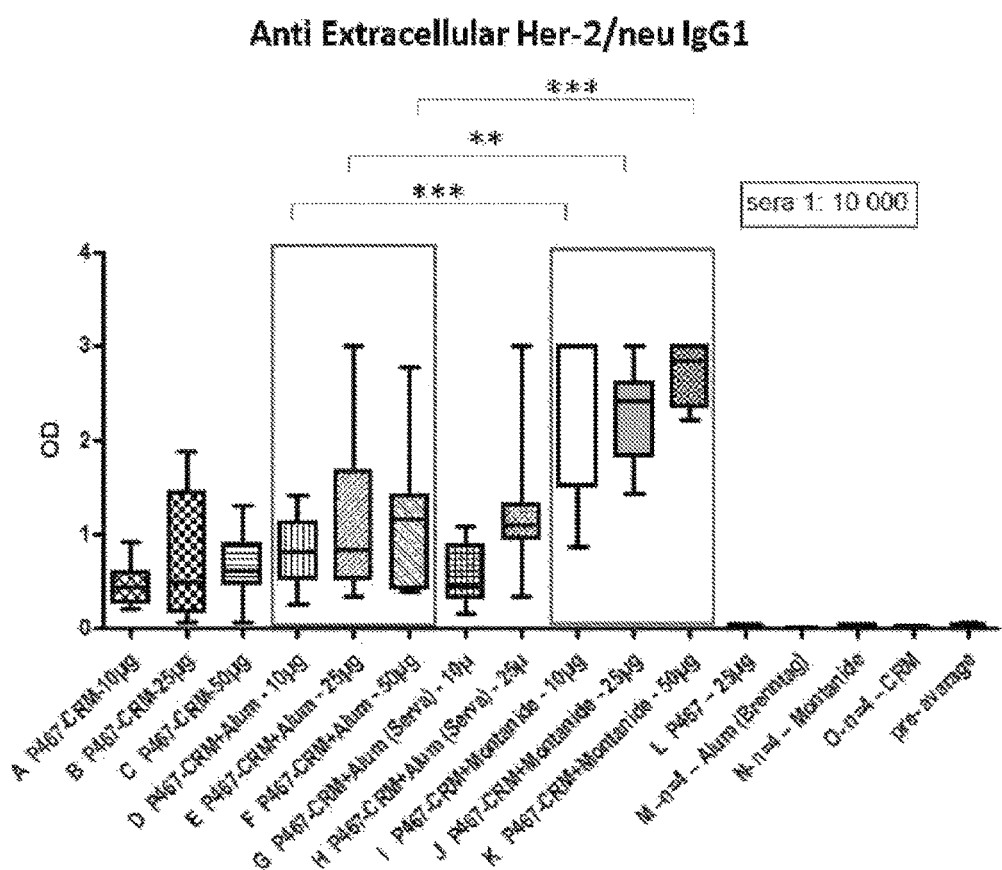
FIG. 16B shows the anti-extracellular Her2/neu IgG1 antibody titre in mice following three doses of the P467-CRM197 fusion protein at 10 μg, 25 μg and 50 μg, administered alone (P467-CRM), with Alum from Brenntag (P467-CRM+Alum), with Alum from Serva (P467-CRM+Alum (Serva)) or with Montanide (P467-CRM+Montanide). Antibody titres were compared to levels seen in control animals administered with P467 peptide alone (P467; 25 μg), Alum from Brenntag (Alum (Brenntag)) or CRM197 alone (CRM). Data are presented as OD values; *p<0.05, p<0.01 and *p<0.001.

Sera derived from the final bleed after three immunizations and pre-immunization sera were diluted 1:2500 (to 10.000) (IgG), 1:10.000 (IgG1) and 1:100 (IgG2a). Antibody titres for serum IgG, IgG and IgG2a are shown in FIGS. 16A-C, respectively.

High titres of anti-extracellular Her-2/neu IgG and IgG1 antibodies were evident in all animals immunized with P467-CRM. No anti-Her-2/neu antibody response was evident in the control groups or in mice immunized with P467 alone. Compared to Alum (Brenntag), the IgG and IgG antibody titres were significantly higher when the P467-CRM peptide construct was administered with Montanide.

In Vitro Production of Cytokines (IL-2, IFNγ, IL-5)

(i) IL-2 Production after Stimulation with CRM or P467

Figure 17A:
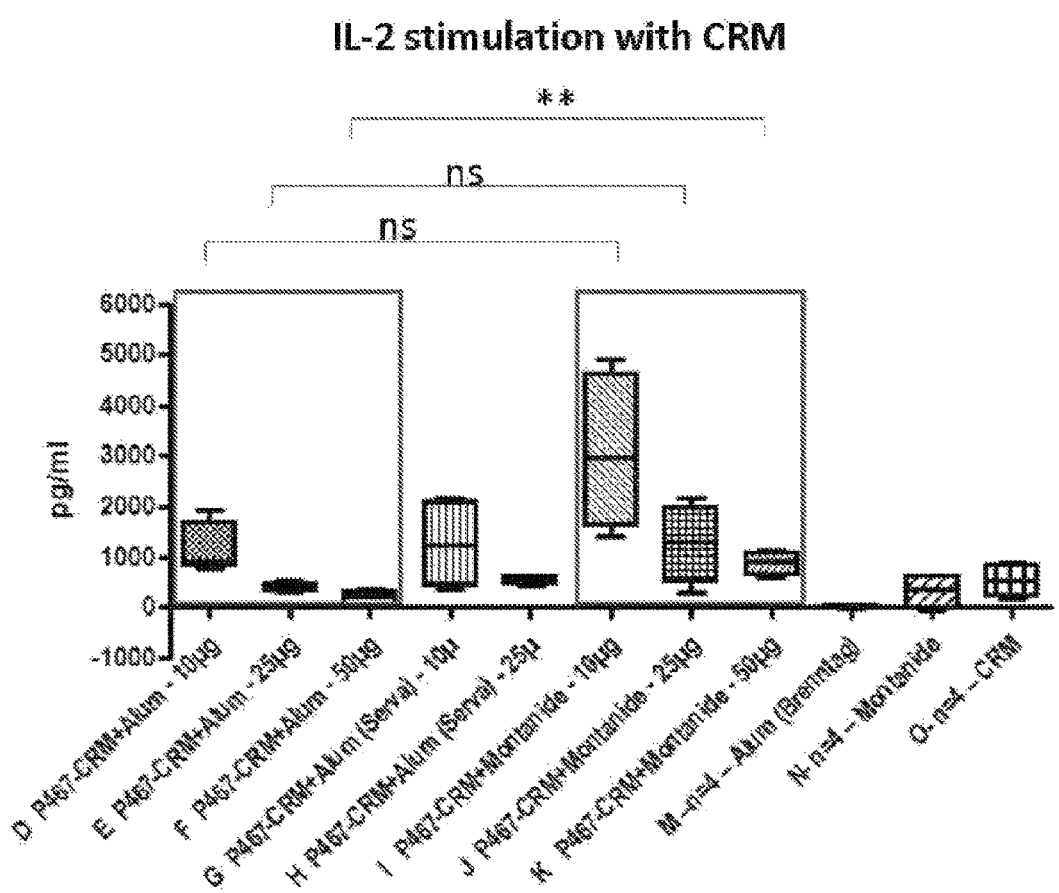
FIG. 17A shows IL-2 production by CRM197-activated splenocytes derived from mice immunized with P467-CRM197 fusion protein at 10 μg, 25 μg and 50 μg, administered alone (P467-CRM), with Alum from Brenntag (P467-CRM+Alum), with Alum from Serva (P467-CRM+Alum (Serva)) or with Montanide (P467-CRM+Montanide). IL-12 levels (pg/ml) were compared to IL-2 levels seen in CRM197-activated splenocytes derived from control animals administered with Alum alone (Alum (Brenntag)), Montanide alone (Montanide) or CRM197 alone (CRM). Data are presented as pg/ml; **p<0.01 and ns=not statistically significant.
Figure 17B:
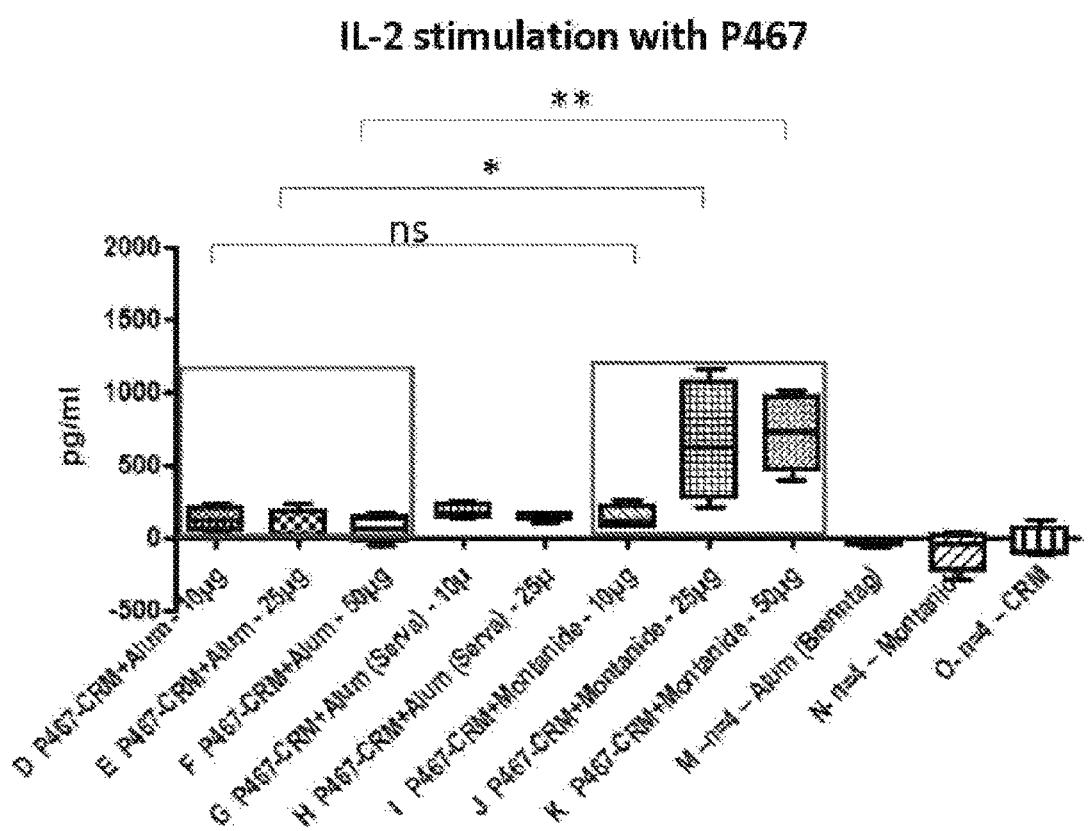
FIG. 17B shows IL-2 production by P467-activated splenocytes derived from mice immunized with P467-CRM197 fusion protein at 10 μg, 25 μg and 50 μg, administered alone (P467-CRM), with Alum from Brenntag (P467-CRM+Alum), with Alum from Serva (P467-CRM+Alum (Serva)) or with Montanide (P467-CRM+Montanide). IL-12 levels (pg/ml) were compared to IL-2 levels seen in P467-activated splenocytes derived from control animals administered with Alum alone (Alum (Brenntag)), Montanide alone (Montanide) or CRM197 alone (CRM). Data are presented as pg/ml; *p<0.05, **p<0.01 and ns=not statistically significant.

IL-2 levels were higher in CRM-stimulated splenocytes derived from mice immunized with P467-CRM in the presence of Montanide when compared to CRM-stimulated splenocytes derived from mice immunized with P467-CRM in the presence of Alum (see FIGS. 17A and 17B).

(ii) IFNγ Production after Stimulation with CRM or P467

Figure 18A:
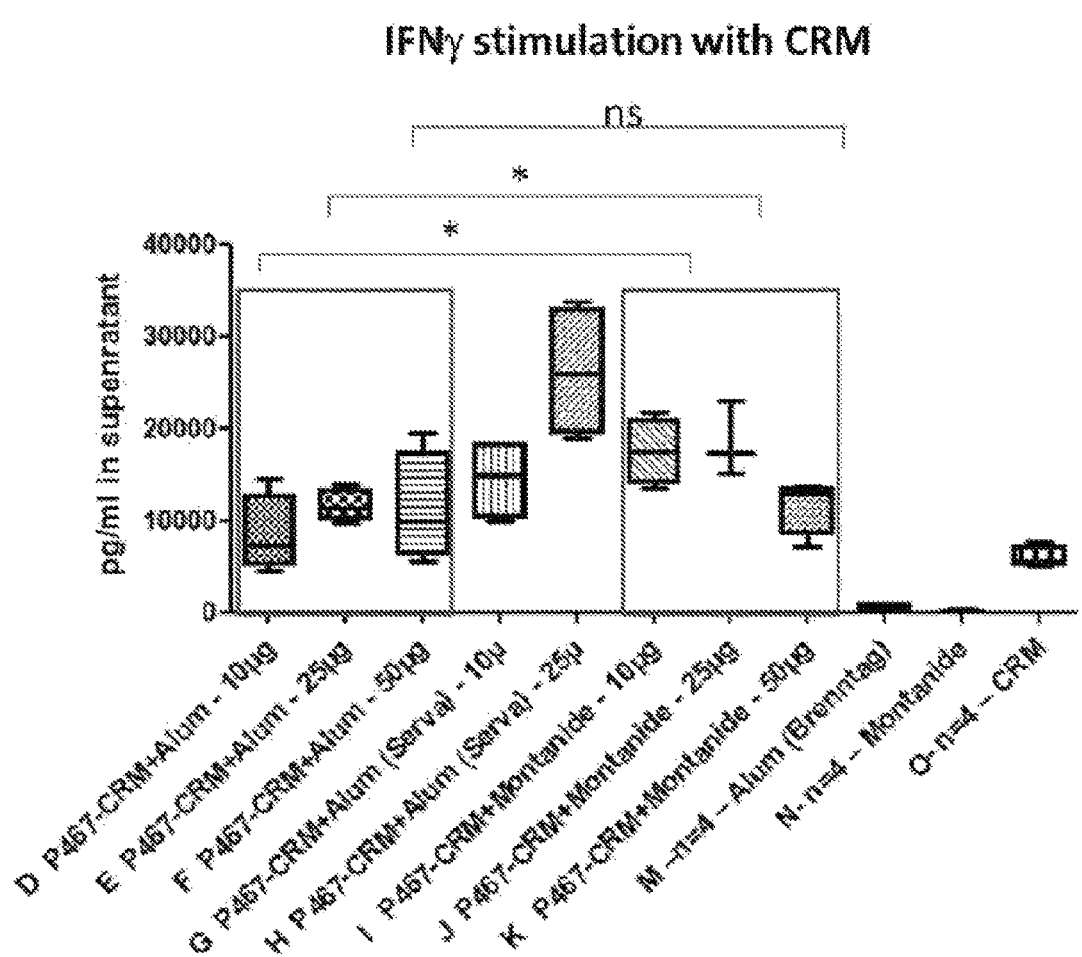
FIG. 18A shows IFNγ production by CRM197-activated splenocytes derived from mice immunized with P467-CRM197 fusion protein at 10 μg, 25 μg and 50 μg, administered alone (P467-CRM), with Alum from Brenntag (P467-CRM+Alum), with Alum from Serva (P467-CRM+Alum (Serva)) or with Montanide (P467-CRM+Montanide). IFNγ levels (pg/ml) were compared to IFNγ levels seen in CRM197-activated splenocytes derived from control animals administered with Alum alone (Alum (Brenntag)), Montanide alone (Montanide) or CRM197 alone (CRM). Data are presented as pg/ml; *p<0.05 and ns=not statistically significant.
Figure 18B:
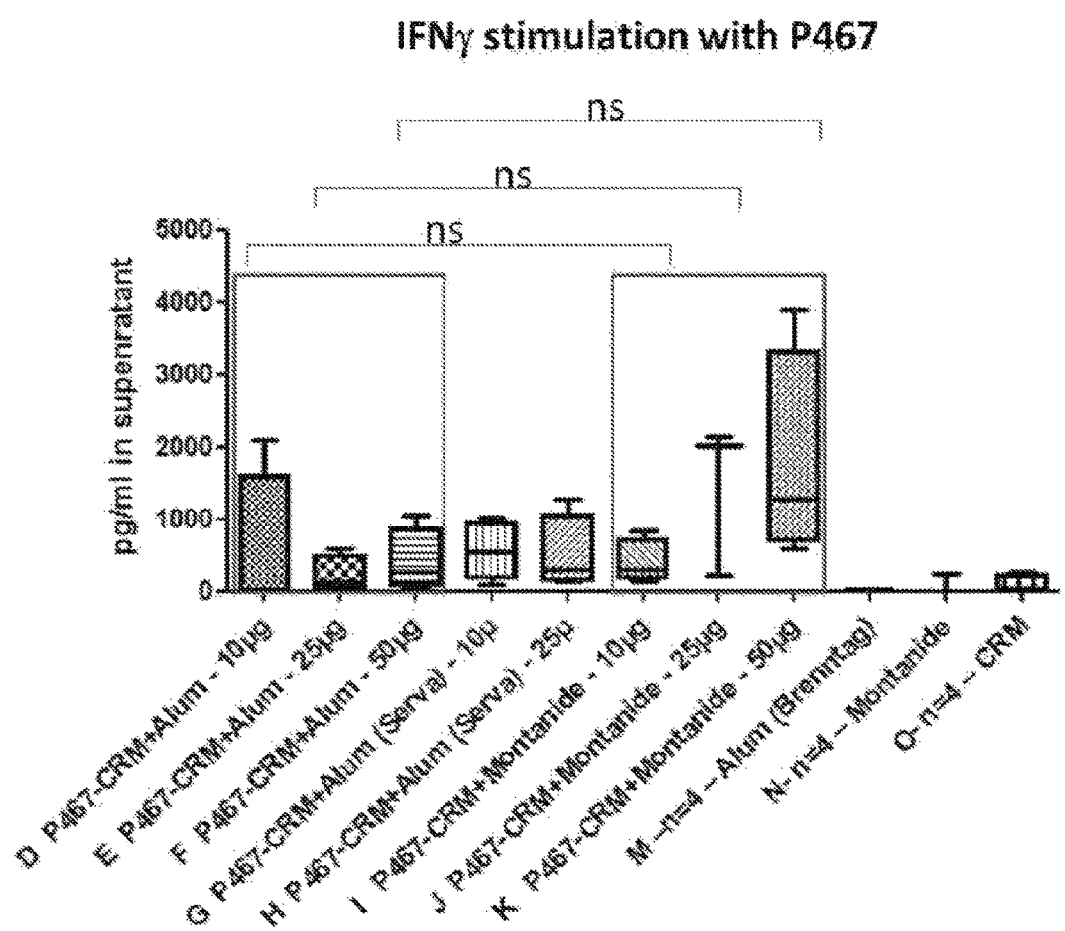
FIG. 18B shows IFNγ production by P467-activated splenocytes derived from mice immunized with P467-CRM197 fusion protein at 10 μg, 25 μg and 50 μg, administered alone (P467-CRM), with Alum from Brenntag (P467-CRM+Alum), with Alum from Serva (P467-CRM+Alum (Serva)) or with Montanide (P467-CRM+Montanide). IFNγ levels (pg/ml) were compared to IFNγ levels seen in P467-activated splenocytes derived from control animals administered with Alum alone (Alum (Brenntag)), Montanide alone (Montanide) or CRM197 alone (CRM). Data are presented as pg/ml; ns=not statistically significant.

FIGS. 18A and 18B show the concentration of IFNγ in the supernatant of splenocytes that have been cultured in vitro in the presence of CRM (FIG. 18A) or P467 (FIG. 18B). In mice immunized with 25 μg of P467-CRM with Montanide, the level of IFNγ was out of range. The data from this mouse was excluded and additional analysis was performed, as shown in FIG. 18C (stimulation by CRM) and FIG. 18D (stimulation by P467).

IFNγ production was induced by CRM stimulation in splenocytes derived from all mice immunized with P467-CRM in the presence of Alum or Montanide. With Montanide (in the 10 g group), IFNγ levels were higher than in the corresponding group immunized with P467-CRM in the presence of Alum (Brenntag). Upon stimulation with the P467-CRM, IFNγ levels were strongest in the Montanide group immunized with 50 g P467-CRM.

(iii) IL-5 Production after Stimulation with CRM or P467

Figure 19A:
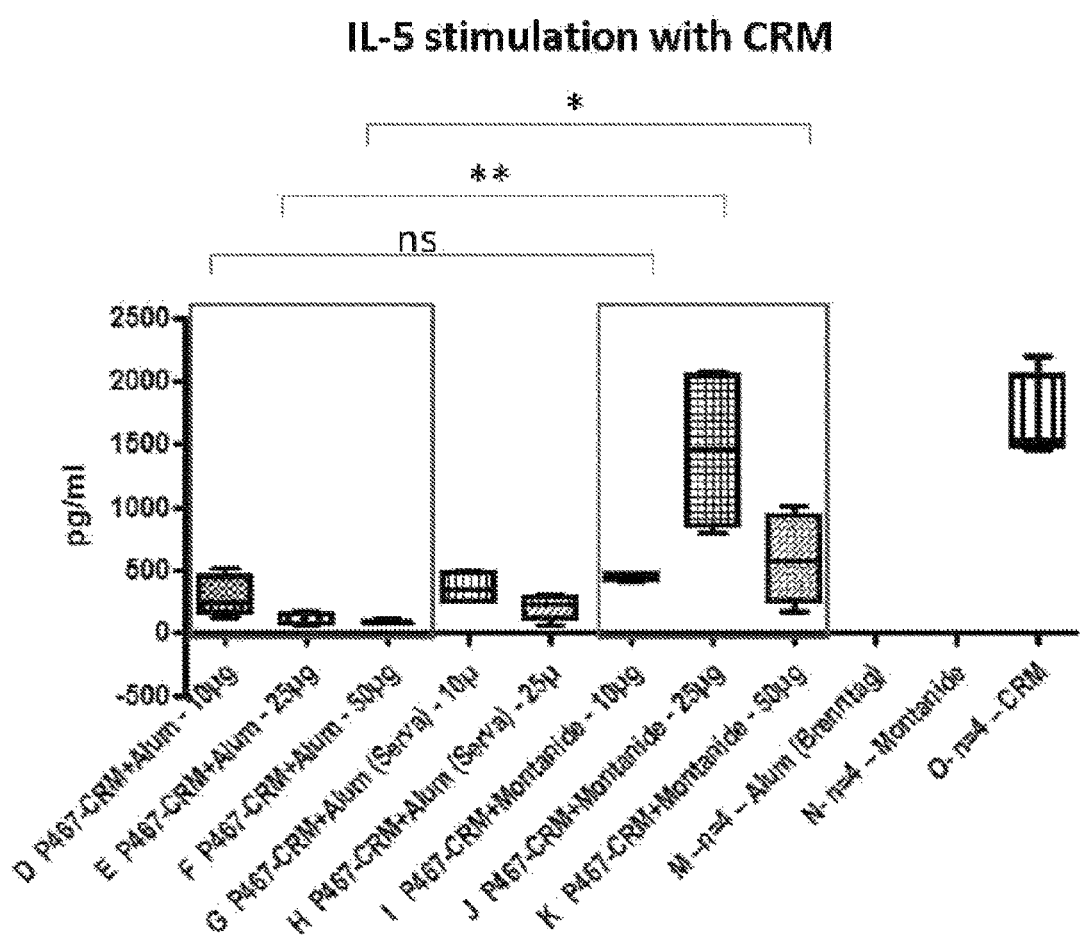
FIG. 19A shows IL-5 production by CRM197-activated splenocytes derived from mice immunized with P467-CRM197 fusion protein at 10 μg, 25 μg and 50 μg, administered alone (P467-CRM), with Alum from Brenntag (P467-CRM+Alum), with Alum from Serva (P467-CRM+Alum (Serva)) or with Montanide (P467-CRM+Montanide). IL-5 levels (pg/ml) were compared to IL-5 levels seen in CRM197-activated splenocytes derived from control animals administered with Alum alone (Alum (Brenntag)), Montanide alone (Montanide) or CRM197 alone (CRM). Data are presented as pg/ml; *p<0.05, **p<0.01 and ns=not statistically significant.
Figure 19B:
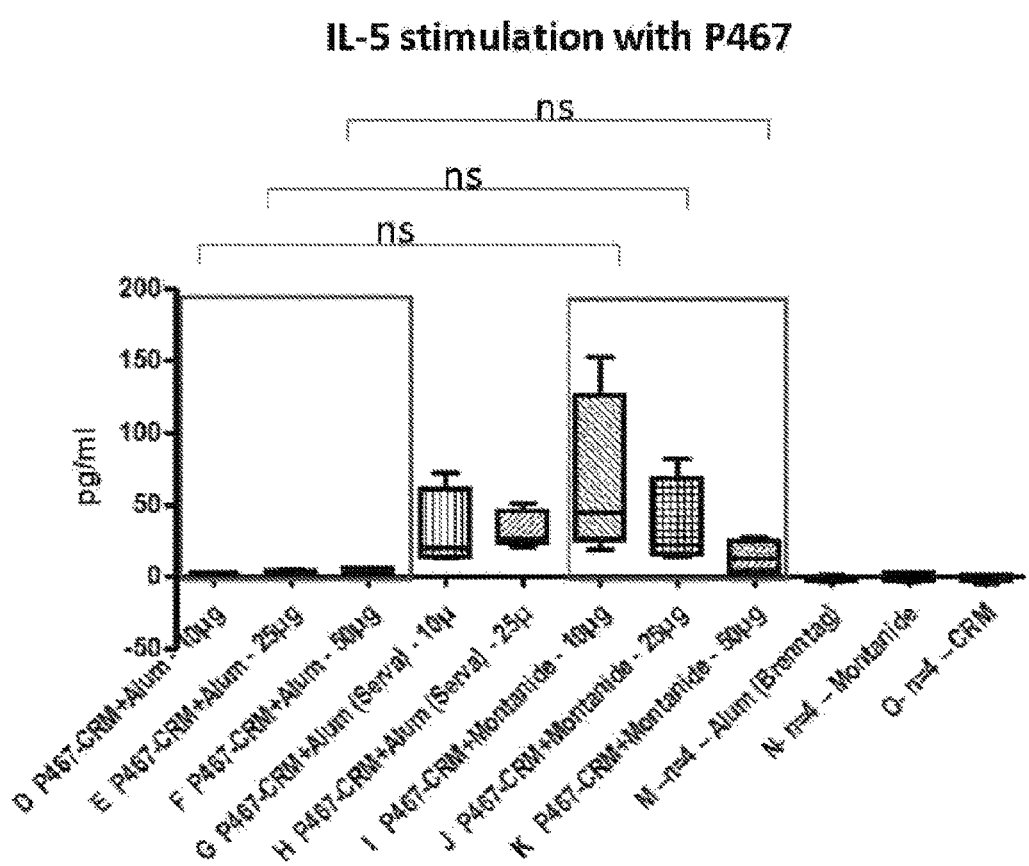
FIG. 19B shows IL-5 production by P467-activated splenocytes derived from mice immunized with P467-CRM197 fusion protein at 10 μg, 25 μg and 50 μg, administered alone (P467-CRM), with Alum from Brenntag (P467-CRM+Alum), with Alum from Serva (P467-CRM+Alum (Serva)) or with Montanide (P467-CRM+Montanide). IL-5 levels (pg/ml) were compared to IL-5 levels seen in P467-activated splenocytes derived from control animals administered with Alum alone (Alum (Brenntag)), Montanide alone (Montanide) or CRM197 alone (CRM). Data are presented as pg/ml; ns=not statistically significant.

FIGS. 19A and 19B show the concentration of IL-5 in the supernatant of splenocytes that have been cultured in vitro in the presence of CRM (FIG. 19A) or P467 (FIG. 19B).

IL-5 levels were significantly higher in CRM-stimulated splenocytes derived from mice immunized with P467-CRM in the presence of Montanide After stimulation with the P467-CRM peptide construct, some IL-5 production was induced in Montanide immunized mice, although the level IL-5 was about 10-fold lower when compared to levels after CRM stimulation.

Figure 20A:
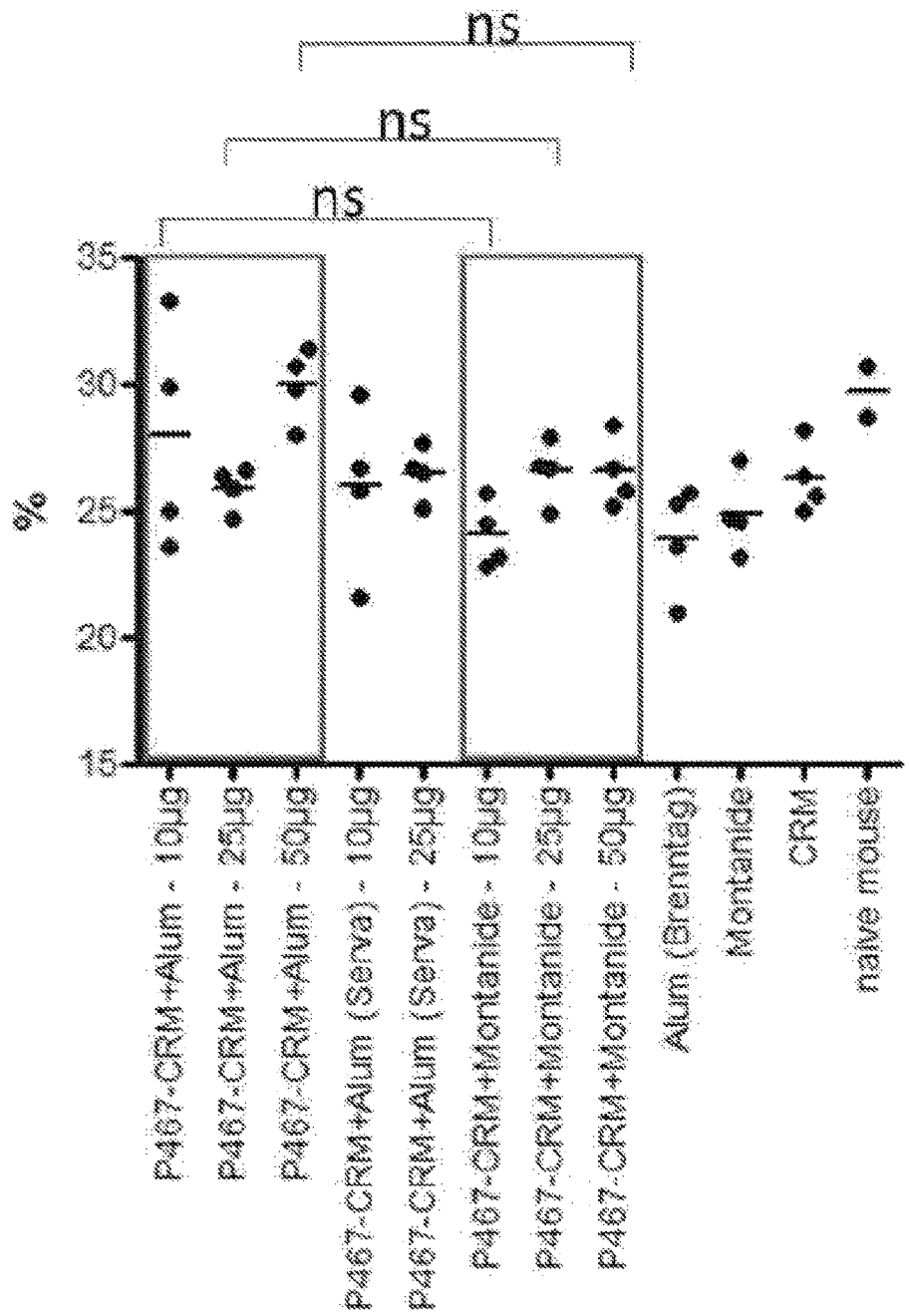
FIG. 20A shows the distribution of CD3+CD4+ splenocytes (T lymphocytes) at sacrifice in mice immunized with P467-CRM197 fusion protein at 10 μg, 25 μg and 50 μg, administered with Alum from Brenntag (P467-CRM+Alum), with Alum from Serva (P467-CRM+Alum (Serva)) or with Montanide (P467-CRM+Montanide). The percentage of CD3+CD4+ splenocytes was compared to the percentage of CD3+CD4+ splenocytes seen in control animals administered with Alum alone (Alum (Brenntag)), Montanide alone (Montanide) or CRM197 alone (CRM). Data are presented as a percentage of total cell number; ns=not statistically significant.
Figure 20B:
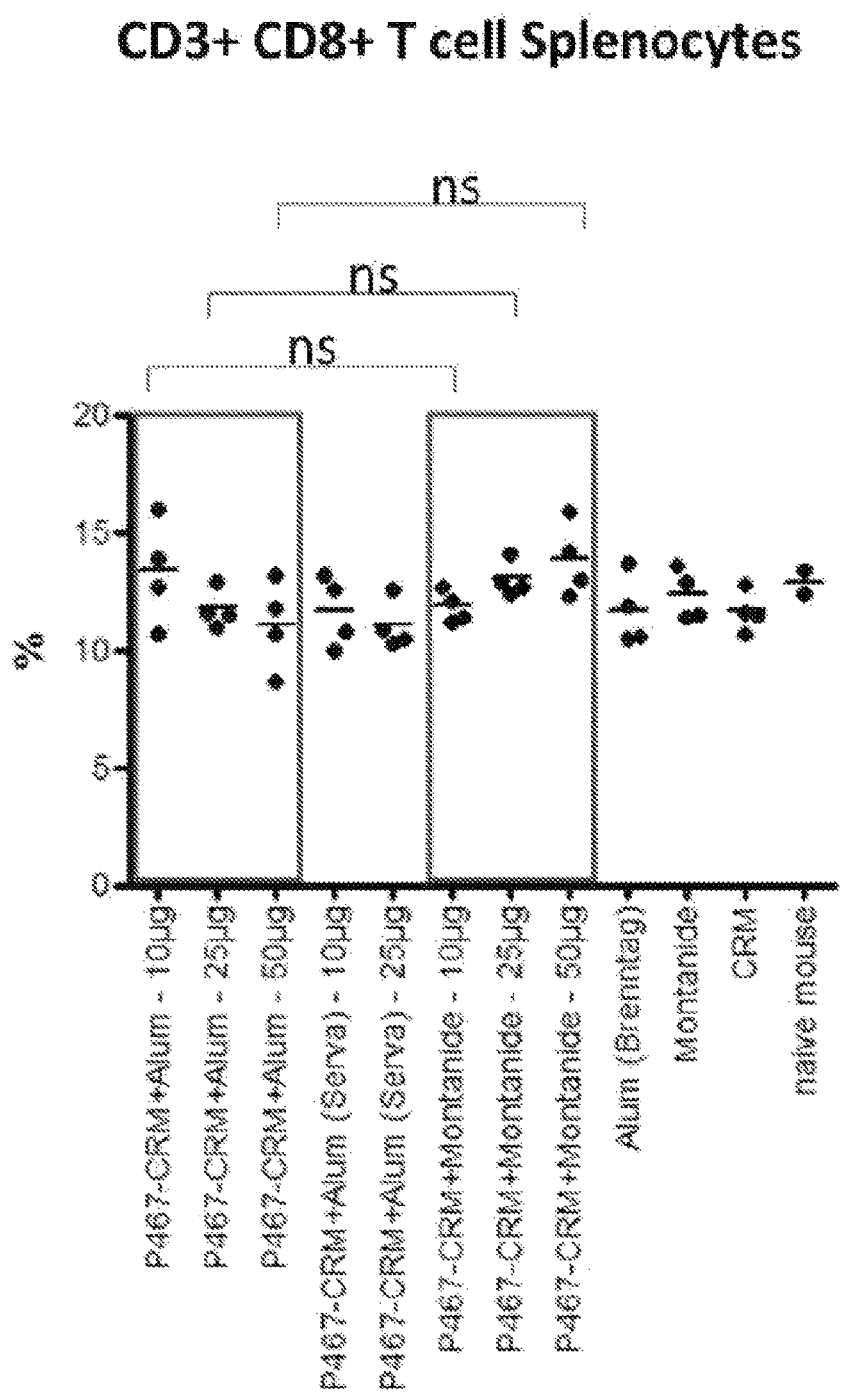
FIG. 20B shows the distribution of CD3+CD8+ splenocytes (T lymphocytes) at sacrifice in mice immunized with P467-CRM197 fusion protein at 10 μg, 25 μg and 50 μg, administered with Alum from Brenntag (P467-CRM+Alum), with Alum from Serva (P467-CRM+Alum (Serva)) or with Montanide (P467-CRM+Montanide). The percentage of CD3+CD8+ splenocytes was compared to the percentage of CD3+CD8+ splenocytes seen in control animals administered with Alum alone (Alum (Brenntag)), Montanide alone (Montanide) or CRM197 alone (CRM). Data are presented as a percentage of total cell number; ns=not statistically significant.
Figure 20C:
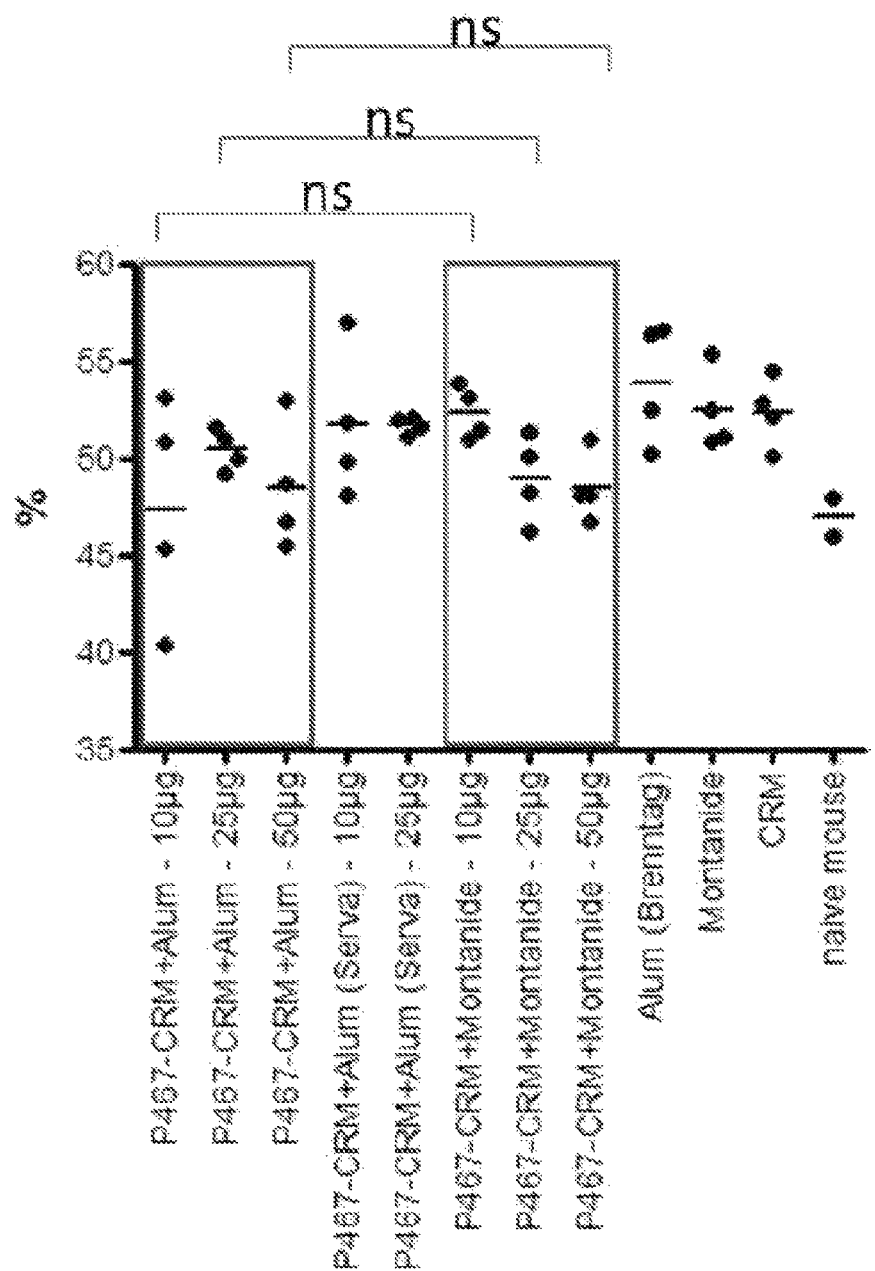
FIG. 20C shows the distribution of CD3-CD19+ splenocytes (B cells) at sacrifice in mice immunized with P467-CRM197 fusion protein at 10 μg, 25 μg and 50 μg, administered with Alum from Brenntag (P467-CRM+Alum), with Alum from Serva (P467-CRM+Alum (Serva)) or with Montanide (P467-CRM+Montanide). The percentage of CD3-CD19+ splenocytes was compared to the percentage of CD3-CD19+ splenocytes seen in control animals administered with Alum alone (Alum (Brenntag)), Montanide alone (Montanide) or CRM197 alone (CRM). Data are presented as a percentage of total cell number; ns=not statistically significant.
Figure 20D:
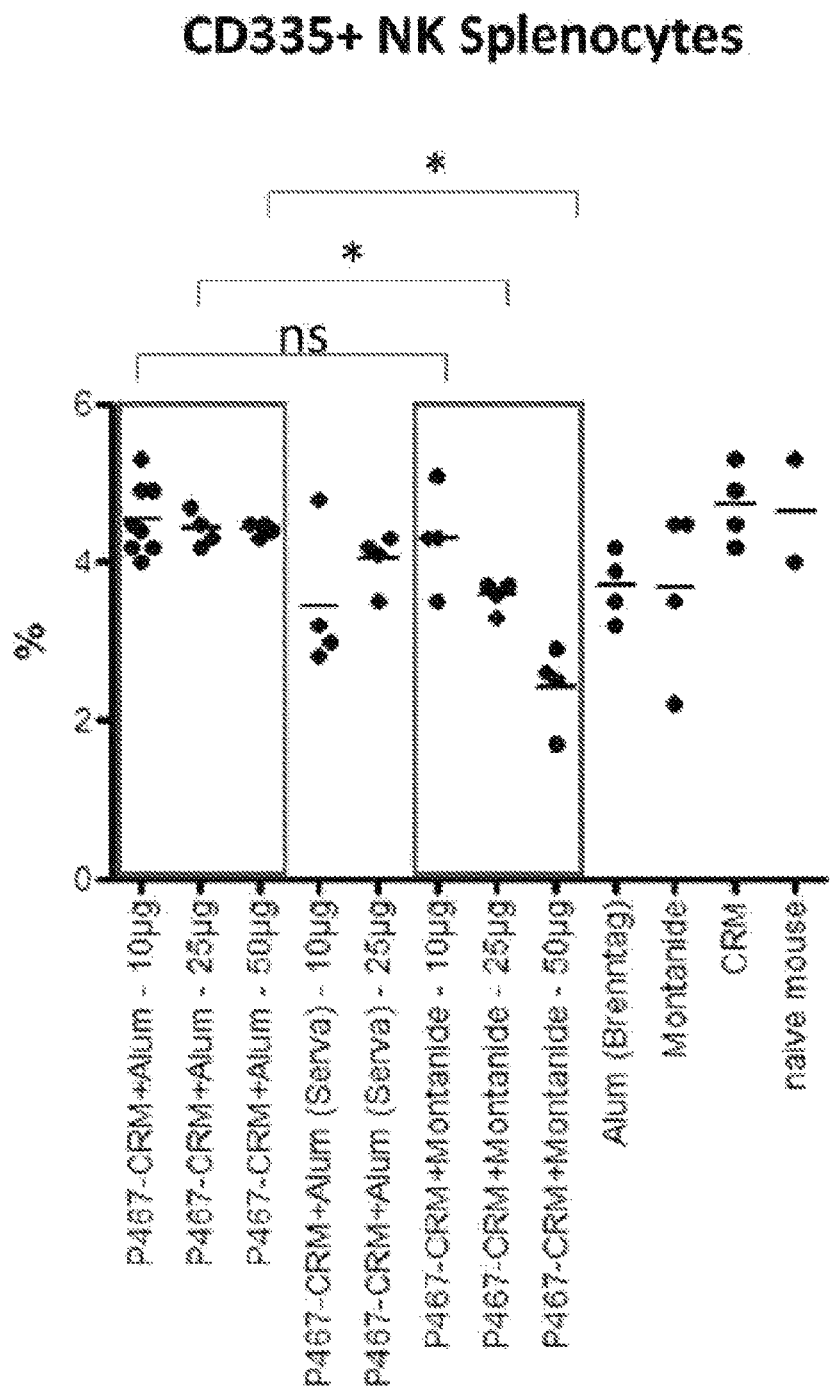
FIG. 20D shows the distribution of CD335+ splenocytes (natural killer (NK) cells) at sacrifice in mice immunized with P467-CRM197 fusion protein at 10 μg, 25 μg and 50 μg, administered with Alum from Brenntag (P467-CRM+Alum), with Alum from Serva (P467-CRM+Alum (Serva)) or with Montanide (P467-CRM+Montanide). The percentage of CD335+ splenocytes was compared to the percentage of CD335+ splenocytes seen in control animals administered with Alum alone (Alum (Brenntag)), Montanide alone (Montanide) or CRM197 alone (CRM). Data are presented as a percentage of total cell number; *p<0.05 and ns=not statistically significant.

Characterization of Splenocytes by FACS Analysis; Intracellular Staining of IFNγ Production In order to evaluate whether the use of different adjuvants (i.e., Alum versus Montanide) alter the lymphocyte distribution, particularly CD8+ and CD4+ lymphocytes, FACS analysis of splenocytes was carried out after immunization with different concentrations of P467 in the presence of Montanide or Alum. Splenocytes were isolated from the mice and analysed for percentages of T cells ($CD3^+CD4^+$, FIG. 20A, and $CD3^+CD8^+$, FIG. 20B), B cells ($CD3^-CD19^+$, FIG. 20C) and NK cells ($CD3^-CD335^+$, FIG. 20D).

The data show a significant reduction of NK cells in splenocytes derived from mice that were immunised with higher doses of P467-CRM (i.e. 25 mg and 50 mg) together with Montanide, when compared with Alum (Brenntag).

Detection of IFNγ-Producing Splenocytes by FACS Analysis

Figure 21A:
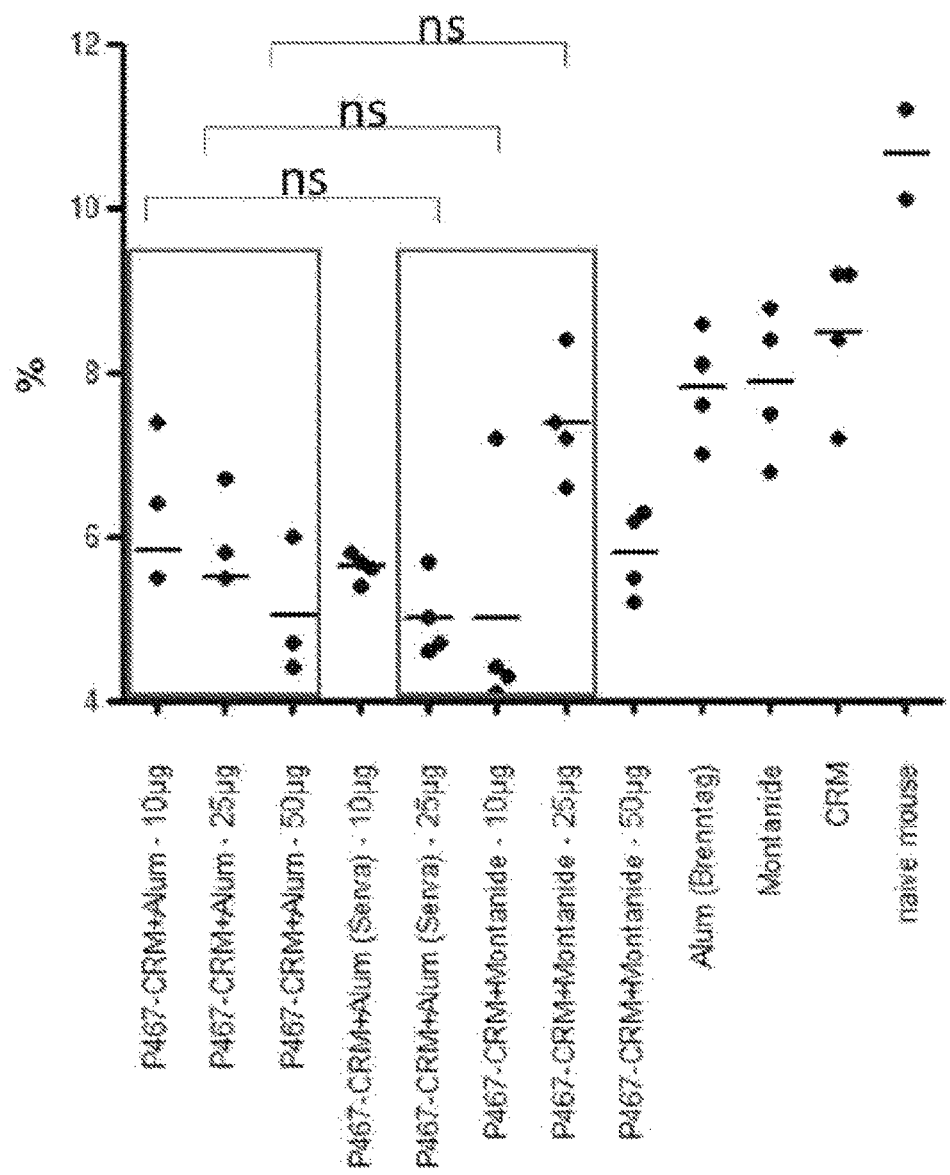
FIG. 21A shows the distribution of CD3+CD4+IFNγ+ splenocytes (IFNγ-producing T cells) at sacrifice in mice immunized with P467-CRM197 fusion protein at 10 μg, 25 μg and 50 μg, administered with Alum from Brenntag (P467-CRM+Alum), with Alum from Serva (P467-CRM+Alum (Serva)) or with Montanide (P467-CRM+Montanide). The percentage of CD3+CD4+IFNγ+ splenocytes was compared to the percentage of CD3+CD4+IFNγ+ splenocytes seen in control animals administered with Alum alone (Alum (Brenntag)), Montanide alone (Montanide) or CRM197 alone (CRM). Data are presented as a percentage of total cell number; ns=not statistically significant.
Figure 21B:
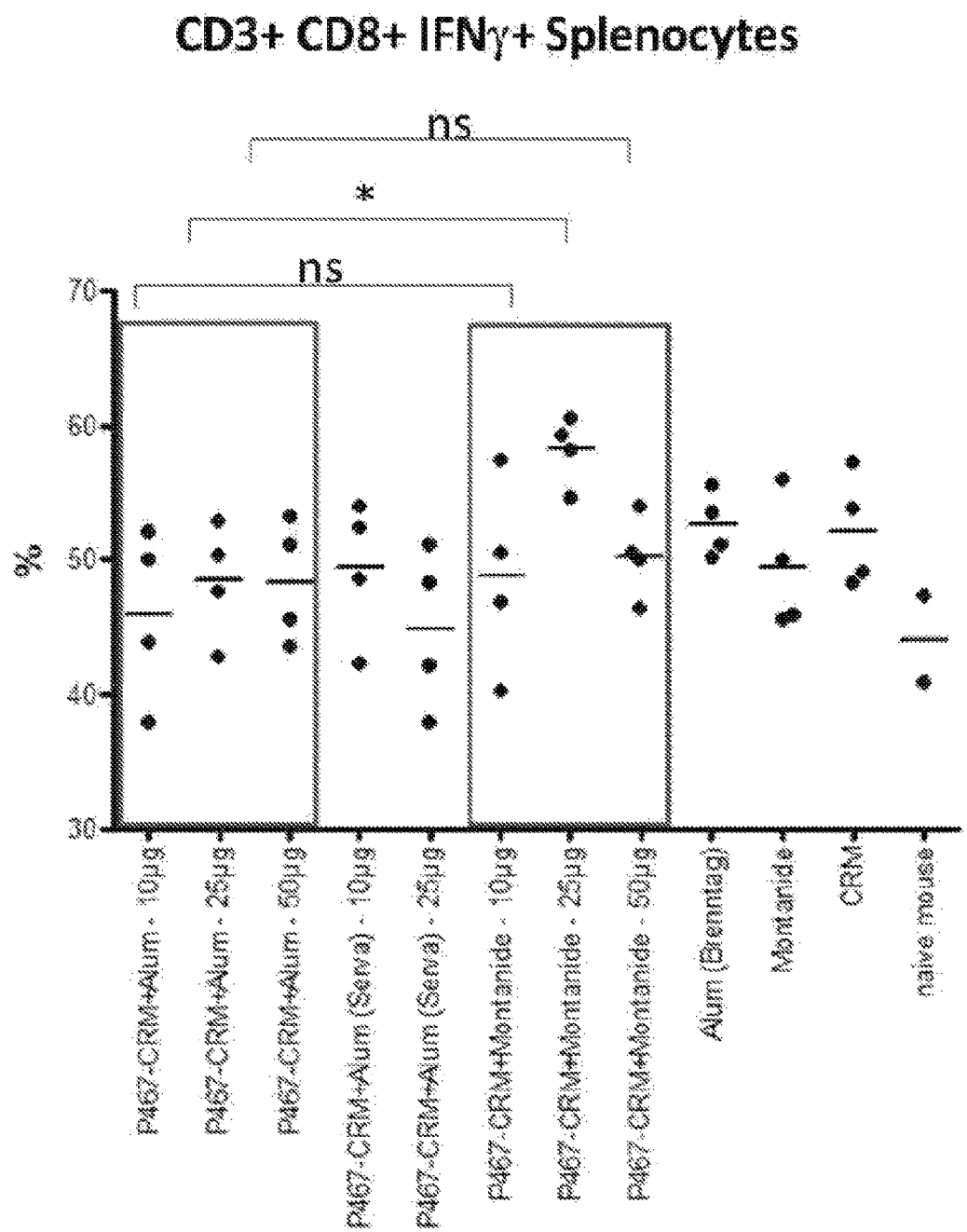
FIG. 21B shows the distribution of CD3+CD8+IFNγ+ splenocytes (IFNγ-producing T cells) at sacrifice in mice immunized with P467-CRM197 fusion protein at 10 μg, 25 μg and 50 μg, administered with Alum from Brenntag (P467-CRM+Alum), with Alum from Serva (P467-CRM+Alum (Serva)) or with Montanide (P467-CRM+Montanide). The percentage of CD3+CD8+IFNγ+ splenocytes was compared to the percentage of CD3+CD8+IFNγ+ splenocytes seen in control animals administered with Alum alone (Alum (Brenntag)), Montanide alone (Montanide) or CRM197 alone (CRM). Data are presented as a percentage of total cell number; *p<0.05 and ns=not statistically significant.
Figure 21C:
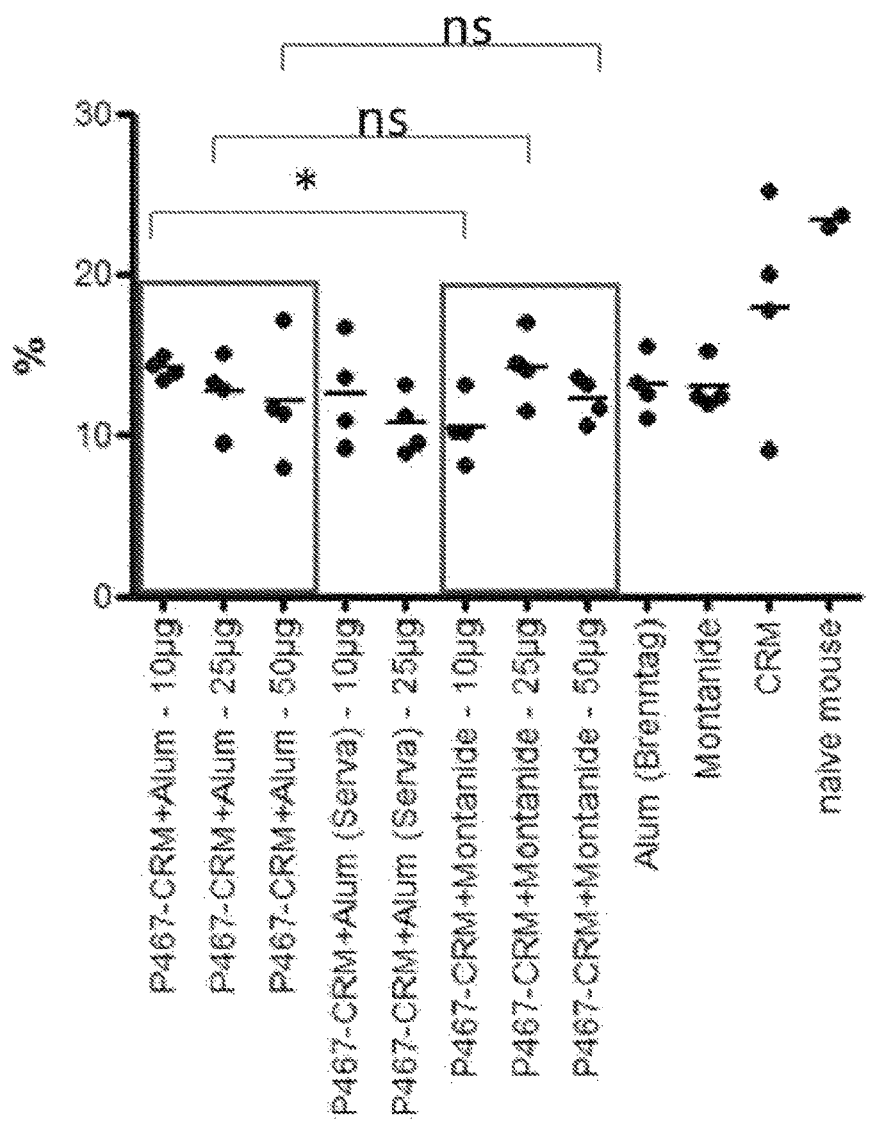
FIG. 21C shows the distribution of CD335+IFNγ+ splenocytes (IFNγ-producing T cells) at sacrifice in mice immunized with P467-CRM197 fusion protein at 10 μg, 25 μg and 50 μg, administered with Alum from Brenntag (P467-CRM+Alum), with Alum from Serva (P467-CRM+Alum (Serva)) or with Montanide (P467-CRM+Montanide). The percentage of CD335+IFNγ+ splenocytes was compared to the percentage of CD335+IFNγ+ splenocytes seen in control animals administered with Alum alone (Alum (Brenntag)), Montanide alone (Montanide) or CRM197 alone (CRM). Data are presented as a percentage of total cell number; *p<0.05 and ns=not statistically significant.

To investigate whether immunization with the different adjuvants would lead to a change in the distribution of IFNγ-producing CD4+ or CD8+ cells, splenocytes of mice from all groups were isolated and intracellular IFNγ was measured in T cells ($CD4^+$, FIG. 21A, and $CD8^+$, FIG. 21B) and NK cells ($CD3^-CD335^+$, FIG. 21C).

The data show that the CD4+ T cells produced IFNγ, which was pronounced in mice immunized with increasing concentrations of P467-CRM. All control groups (and naïve mice) showed similar IFNγ levels. In contrast, IFNγ levels were higher in in CD8+ T cells derived from mice immunized with 25 μg P467-CRM with Montanide. The data also show IFNγ production by NK cells derived from mice immunized with P467-CRM+Montanide.

Kinetics of Anti-Her2 and P467 Peptide Antibody Responses

To evaluate the kinetics of the antibody responses, blood samples were taken at 8 weeks, 16 weeks and 6 months after the last immunization. Blood samples were then analysed for Her2/neu-specific and P467 peptide-specific antibody titres in accordance with the methods disclosed herein.

Figure 22:
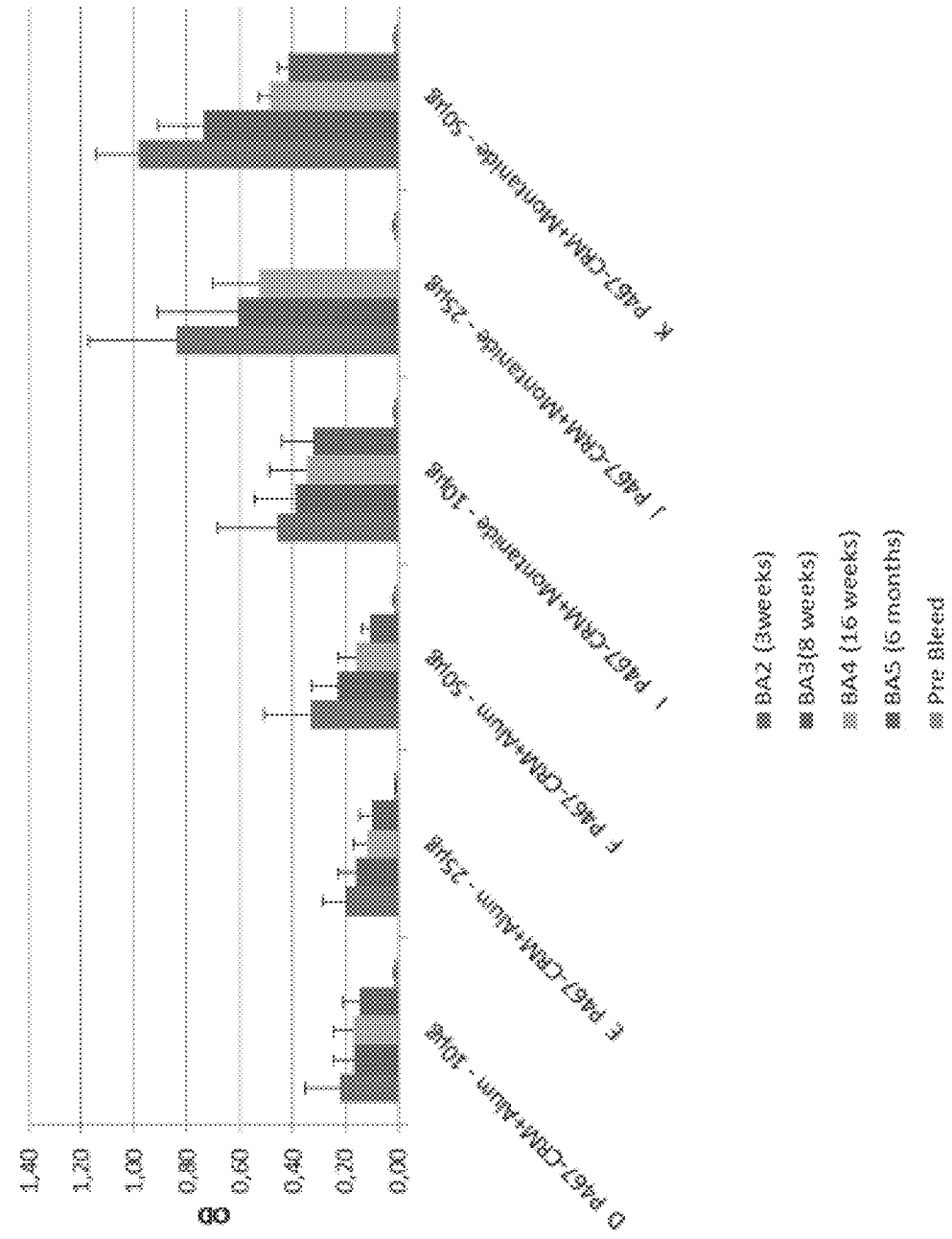
FIG. 22 shows P467 peptide-specific IgG antibody titres at 3 weeks (BA2), 8 weeks (BA3), 16 weeks (BA4) and 6 months (BA5) after the last dose of P467-CRM peptide construct administered at 10 μg, 25 μg and 50 g with either Alum (P467-CRM+Alum) or Montanide (P467-CRM+Montanide). Data are presented as OD values. From left to right in each cluster: BA2, BA3, BA4, BA5 and pre-bleed.
Figure 23:
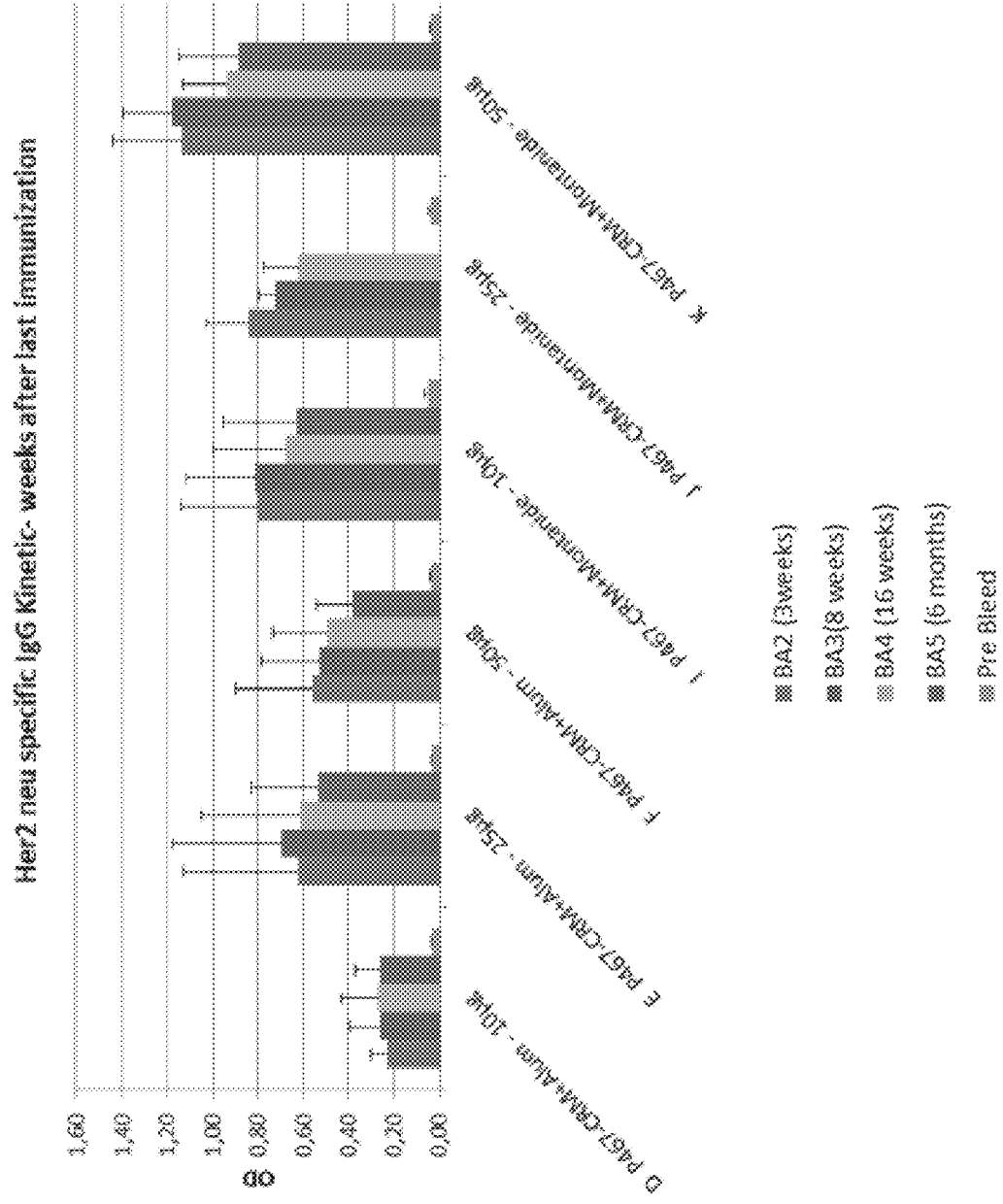
FIG. 23 shows Her2/neu-specific IgG antibody titres at 3 weeks (BA2), 8 weeks (BA3), 16 weeks (BA4) and 6 months (BA5) after the last dose of P467-CRM peptide construct administered at 10 μg, 25 μg and 50 g with either Alum (P467-CRM+Alum) or Montanide (P467-CRM+Montanide). Data are presented as OD values. From left to right in each cluster: BA2, BA3, BA4, BA5 and pre-bleed.

As shown in FIG. 22, P467 peptide-specific IgG antibody titres remained elevated at 8 weeks (BA3), 16 weeks (BA4) and 6 months (BA5) after the last dose of P467-CRM peptide construct administered with either Alum or Montanide. Similarly, as shown in FIG. 23, Her2/ncu-specific IgG antibody titres remained elevated at 8 weeks (BA3), 16 weeks (BA4) and 6 months (BA5) after the last dose of P467-CRM peptide construct administered with either Alum or Montanide.

Summary

Both CRM197-fusion peptide conjugates and virosomal formulations comprising the fusion peptides generated antibodies specific to the single B cell epitopes (P4, P6 and P7), as well as to the fusion peptides (P467 and P647). It is also to be noted that these antibodies also bound to the recombinant extracellular domain of Her-2/neu and to the native Her2/neu protein expressed on SKBR-3 breast cancer cells.

CRM197-fusion peptide conjugates were more effective in inducing B cell epitope- and Her2/neu-specific antibodies; that is, significantly higher antibody titres (approx. 10- to 20-fold) were generated as compared to the corresponding virosomal formulations.

Based on the antibody titres against recombinant Her-2/neu, there was a clear difference in the kinetics of antibody responses in the course of immunisation, with the results showing that CRM-conjugates lead to an earlier increase in antibody titres (already after the $2^{nd}$ immunisation, with a peak after the $3^{rd}$ immunisation), while the increase in antibody titres with virosome conjugates was slower and needed four immunisations to reach levels seen in mice immunized with the corresponding CRM conjugates.

Virosomes are generally a suitable antigen delivery system. However, the results disclosed herein clearly show a delayed increase in antibody titres following immunisation with virosome conjugates, as well as the necessity of four immunisations to achieve similar titres observed in animals immunized with corresponding CRM conjugates. Both time and doses for optimal antibody responses are important factors to be considered for the clinical application of the Her-2/neu vaccine compositions. Thus, these results show that CRM197 is a more suitable carrier protein for Her-2/neu fusion peptides in the context of vaccine delivery.

Both Alum (Brenntag) and Montanide were shown to further increase the aforementioned antibody responses to the P467-CRM peptide construct. Anti-P467-specific IgG, as well as IgG1, antibody tires were significantly higher in all mice immunized with Montanide (in all doses) when compared to Alum. Anti-P467 IgG2a antibody titres were also higher in mice immunized with Montanide (in all doses) compared to Alum. Anti-Her-2/neu IgG and IgG1 antibody titres were significantly higher in mice immunized with Montanide when co-administered with the peptide constructs at all doses that were investigated. In contrast to the P467 peptide-specific antibodies, little or no anti-Her-2/neu IgG2a antibodies were detected.

IFNγ was produced in significantly higher amounts by splenocytes when the cells were cultured in vitro in the presence of CRM, when compared to cells cultured in the presence of P467. After stimulation with CRM, IFNγ levels were significantly higher in the groups administered with the lower doses of the peptide construct when applied with Montanide, in comparison to the groups receiving the same doses of the construct when applied with Alum (Brenntag). The data indicate that Montanide induces higher antibody titres, but also higher cytokine levels than Alum.

The invention claimed is:

1. A composition comprising:
   an adjuvant, wherein the adjuvant is a water-in-oil emulsion; and
   at least one fusion peptide conjugated to a carrier protein, wherein the carrier protein is the diphtheria toxin variant CRM-197 (SEQ ID NO:61) and wherein the at least one fusion peptide comprises two or more non-contiguous B cell epitopes of Her2/neu selected from the group consisting of SEQ ID Nos: 1-7.

2. The composition of claim 1, wherein the fusion peptide comprises an amino acid sequence selected from the group consisting of SEQ ID NOs: 8-14.

3. The composition of claim 2, wherein the fusion peptide comprises an amino acid sequence of SEQ ID NO: 8 or SEQ ID NO:9.

4. The composition of claim 3, wherein the fusion peptide consists of an amino acid sequence of SEQ ID NO: 8 or SEQ ID NO:9.

5. The composition of claim 1, wherein the carrier protein comprises from 2 to 39 fusion peptides.

6. The composition of claim 5, wherein the carrier protein comprises from 6 to 12 fusion peptides.

7. The composition of claim 1, further comprising a checkpoint inhibitor.

8. A pharmaceutical composition comprising the composition of claim 1 and a pharmaceutically acceptable carrier.

9. A method of treating a cancer characterized by expression or over-expression of Her2/neu in a patient in need thereof, the method comprising the step of administering to said patient an effective amount of the composition of claim 1 or the pharmaceutical composition of claim 8.

10. The method of claim 9, wherein the cancer is breast cancer.

11. The method of claim 9, wherein the cancer is gastric cancer.

* * * * *